(12) United States Patent
Imai et al.

(10) Patent No.: US 12,337,010 B2
(45) Date of Patent: Jun. 24, 2025

(54) COMPOSITIONS AND METHODS OF TREATMENT USING NICOTINAMIDE MONONUCLEOTIDE

(71) Applicant: Washington University, St. Louis, MO (US)

(72) Inventors: Shin-ichiro Imai, St. Louis, MO (US); Alessia Grozio, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 18/161,136

(22) Filed: Jan. 30, 2023

(65) Prior Publication Data

US 2023/0338407 A1    Oct. 26, 2023

Related U.S. Application Data

(62) Division of application No. 16/638,064, filed as application No. PCT/US2018/046233 on Aug. 10, 2018, now Pat. No. 11,564,936.

(60) Provisional application No. 62/543,856, filed on Aug. 10, 2017, provisional application No. 62/653,348, filed on Apr. 5, 2018.

(51) Int. Cl.
  *A61K 31/706*   (2006.01)
  *A61K 45/06*    (2006.01)
  *A61K 48/00*    (2006.01)
  *A61P 3/04*     (2006.01)
  *C12N 15/86*    (2006.01)
  *G01N 33/50*    (2006.01)
  *G01N 33/68*    (2006.01)

(52) U.S. Cl.
  CPC ........... *A61K 31/706* (2013.01); *A61K 45/06* (2013.01); *A61K 48/005* (2013.01); *A61P 3/04* (2018.01); *C12N 15/86* (2013.01); *G01N 33/5008* (2013.01); *G01N 33/6803* (2013.01); *C12N 2740/15032* (2013.01); *C12N 2740/15043* (2013.01)

(58) Field of Classification Search
  CPC ............ A61K 2300/00; A61K 31/4406; A61K 31/706; A61K 45/06; A61K 48/005
  See application file for complete search history.

(56) References Cited

U.S. PATENT DOCUMENTS

| | | |
|---|---|---|
| 2006/0002914 A1 | 1/2006 | Milbrandt et al. |
| 2006/0115455 A1 | 6/2006 | Reed et al. |
| 2008/0292546 A1 | 11/2008 | Clarke |
| 2008/0318234 A1 | 12/2008 | Wang |
| 2011/0145936 A1 | 6/2011 | Ostertag et al. |
| 2012/0015841 A1 | 1/2012 | Shekdar et al. |
| 2012/0328583 A1 | 12/2012 | Herzberg et al. |
| 2014/0090094 A1 | 3/2014 | Golz et al. |
| 2015/0313930 A1 | 11/2015 | Sinclair et al. |
| 2016/0022712 A1 | 1/2016 | Mai et al. |
| 2016/0174534 A1 | 6/2016 | Ostertag et al. |

FOREIGN PATENT DOCUMENTS

| | | | |
|---|---|---|---|
| WO | 2004094636 | 11/2004 | |
| WO | 2004096124 A2 | 11/2004 | |
| WO | WO2010086185 A1 * | 8/2010 | ........... A61K 31/455 |
| WO | 2014146044 A1 | 9/2014 | |
| WO | 2017/062311 A1 | 4/2017 | |
| WO | 2017070647 A1 | 4/2017 | |

OTHER PUBLICATIONS

Gia (international Journal of Pharmaceutics, 63 (1990) 129-134).*
Bruzzone, S., et al., "Connexin 43 Hemichannels Mediate CA2+-regulated Transmembrane NAD+ Fluxes in Intact Cells," 2001, Faseb J., 15:10-12, downloaded May 20, 2020 www.fasebj.org,17 pages.
Cabaleiro, T., et al., "Paradoxical Psoriasiform Reactions to Anti-TNFa Drugs are Associated with Genetic Polymorphisms in Patients with Psoriasis," 2016, Pharmacogenomics J, 16:336-340, Abstract only, 1 page.
Canto, C.et al., "NAD+ Metabolism and the Control of Energy Homeostasis: A Balancing Act between Mitochondria and the Nucleus," 2015, Cell Metab. 22, 304, 31-53, 23 pages.
Carlson, L.A., "Nicotinic Acid: The Broad-Spectrum Lipid Drub. A 50th Anniversity Review," 2005, J Int Med, 258:94-114, 21 pages.
Caton, P. W., et al., "Nicotinamide Mononucleotide Protects Against Pro-Inflammatory Cytokine-Mediated Impairment of Mouse Islet Function," 2011, Diabetologia, 54, 3083-3092, 10 pages.
Daigle, N.D., et al., "Molecular Characterization of a Human Cation-CI-Cotransporter (SLC12A8A, CCC9A) that Promotes Polyamine and Amino Acid Transport," 2009, J Cell Physiol, 220:680-689, 10 pages.
De Picciotto, N. E. et al., "Nicotinamide Mononucleotide Supplementation Reverses Vascular Dysfunction and Oxidative Stress with Aging in Mice," 2016, Aging Cell, 15, 522-530, 9 pages.
Franco, L., et al., The Transmembrane Glycoprotein CD38 is a Catalytically Active Transporter Responsible for Generation and Influx of the Second Messenger Cyclic ADP-ribose Across Membranes, 1998, Faseb J., 12, 1507-1520, 14 pages.
Frederick, D. W., et al., "Loss of NAD Homeostasis Leads to Progressive and Reversible Degeneration of Skeletal Muscle," 2016, Cell Metab., 24, 269-282, 14 pages.

(Continued)

*Primary Examiner* — Pancham Bakshi
(74) *Attorney, Agent, or Firm* — Stinson LLP

(57) ABSTRACT

Various methods and compositions for treating age-associated conditions and other medical conditions, such as muscle diseases, type 2 diabetes, and/or obesity are described. Methods of enhancing cellular uptake of NMN and stimulating NAD+ production are further described. Various mammalian cells and mammalian cell lines are described including those comprising a cDNA encoding a Slc12a8 protein. Gene therapy vectors comprising a nucleic acid encoding Slc12a8 and non-human animals comprising an inactivating mutation in a Slc12a8 gene are also disclosed. Also described are methods for screening a candidate compound to identify compounds that promote NMN transport.

4 Claims, 37 Drawing Sheets

Specification includes a Sequence Listing.

(56) References Cited

OTHER PUBLICATIONS

Gagnon, K.B., et al., "Physiology of SLC12 Transporters: Lessons from Inherited Human Genetic Mutations and Genetically Engineered Mouse Knockouts," 2013, Am. J. Physiol. Cell Physiol., 304/8:C693-714, 50 pages.
Garten, A. et al., "Physiological and Pathophysiological Roles of NAMPT and NAD Metabolism," 2015, Nat. Rev. Endocrinol., 11, 535-546, Abstract only, 1 page.
Gomes, A. P. et al., "Declining NAD+ Induces a Pseudohypoxic State Desrupting Nuclear-Mitochondrial Communication During Aging," 2013, Cell, 155/7:1624-1638, 15 pages.
Grimm, A. A., et al., "A Nutrient-Sensitive Interaction Between Sirt1 and HNF-1alpha Regulates Crp Expression," 2011, Aging Cell, 10, 305-317, 13 pages.
Hebert, S. C., et al., "Molecular Physiology of Cation-Coupled Cl-Cotransport: The SLC12 Family," 2004, Pflugers Arch. 447:580-593, 14 pages.
Hotz W., "Nicotinic Acid and its Derivatives: A Short Survey," 1983, Adv Lipid Res, 20:195-217, Abstract only, 1 page.
Huang, X., et al., "Polymorphisms of Three Gene-Derived STS on Pig Chromosome 13q41 are Associated with Suseptibility to Enterotoxigenic *Escherichia coli* F4ab/ac in Pigs," 2008, Sci in China Series C: Life Sciences, 51: 614-619, Abstract only, 1 page.
Imai, S., et al., NAD+ and Sirtuins in Aging and Disease, 2014, Trends Cell Biol, 24/8:464-471, 17 pages.
Imai, S., "Nicotinamide Phosphoribosyltransferase (Nampt): A link between NAD Biology, Metabolism, and Diseases," 2009, Curr Pharm Des, 15/1:20-28, 16 pages.
Kim, et al., "Kinetic Study on Aminolysis of 4-Nitrophenyl Nicotinate and Isonicotinate: Factors Influencing Reactivity and Reaction Mechanism", 2014, Bull Korean Chem Soc, 35/8:2443-2447, 5 pages.
Kubo, Y., et al., "Involvement of the Carrier-Mediated Process in the Retina-to-Blood Transport of Spermine at the Inner Blood-Retinal Barrier," Jul. 2014, Exp Eye Res, 124:17-23, Abstract only, 1 page.
Kulikova et al., "Generation, Release, and Uptake of the NAD Precursor Nicotinic Acid Riboside by Human Cells," 2015, J. Biol Chem, 290/45:27124-27137, 14 pages.
Long, A. N., et al., "Effect of Nicotinamide Mononucleotide on Brain Mitochondrial Respiratory Deficits in an Alzheimer's Disease-Relevant Murine Model," 2015, BMC Neurol., 15/19, 14 pages.
Mills, K. F. et al., "Long-Term Administration of Nicotinamide Mononucleotide Mitigates Age-Associated Physiological Decline in Mice," 2016, Cell Metab., 24, 795-806, 13 pages.
Ramsey, K. M., et al., "Circadian Clock Feedback Cycle Through NAMPT-Mediated NAD+ Biosynthesis," 2009, Science, 324, 651-654, 9 pages.
Ramsey, K. M., et al., "Age-Associated Loss of Sirt1-Mediated Enhancement of Glucose-Stimulated Insulin Secretion Iin Beta Cell-Spedific Sirt1-Overexpressing (BESTO) Mice," 2008, Aging Cell, 7, 78-88, 11 pages.
Ratajczak J., et al., "NRK1 controls nicotinamide monucleotide and nicotinamide riboside metabolism in mammalian cells," 2016, Nature Communications, 7:131303, doi: 10: 1038/ncomms13103, 12 pages.
Revollo, J. R. et al., Nampt/PBEF/Visfatin Regulates Insulin Secretion in Beta Cells as a Systemic NAD Biosynthetic Enzyme, 2007, Cell Metabolism, 6:363-375, 13 pages.
Sato, T., et al., "Primary Mouse Small Intestinal Epithelial Cell Cultures," 2013, Epithelial Cell Culture Protocols, Methods Mol. Biol. 945:319-328, Abstract only, 1 page.
Satoh, A. et al., "Sirt1 Extends Life Span and Delays Aging in Mice Through the Regulation of Nk2 Homeobox 1 in the DMH and LH," 2013, Cell Metabolism, 18:416-430, 15 pages.
Scalise, M., et al., "Proteoliposomes as Tool for Assaying Membrane Transporter Functions and Interactions with Xenobiotics," 2013, Pharmaceutics, 5:472-497, 26 pages.
Sociali, G., et al., "Antitumor Effect of Combined NAMPT and CD73 Inhibition in an Ovarian Cancer Model," Oncotarget, 7/3:2968-2984, 17 pages.
Stein, L. R., et al., "Specific Ablation of Nampt in Adult Neural Stem Cells Recapitulates Their Functional Defects During Aging," 2014, Embo J., 33:1321-1340, 20 pages.
Wang, X., et al., "Nicotinamide Mononucleotide Protects Against Beta-Amyloid Oligomer-Induced Cognitive Impairment and Neuronal Death," 2016, Brain Res., 1643:1-9, Abstract only, 1 page.
Wernly-Chung, et al., "Structure-Reactivity Relationships in the Chemical Hydrolysis of Prodrug Esters of Nicotinic Acid, 1990, Intl J Pharma," 63:129-134, 6 pages.
Yamada, K., et al., "The Simultaneous Measurement of Nicotinamide Adenine Dinucleotide and Related Compounds by Liquid Chromatography/Electrospray Ionization Tandem Mass Spectrometry," Anal Biochem, 352/2:282-285, Abstract only, 1 page.
Yamamoto, T. et al., "Nicotinamide Mononucleotide, an Intermediate of NAD+ Synthesis, Protects the Heart from Ischemia and Reperfusion," 2014, PLoS One, 9/6:e98972, 14 pages.
Yoon, M.J., et al., "SIRT1-Mediated eNAMPT Secretion from Adipose Tissue Regulates Hypothalamic NAD+ and Function in Mice," 2015, Cell Metabolism, 21:706-717, 12 pages.
Yoshino, J., et al., "Nicotinamide Mononucleotide, a Key NAD+ Intermediate, Treats the Pathophysiology of Diet- and Age-Induced Diabetes in Mice," 2011, Cell Metabolism., 14/4:528-536, 9 pages.
SuperFect Transfection Reagent Handbook, Dec. 2002, Qiagen Distributors, 32 pages.
Therapeutic Class Overview: Niacin Derivatives, 2014, University of Massachusetts Medical School, 52 pages.
PhenoMaster, Highlights in Metabolic, Behavioral & Physiological Phenotyping of Mice & Rats, 2015, TSE Systems,, Info@TSE-Systems.com, 8 pages.
UniProtKB Accession No. A0AV02 "S12AB_Human", https://www.uniprot.org/uniprot/A0AV02.txt, Oct. 2, 2007, Sequence on p. 6, retrieved Nov. 28, 2018, 6 pages.
International Search Report and Written Opinion issued in PCT/US2018/046233, issued Dec. 11, 2018, 17 pages.
International Preliminary Report on Patentability issued in PCT/US2018/046233, issued Feb. 20, 2020, 12 pages.
Skolnick et al., From genes to protein structure and function: novel applications of computational approaches in the genomic era, Trends in Biotechnology 18: 34-39 (2000).
Niacin Trp NMN, Amazon, Jan. 27, 2016, https://www.amazon.com/MIRAI-LAB-Niacin-Trp-NMN/dp/B00V7J8DNE/ref=cm_cr_arp_d_product_top?ie=UTF8, 3 pages.
Arroyo et al., "The SLC12 Family of Electroneutral Cation-Coupled Chloride Cotransporters," Mol. Asp. Med., 34(2-3):288-298, Apr.-Jun. 2013.

\* cited by examiner

A

B

COMPOSITIONS AND METHODS OF TREATMENT USING NICOTINAMIDE MONONUCLEOTIDE

STATEMENT OF GOVERNMENT SUPPORT

This invention was made with government support under AG047902 and AG037457 awarded by the National Institutes of Health. The government has certain rights in the invention.

REFERENCE TO A SEQUENCE LISTING

The Sequence Listing, which is a part of the present disclosure, includes a text file named "WSTL17227.USD1 ST.26 Sequence Listing.xml," which is 25,743 bytes in size and was created on Jan. 24, 2023. This Sequence Listing comprises primer, nucleotide and/or amino acid sequences of the present invention and consists of SEQ ID NOs: 1-15. The subject matter of the Sequence Listing is incorporated herein by reference in its entirety. The information recorded in computer readable form is identical to the written sequence listing.

FIELD OF THE INVENTION

The present disclosure relates to various methods and compositions for treating age-associated conditions and other medical conditions, such as muscle diseases, type 2 diabetes, and/or obesity are described. Methods of enhancing cellular uptake of NMN and stimulating NAD+ production are further described. Various mammalian cells and mammalian cell lines are described including those comprising a cDNA encoding a Slc12a8 protein. Gene therapy vector comprising a nucleic acid encoding Slc12a8 and non-human animals comprising an inactivating mutation in a Slc12a8 gene are also disclosed. Also described are methods for screening a candidate compound to identify compounds that promote NMN transport.

BACKGROUND OF THE INVENTION $NAD^+$ is a universal and essential coenzyme involved in many cellular redox reactions. $NAD^+$ is also required for the activities of $NAD^+$-consuming enzymes, including the sirtuin family of $NAD^+$-dependent protein deacetylases, poly-ADP-ribose polymerases (PARPs), and CD38/157 $NAD^+$ hydrolases/cyclic ADP-ribose synthases (Canto, C., et al., *Cell Metab.* 22, 304, 31-53, 2015; Imai, S. and Guarente, L., *Trends in Cell Biology*, 24, 306 464-471, 2014). To generate $NAD^+$, mammals utilize various precursors such as tryptophan, nicotinamide and nicotinic acid (also known as two forms of vitamin $B_3$), and intermediates that include nicotinamide riboside (NR) and nicotinamide mononucleotide (NMN). The salvage pathway starting from nicotinamide is a predominant $NAD^+$ biosynthetic pathway in mammals (Garten, A., et al., *Nat. Rev. Endocrinol.*, 11, 535-546, 2015.; Imai, S., *Curr. Pharm. Des.*, 15, 20-28, 2009). In this pathway, nicotinamide phosphoribosyltransferase (NAMPT) produces NMN from nicotinamide and 5'-phosphoribose pyrophosphate. NMN, together with ATP, is then converted into $NAD^+$ by NMN adenylyltransferases, NMNAT1-3. The product of the NAMPT reaction is NMN, a key $NAD^+$ intermediate. NAMPT is the rate-limiting NAD+ biosynthetic enzyme in mammals. Without being bound to any particular theory, it is thought that NMN may be useful in connection with the prevention and/or treatment of various disease conditions and mitigation of age-associated physiological decline. However, the mechanism of NMN transport has been controversial.

Slc12a8 was originally identified by Gagnon, K. B. & Delpire, E. (*Am. J. Physiol. Cell Physiol.*, 304, C693-714, 2013). However, Gagnon et al. did not identify a function for Slc12a8. Kubo, Y., et al. (*Exp. Eye Res.*, 124, 17-23, 2014) identified Slc12a8 as a spermine transporter, but did not disclose that it was involved in NMN transport.

BRIEF SUMMARY OF THE INVENTION

Various methods of treating an age-associated condition in a subject in need thereof are provided. Typically, the methods comprise administering to the subject a therapeutically effective amount of nicotinamide mononucleotide (NMN) and at least one additional compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof, and wherein the age-associated condition comprises at least one condition selected from the group consisting of loss of insulin sensitivity, loss of insulin secretion, loss of insulin action and secretion, impairment of memory function, decline in eye function, retinal degeneration, functional decline, and combinations of any thereof.

Other methods relate to treating a medical condition in a subject in need thereof. The methods comprise administering to the subject a therapeutically effective amount of nicotinamide mononucleotide (NMN) and at least one compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof, wherein the medical condition comprises at least one selected from the group consisting of a muscle disease, type 2 diabetes, obesity, and combinations of any thereof.

A method of enhancing cellular uptake of NMN in a subject in need thereof is also provided. These method comprises administering to the subject a therapeutically effective amount of a compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof.

A method for stimulating NAD+ production and/or increasing NMN uptake into cells in a subject in need thereof is provided. The method comprises administering to the subject a therapeutically effective amount of a nucleic acid encoding Slc12a8.

A gene therapy vector is provided. The gene therapy vector comprises a nucleic acid encoding Slc12a8.

A non-human animal is provided. The non-human animal comprises an inactivating mutation in a Slc12a8 gene.

A mammalian cell or mammalian cell line is provided. The mammalian cell or mammalian cell line comprises a cDNA encoding a Slc12a8 protein. The cDNA comprises a cDNA encoding SEQ ID NO: 12 (mouse Slc12a8 protein), SEQ ID NO: 13 (mouse Slc12a8 variant A protein), SEQ ID NO: 14 (mouse Slc12a8 variant B protein), or SEQ ID NO: 15 (human Slc12a8 protein).

A further mammalian cell or mammalian cell line is provided. The mammalian cell or mammalian cell line comprises a cDNA encoding a Slc12a8 protein. The cDNA comprises a cDNA encoding a protein having at least 70%, at least 75%, at least 80%, at least 85%, at least 90%, at least 95%, or at least 99% identity with SEQ ID NO: 12, SEQ ID NO: 13, SEQ ID NO: 14, or SEQ ID NO: 15.

Yet another mammalian cell or mammalian cell line is provided. The mammalian cell or mammalian cell line comprises a cDNA encoding a Slc12a8 protein. The cDNA comprises a cDNA sequence having at least 70%, at least 75%, at least 80%, at least 85%, at least 90%, at least 95%, at least 99%, or 100% sequence identity with GenBank Reference Sequence: NM_134251 (SEQ ID NO: 1) or Slc12a8 human full-length CDNA (SEQ ID NO: 11).

Another mammalian cell or a mammalian cell line is provided. The cell or cell line comprises a cDNA encoding a Slc12a8 protein. The cell or cell line does not comprise placental-derived cells.

Methods for screening a candidate compound to identify compounds that modulate NMN transport are provided. The methods comprise (a) contacting the candidate compound with a cell that expresses an NMN transporter protein or a proteoliposome comprising an NMN transporter protein; and (b) detecting a change in the expression or activity of the NMN transporter protein in the cell or a change in the activity of the NMN transporter protein in the proteoliposome. A change in the expression or activity of the NMN transporter protein in the cell or a change in the activity of the NMN transporter protein in the proteoliposome following contact with the candidate compound indicates that the candidate compound modulates the transport of NMN.

A pharmaceutical composition is provided. The pharmaceutical composition comprises NMN and an agonist of an NMN transporter.

A further pharmaceutical composition is provided. The pharmaceutical composition comprises NMN and an inducer of gene expression of Slc12a8 or a homolog thereof.

DETAILED DESCRIPTION

Figure 1:
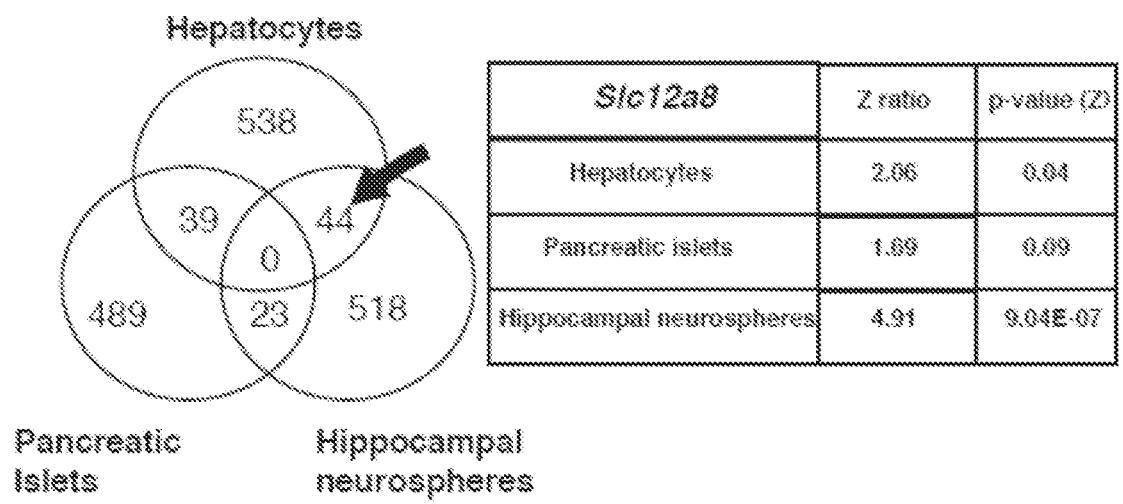
FIG. 1 is a Venn diagram of genes commonly upregulated in primary hepatocytes, pancreatic islets and hippocampal neurospheres treated with FK866.

Disclosed herein are methods of enhancing NMN uptake into cells. Also disclosed are cell lines useful for studying Slc12a8 and NMN transport therefor. The present inventors have also identified a transporter, Slc12a8, which enhances NMN uptake into cells.

Methods disclosed herein can be used for treating, ameliorating, mitigating, or reversing any disease or condition which involves NMN metabolism, such as, without limitation, type II diabetes, obesity, age-related obesity, age-related increases in blood lipid levels, age-related decreases in insulin sensitivity, age-related loss or decrease in memory function, age-related loss or decrease in eye function, age-associated physiological decline, impairment in glucose-stimulated insulin secretion, diabetes, amelioration of mitochondrial function, neural death, and/or cognitive function in Alzheimer's disease, protection of heart from ischemia/ reperfusion injury, maintenance of neural stem/progenitor cell populations, restoration of skeletal muscle mitochondrial function and arterial function following injury, and age-related functional decline.

The present teachings include, without limitation:
1. A full-length cDNA of a mammalian Slc12a8 mRNA such as a mouse Slc12a8 mRNA or a human Slc12a8 mRNA.
2. A cDNA encoding a mouse Slc12a8 polypeptide or a human Slc12a8 polypeptide.
3. A mammalian expression vector comprising a Slc12a8 cDNA, such as a full-length Slc12a8 cDNA.
4. A cell line such as an NIH3T3 cell line harboring a Slc12a8 cDNA, including a cell line which overexpresses a Slc12a8 cDNA such as a full-length mouse Slc12a8 cDNA (Slc12a8-OE cells) or a full-length human Slc12a8 cDNA.
5. A Lentivirus harboring a shRNA that reduces or silences expression of a Slc12a8 mRNA.
6. A polyclonal antibody, including a rabbit polyclonal antibody, against N-terminal and internal domains of a Slc12a8 protein such as a mouse Slc12a8 protein or a human Slc12a8 protein.
7. A whole-body Slc12a8 knockout mouse.

The present teachings include a proteoliposome system, which comprises liposomes with a transport protein such as a Slc12a8 protein embedded in a membrane bilayer. Such a system can be used for analyzing the properties of an Slc12a8 protein and for testing a candidate drug for affinity to Slc12a8, or for activity as an agonist or antagonist of Slc12a8 activity.

The present teachings include methods of facilitating uptake of NMN in cells, tissues, and organs, such as the gut. These methods can include administering a cDNA of Slc12a8 to the gut. These methods can include administering a lentivirus comprising a cDNA encoding Slc12a8 to the gut.

The methods of facilitating uptake of NMN can include administering NMN in combination with a sodium salt. For example, the administration can be oral administration.

The present teachings include administration to a subject in need thereof a nicotinic acid (NA) or an NA derivative compound (i.e., a structural analogue of NA) to enhance NMN uptake. The present teachings include administration of nicotinic acid (NA) or an NA derivative compound (i.e., a structural analogue of NA) to enhance the NMN uptake function of the Slc12a8 NMN transporter in a subject in need thereof. The nicotinic acid (NA) or NA derivative compound can be administered to a subject in need thereof at a dosage range such as, without limitation, 10-500 mg/day or 50-500 mg/day for the NA or NA derivative compound. The administration can be oral administration, parenteral administration, or a combination of any thereof.

The present teachings include administration of NA or an NA derivative compound in combination with NMN to promote or facilitate the uptake of NMN in a subject in need thereof, which can be by enhancing the NMN uptake function of the Slc12a8 NMN transporter. Such a combination can be administered to a subject in need thereof at a dosage range such as, without limitation, 10-500 mg/day, or 50-500 mg/day, for each of NMN and NA or NA derivative compound. The administration can be oral administration, parenteral administration, or a combination thereof.

The present teachings include administration of a combination of NMN, and some salts (e.g., Na+) to facilitate the uptake of NMN in a subject in need thereof. The combination can be an orally administered combination. The combination can be a parenterally administered combination. The NMN and an NMN uptake-promoting salt such as a sodium salt can each be administered at a dosage range such as, without limitation, 10-500 mg/day, or 50-500 mg/day.

The present teachings can include administration of a combination of NMN, a sodium salt, and nicotinic acid (NA) or an NA derivative compound to promote the uptake of NMN in a subject in need thereof. One or any combination of NMN, a sodium salt, and nicotinic acid (NA) or an NA derivative compound can be administered orally. The administration can comprise oral administration for any or all of the NMN, the sodium salt and the nicotinic acid (NA) or an NA derivative compound. The NMN, the sodium salt and the nicotinic acid (NA) or an NA derivative compound can each be administered to a subject in need thereof at a dosage range such as, without limitation, 10-500 mg/day, or 50-500 mg/day.

The present teachings also include administration of nicotinamide riboside (NR) or a NR derivative compound to suppress the NMN uptake function of the Slc12a8 NMN transporter in a subject in need thereof. The nicotinamide riboside (NR) or a NR derivative compound can be administered orally. The NR or NR derivative compound can be administered at a dosage range such as, without limitation, 10-500 mg/day, or 50-500 mg/day, to a subject in need thereof.

The present teachings also include administration of a non-sodium salt such as, for example, a lithium salt, to suppress the NMN uptake function of the Slc12a8 NMN transporter in a subject in need thereof. The non-sodium salt can be administered orally. The non-sodium salt can be administered at a dosage range such as, without limitation, 10-500 mg/day, or 50-500 mg/day, to a subject in need thereof.

The present teachings include administration of nicotinamide riboside (NR) or an NR derivative compound, in combination with a non-sodium salt, such as, for example, a lithium salt, to suppress the NMN uptake function of the Slc12a8 NMN transporter in a subject in need thereof. The NR or NR derivative compound, and/or the non-sodium salt can be administered orally. The NR or NR derivative compound, and the non-sodium salt, can each be administered at a dosage range such as, without limitation, 10-500 mg/day, or 50-500 mg/day, to a subject in need thereof.

The present teachings disclose methods of stimulating NAD+ production in a subject. The method can comprise administering to a subject in need thereof a nucleic acid comprising a genomic DNA or a cDNA encoding a Slc12a8. The nucleic acid can be or can comprise a lentivirus comprising a genomic DNA or a cDNA encoding a Slc12a8, such as, without limitation, a cDNA having a sequence set forth as NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The subject can be a mammal (e.g., a mouse, a rat, or a human). The cDNA encoding a Slc12a8 can be of sequence having at least 70% sequence identity with GenBank Reference Sequence: NM_134251 (SEQ ID NO: 1), at least 70% sequence identity with Slc12a8 mouse variant A (SEQ ID NO: 9), at least 70% sequence identity with Slc12a8 mouse variant B (SEQ ID NO: 10), or at least 70% sequence identity with Slc12a8 human full-length cDNA (SEQ ID NO: 11). The cDNA encoding Slc12a8 can be of sequence of GenBank Reference Sequence NM_134251, or can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity with GenBank Reference Sequence: NM_134251 (SEQ ID NO: 1).

The cDNA encoding Slc12a8 can be of sequence of SEQ ID NO: 9, or can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with SEQ ID NO: 9.

The cDNA encoding Slc12a8 can be of sequence of Slc12a8 mouse variant b set forth as SEQ ID NO: 10, or can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 mouse variant b (SEQ ID NO: 10).

The cDNA encoding Slc12a8 can be of sequence of Slc12a8 human full-length sequence set forth as SEQ ID NO: 11, or can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 human full-length sequence (SEQ ID NO: 11).

The present teachings include methods of promoting or increasing NMN uptake into cells in a subject. The method can comprise administering to a subject in need thereof a nucleic acid comprising a cDNA encoding Slc12a8 or a sequence having at least 70% sequence identity with GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The sequence having at least 70% sequence identity with GenBank Reference Sequence: NM_134251 (SEQ ID NO: 1) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with GenBank Reference Sequence: NM_134251 (SEQ ID NO: 1). The sequence having at least 70% sequence identity with Slc12a8 mouse variant a (SEQ ID NO: 9) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 mouse variant a (SEQ ID NO: 9). The sequence having at least 70% sequence identity with Slc12a8 mouse variant b (SEQ ID NO: 10) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 mouse variant b (SEQ ID NO: 10). The sequence having at least 70% sequence identity with Slc12a8 full-length human cDNA (SEQ ID NO: 11) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 full-length human cDNA (SEQ ID NO: 11). The cDNA can be administered to the gut. This administering can comprise administration by gavage. This administration can comprise an oral pharmaceutical designed to dissolve in the small intestine.

The present teachings include a knock-out mouse comprising a deletion in a Slc12a8 gene. The deletion can be a complete deletion of a Slc12a8 gene, or a partial deletion of a Slc12a8 gene, such as, for example but without limitation, a deletion of exon 4 of the Slc12a8 gene or a deletion within exon 4 of the Slc12a8 gene.

The present teachings include a mammalian cell line comprising an introduced sequence of a Slc12a8 gene or cDNA such as a sequence set forth as GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The introduced Slc12a8 gene or cDNA can be of an exogenous origin, or can be of the same species as the host mammalian cell line. The mammalian cell line can express an Slc12a8 polypeptide at a level higher than that of a parent cell line to which no Slc12a8 gene or cDNA has been introduced.

The present teachings include a mammalian cell line comprising a non-naturally occurring sequence, i.e., a sequence introduced to the cell line by transformation or transfection, and having at least 70% sequence identity with GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The sequence having at least 70% sequence identity with GenBank Reference Sequence: NM_134251 (SEQ ID NO: 1) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with GenBank Reference Sequence: NM_134251 (SEQ ID NO: 1). The sequence having at least 70% sequence identity with Slc12a8 mouse variant a (SEQ ID NO: 9) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 mouse variant a (SEQ ID NO: 9). The sequence having at least 70% sequence identity with Slc12a8 mouse variant b (SEQ ID NO: 10) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 mouse variant b (SEQ ID NO: 10). The sequence having at least 70% sequence identity with Slc12a8 full-length human cDNA (SEQ ID NO: 11) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with Slc12a8 full-length human cDNA (SEQ ID NO: 11).

The present teachings include a mammalian cell line comprising a Slc12a8 sequence such as GenBank Reference Sequence: NM_134251 (SEQ ID NO: 1), a Slc12a8 mouse variant A (SEQ ID NO: 9), Slc12a8 mouse variant B (SEQ ID NO: 10), or Slc12a8 human full-length cDNA (SEQ ID NO: 11). The Slc12a8 sequence of a cell line of the present teachings can be of heterologous origin to the host cell.

A cell line of the present teachings can comprise a Slc12a8 sequence which can be a sequence having at least 70% sequence identity with GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The sequence can be that of a genomic or cDNA encoding a Slc12a8. A genomic or cDNA encoding a Slc12a8 of a cell line of the present teachings can be of heterologous origin to the host cell. The cell line comprising a sequence encoding a Slc12a8 can further comprise a promoter operably linked to the sequence encoding a Slc12a8. The cell line can be a mammalian cell line. The mammalian cell line can lack CD73 activity, can lack CD38 activity or can lack both CD73 activity and CD38 activity. The mammalian cell line can be an NIH 3T3 cell line. The mammalian cell line can be a stably transformed cell line comprising a sequence having at least 70% sequence identity with GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11). The sequence having at least 70% sequence identity with GenBank Reference Sequence: NM_134251 (SEQ ID NO: 1) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with GenBank Reference Sequence: NM_134251 (SEQ ID NO: 1). The mammalian cell line can be transiently transfected with the sequence having at least 70% sequence identity with GenBank Reference Sequence: NM_134251 (SEQ ID NO: 1). The sequence having at least 70% sequence identity with GenBank Reference Sequence: NM_134251 (SEQ ID NO: 1) can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with GenBank Reference Sequence: NM_134251 (SEQ ID NO: 1). The mammalian cell line can be a mouse cell line, a rat cell line, or a human cell line. The mammalian cell line can be selected from the group consisting of a mouse cell line and a rat cell line. The mammalian cell line can be a human cell line. The sequence having at least 70% sequence identity with GenBank Reference Sequence: NM_134251 (SEQ ID NO: 1), Slc12a8 mouse variant A (SEQ ID NO: 9), Slc12a8 mouse variant B (SEQ ID NO: 10), or Slc12a8 human full-length cDNA (SEQ ID NO: 11) can be a full-length Slc12a8 cDNA.

Methods of the present teachings can comprise a method of enhancing cellular uptake of NMN in a subject in need thereof. These methods can comprise administering a therapeutically effective amount of nicotinic acid or an ester or pharmaceutically acceptable salt thereof to a subject in need thereof. The ester or pharmaceutically acceptable salt thereof of nicotinic acid can be a structure

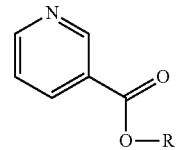

or a pharmaceutically acceptable salt thereof, wherein R can be selected from the group consisting of H, methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl. R can be H, 2-dimethylaminoethyl, p-chlorophenyl, or p-nitrophenyl. R can be selected from the group consisting of H, 2-dimethylaminoethyl, p-chlorophenyl, and p-nitrophenyl. R can be selected from the group consisting of 2-dimethylaminoethyl, p-chlorophenyl, and p-nitrophenyl. R can be selected from the group consisting of H, $C_1$-$C_6$ linear alkyl, $C_3$-$C_6$ branched chain alkyl, $C_3$-$C_6$ cycloalkyl, $C_1$-$C_6$ linear alkoxy, $C_3$-$C_6$ branched chain alkoxy and $C_3$-$C_6$ cycloalkoxy. R can be selected from the group consisting of H, $C_1$-$C_6$ linear alkoxy, $C_3$-$C_6$ branched chain alkoxy, $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxymethyl, alkoxyethyl, alkoxyalkoxymethyl, alkoxyalkoxyethyl, benzyl, alkoxybenzyl, napthyl and alkoxynaphthyl.

R can be selected from the group consisting of methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl. R can be 2-dimethylaminoethyl, p-chlorophenyl, or p-nitrophenyl. R can be selected from the group consisting of 2-dimethylaminoethyl, p-chlorophenyl, and p-nitrophenyl. R can be selected from the group consisting of 2-dimethylaminoethyl, p-chlorophenyl, and p-nitrophenyl. R can be selected from the group consisting of $C_1$-$C_6$ linear alkyl, $C_3$-$C_6$ branched chain alkyl, $C_3$-$C_6$ cycloalkyl, $C_1$-$C_6$ linear alkoxy, $C_3$-$C_6$ branched chain alkoxy and $C_3$-$C_6$ cycloalkoxy. R can be selected from the group consisting of $C_1$-$C_6$ linear alkoxy, $C_3$-$C_6$ branched chain alkoxy, $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxymethyl, alkoxyethyl, alkoxyalkoxymethyl, alkoxyalkoxyethyl, benzyl, alkoxybenzyl, napthyl and alkoxynaphthyl.

The present teachings include methods of enhancing cellular uptake of NMN in a subject in need thereof. These methods can comprise administering to a subject a compound or a pharmaceutically acceptable salt thereof, wherein the compound can be nicotinic acid

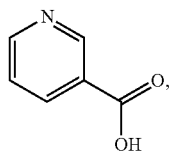

niceritrol, tocopherol nicotinate, β-pyridylcarbinol or inositol hexanicotinate. The compound can be selected from the group consisting of nicotinic acid, niceritrol, tocopherol nicotinate, β-pyridylcarbinol and inositol hexanicotinate. The compound or pharmaceutically acceptable salt thereof can be nicotinic acid or a pharmaceutically acceptable salt thereof. The administering can comprise administering 50-500 mg of nicotinic acid or pharmaceutically acceptable salt thereof per day. The administering can comprise administering 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg of nicotinic acid or pharmaceutically acceptable salt thereof per day. The administering can comprise administering 50-55, 55-60, 60-65, 65-70, 70-75, 85-80, 80-85, 85-90, 90-95, 95-100, 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, 195-200, 200-205, 205-210, 210-215, 215-220, 220-225, 225-230, 230-235, 235-240, 240-245, 245-250, 250-255, 255-260, 260-265, 265-270, 270-275, 275-280, 280-285, 285-290, 290-295, 295-300, 300-305, 305-310, 310-315, 315-320, 320-325, 325-330, 330-335, 335-340, 340-345, 345-350, 350-355, 355-360, 360-365, 365-370, 370-375, 375-380, 380-385, 385-390, 390-395, 395-400, 400-405, 405-410, 410-415, 415-420, 420-425, 425-430, 430-435, 435-440, 440-445, 445-450, 450-455, 455-460, 460-465, 465-470, 470-475, 475-480, 480-485, 485-490, 490-495, or 495-500 mg of nicotinic acid or pharmaceutically acceptable salt thereof per day. The administering can comprise administering 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500 mg of nicotinic acid or pharmaceutically acceptable salt thereof per day. The administering a compound or a pharmaceutically acceptable salt thereof can comprise administering the compound or a pharmaceutically acceptable salt thereof with a pharmaceutically acceptable excipient.

The present teachings include methods of treating, ameliorating, reducing, preventing or reversing age-associated loss of insulin sensitivity and/or insulin secretion in a subject in need thereof. The method of treating, ameliorating, reducing, preventing or reversing age-associated loss of insulin sensitivity in a subject in need thereof, can comprise administering an effective amount of NMN or a pharmaceutically acceptable salt thereof, and an effective amount of at least one of nicotinic acid, or a pharmaceutically acceptable salt thereof, niceritrol or a pharmaceutically acceptable salt thereof, tocopherol nicotinate or a pharmaceutically acceptable salt thereof, or β-pyridylcarbinol inositol hexanicotinate or a pharmaceutically acceptable salt thereof. The method of treating, ameliorating, reducing, preventing or reversing age-associated loss of insulin secretion in a subject in need thereof, can comprise administering an effective amount of NMN or a pharmaceutically acceptable salt thereof, and an effective amount of at least one of nicotinic acid, or a pharmaceutically acceptable salt thereof, niceritrol or a pharmaceutically acceptable salt thereof, tocopherol nicotinate or a pharmaceutically acceptable salt thereof, or β-pyridylcarbinol inositol hexanicotinate or a pharmaceutically acceptable salt thereof.

The present teachings include methods of treating, ameliorating, reducing, preventing or reversing age-associated impairment of memory function in a subject in need thereof. The method of treating, ameliorating, reducing, preventing or reversing age-associated impairment of memory function in a subject in need thereof, can comprise administering an effective amount of NMN or a pharmaceutically acceptable salt thereof, and an effective amount of at least one of nicotinic acid, or a pharmaceutically acceptable salt thereof, niceritrol or a pharmaceutically acceptable salt thereof, tocopherol nicotinate or a pharmaceutically acceptable salt thereof, or β-pyridylcarbinol inositol hexanicotinate or a pharmaceutically acceptable salt thereof.

The present teachings include methods of treating, ameliorating, reducing, preventing or reversing age-associated decline in eye function in a subject in need thereof. The method of treating, ameliorating, reducing, preventing or reversing age-associated decline in eye function in a subject in need thereof, can comprise administering an effective amount of NMN or a pharmaceutically acceptable salt thereof, and an effective amount of at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof.

A method of treating age-associated retinal degeneration in a subject in need thereof is provided. The method can comprise administering NMN or a pharmaceutically acceptable salt thereof, and at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof.

A method of treating age-associated retinal degeneration, age-associated decline in eye function, age-associated impairment of memory function, or age-associated loss of insulin sensitivity is provided. The method can comprise administering NMN or a pharmaceutically acceptable salt thereof, and at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof.

A method of treating, ameliorating, preventing, or reversing age-related functional decline is provided. The method can comprise administering NMN or a pharmaceutically acceptable salt thereof, and at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof. Age-related functional decline can comprise loss of appetite, low glucose levels, muscle weakness, sarcopenia, or a combination thereof.

A method of treating, ameliorating, preventing, or reversing diabetes is provided. The method can comprise administering NMN or a pharmaceutically acceptable salt thereof, and at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof. The diabetes can be type I diabetes or type II diabetes.

A method of treating, ameliorating, preventing, or reversing obesity is provided. The method can comprise administering NMN or a pharmaceutically acceptable salt thereof, and at least one of nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof.

A pharmaceutical composition is provided. The pharmaceutical composition can comprise NMN or a pharmaceutically acceptable salt thereof, and an agonist of an NMN transporter. The agonist of an NMN transporter can be nicotinic acid, or a pharmaceutically acceptable salt thereof, niceritrol or a pharmaceutically acceptable salt thereof, tocopherol nicotinate or a pharmaceutically acceptable salt thereof, β-pyridylcarbinol or a pharmaceutically acceptable salt thereof, or inositol hexanicotinate or a pharmaceutically acceptable salt thereof. The agonist of an NMN transporter can be selected from the group consisting of nicotinic acid, niceritrol, tocopherol nicotinate or a pharmaceutically acceptable salt thereof, β-pyridylcarbinol or a pharmaceutically acceptable salt thereof, or inositol hexanicotinate or a pharmaceutically acceptable salt thereof. The NMN transporter can be Slc12a8 polypeptide or a homolog thereof.

A further pharmaceutical composition is provided. The pharmaceutical composition can comprise NMN and an inducer of gene expression of Slc12a8 or a homologue thereof. The Slc12a8 can have an amino acid sequence identified as accession no. NM_134251 (SEQ ID NO: 12); Slc12a8 mouse variant a (SEQ ID NO: 13); Slc12a8 mouse variant b, (SEQ ID NO: 14) or Slc12a8 human (SEQ ID NO: 15).

The present teachings include methods of stimulating NAD+ production in a subject, and methods of increasing NMN uptake into cells in a subject. The subject can be a subject in need of treatment for a disease that involves NMN metabolism, such as, for example, age-related obesity. These methods include administering to a subject in need thereof a nucleic acid comprising a cDNA encoding Slc12a8. The cDNA encoding a Slc12a8 can be a Slc12a8 cDNA of a Slc12a8 mRNA transcript from a mammal such as a human or a rodent such as a mouse or a rat. The nucleic acid can include a lentivirus comprising a cDNA encoding a Slc12a8. The cDNA encoding a Slc12a8 can include the sequence described in GenBank Reference Sequence: NM_134251 (SEQ ID NO: 1) or can have 70% or greater sequence identity with the sequence described in GenBank Reference Sequence: NM_134251 (SEQ ID NO: 1). The lentivirus of the present teachings can be administered to the small intestine in a subject in need of treatment.

The present teachings also include a knock-out mouse comprising a deletion in a Slc12a8 gene. The deletion can be, without limitation, a deletion in exon 4 of the Slc12a8 gene.

The present teachings further include a mammalian cell line comprising a cDNA encoding a Slc12a8 polypeptide, or a cDNA sequence having at least 70% sequence identity with GenBank Reference Sequence: NM_134251 (SEQ ID NO: 1). The cell line can be stably transformed with the cDNA, or transiently transformed with the cDNA. The cDNA can be operably linked to a control sequence such as, for example and without limitation a promoter or an enhancer operably linked to the cDNA.

The mammalian cell line can lack CD73 and/or CD38 activity.

The mammalian cell line can be a mouse cell line, a rat cell line, or a human cell line. The mammalian cell line can be a NIH 3T3 cell line transformed with a cDNA sequence having at least 70% sequence identity with GenBank Reference Sequence: NM_134251 (SEQ ID NO: 1). The transformation can be a stable transformation or a transient transformation.

The present teachings include also methods of enhancing cellular uptake of NMN in a subject in need thereof. These methods include administering a therapeutically effective amount of nicotinic acid or an ester or pharmaceutically acceptable salt thereof. The ester of nicotinic acid can have a structure

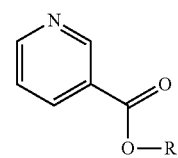

wherein R can be, without limitation, methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, or p-nitrophenyl. R can be H, 2-dimethylaminoethyl, p-chlorophenyl, or p-nitrophenyl. R can be 2-dimethylaminoethyl, p-chlorophenyl, or p-nitrophenyl.

The present teachings also include methods of enhancing cellular uptake of NMN in a subject in need thereof. These methods can include administering a compound or a pharmaceutically acceptable salt thereof, wherein the compound is nicotinic acid, an ester of nicotinic acid, niceritrol, tocopherol nicotinate, β-pyridylcarbinol or inositol hexanicotinate. The administering can comprise administering 50-500 mg per day of nicotinic acid, an ester of nicotinic acid, niceritrol, tocopherol nicotinate, β-pyridylcarbinol or inositol hexanicotinate or a pharmaceutically acceptable salt of any of these compounds. The compound or a pharmaceutically acceptable salt thereof can be administered with a pharmaceutically acceptable excipient.

The present teachings also include methods of treating age-associated loss of insulin sensitivity in a subject in need thereof, methods of treating age-associated loss of insulin secretion in a subject in need thereof, methods of treating age-associated loss of insulin action in a subject in need thereof, methods of treating age-associated loss of insulin action and secretion in a subject in need thereof, methods of treating age-associated impairment of memory function in a subject in need thereof, methods of treating age-associated decline in eye function in a subject in need thereof, and methods of treating age-associated retinal degeneration in a subject in need thereof. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The present teachings also include methods of treating a muscle disease in a subject in need thereof. Muscle diseases which can be treated in accordance with the present teachings include, without limitation, muscle frailty, muscle atrophy, muscle wasting a decrease in muscle strength. Muscle diseases which can be treated in accordance with the present teachings include, without limitation, sarcopenia, dynapenia, cachexia, muscular dystrophy, myotonic disorders, spinal muscular atrophies, and myopathy. The muscular dystrophy can be, for example, Duchenne Muscular Dystrophy, Becker Muscular Dystrophy, Congenital Muscular Dystrophy, Distal Muscular Dystrophy, Emery-Dreifuss Muscular Dystrophy, Facioscapulohumeral Muscular Dystrophy, Limb-Girdle Muscular Dystrophy, or Oculopharyngeal Muscular Dystrophy. The myotonic disorder can be Myotonic Dystrophy, Myotonia Congenita, or Paramyotonia Congenita. The myopathy can be Bethlem myopathy, congenital fibre type disproportion, fibrodysplasia ossificans progressiva, hyper thyroid myopathy, hypo thyroid myopathy, minicore myopathy, multicore myopathy, myotubular myopathy, nemaline myopathy, periodic paralysis, hypokalemic myopathy or hyperkalemic myopathy. The muscle disease can be Acid Maltase Deficiency, Carnitine Deficiency, Carnitine Palmityl Transferase Deficiency, Debrancher Enzyme Deficiency, Lactate Dehydrogenase Deficiency, Mitochondrial Myopathy, Myoadenylate Deaminase Deficiency, Phosphorylase Deficiency, Phosphofructokinase Deficiency, or Phosphoglycerate Kinase Deficiency. The muscle disease can be sarcopenia, dynapenia or cachexia. The muscle disease can be sarcopenia. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The present teachings also include pharmaceutical compositions comprising NMN and an agonist of an NMN transporter. The agonist of an NMN transporter can be, without limitation, nicotinic acid, an ester of nicotinic acid, niceritrol, tocopherol nicotinate, β-pyridylcarbinol or inositol hexanicotinate.

The NMN transporter can be Slc12a8 polypeptide or a homolog thereof.

The present teachings also include methods of preventing age-related functional decline in a subject in need thereof. The age-related functional decline can result from or can be associated with, in non-limiting example, loss of appetite, low glucose levels, muscle weakness, malnutrition, or anorexia of aging. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The present teachings also include methods of preventing age-related functional decline in a subject in need thereof. The age-related functional decline can result from or can be associated with, in non-limiting example, loss of appetite, low glucose levels, muscle weakness, malnutrition, or anorexia of aging. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The present teachings also include methods of treating type 2 diabetes in a subject in need thereof. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The present teachings also include methods of treating obesity in a subject in need thereof. These methods can comprise administering a pharmaceutically effective amount of NMN as well as a compound such as nicotinic acid, an ester of nicotinic acid, niceritrol, tocopherol nicotinate, β-pyridylcarbinol or inositol hexanicotinate, or a pharmaceutically acceptable salt thereof.

The studies presented herein demonstrate that the Slc12a8 gene encodes a novel NMN transporter in mammals. The mRNA expression of the Slc12a8 gene is upregulated in response to NAD+ decline, which, without being limited by theory, allows cells to respond to an urgent demand for NAD+ biosynthesis. The Slc12a8 NMN transporter can be specific to NMN under physiological conditions. Whereas knocking down this gene in cell culture and in the small intestine completely abrogates the fast uptake of NMN, overexpression of its full-length cDNA provides increased NMN transport to cells that otherwise exhibit minimal NMN transport.

Various aspects of the invention are described in additional detail in the sections below.

Methods of Treatment

Various methods of treating an age-associated condition in a subject in need thereof are provided. Typically, the methods comprise administering to the subject a therapeutically effective amount of nicotinamide mononucleotide (NMN) and at least one additional compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof, and wherein the age-associated condition comprises at least one condition selected from the group consisting of loss of insulin sensitivity, loss of insulin secretion, loss of insulin action and secretion, impairment of memory function, decline in eye function, retinal degeneration, functional decline, and combinations of any thereof.

The age-associated condition can comprise loss of insulin sensitivity.

The age-associated condition can comprise loss of insulin secretion.

The age-associated condition can comprise loss of insulin action and secretion.

The age-associated condition can comprise impairment of memory function.

The age-associated condition can comprise decline in eye function.

The age-associated condition can comprise retinal degeneration.

The age-associated condition can comprise functional decline (e.g., loss of appetite, low glucose levels, muscle weakness, malnutrition, anorexia of aging, or a combination of any thereof).

The age-associated condition can comprise any combination of age-associated conditions described herein.

Other methods relate to treating a medical condition in a subject in need thereof. The methods comprise administering to the subject a therapeutically effective amount of nicotinamide mononucleotide (NMN) and at least one compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof, wherein the medical condition comprises at least one selected from the group consisting of a muscle disease, type 2 diabetes, obesity, and combinations of any thereof.

The medical condition can comprise a muscle disease. Where the subject is a subject in need of treatment for a muscle disease, the muscle disease can comprise muscle frailty, muscle atrophy, muscle wasting, a decrease in muscle strength, or a combination of any thereof.

The muscle disease can comprise sarcopenia, dynapenia, cachexia, muscular dystrophy (e.g., Duchenne muscular dystrophy, Becker muscular dystrophy, congenital muscular dystrophy, distal muscular dystrophy, Emery-Dreifuss muscular dystrophy, facioscapulohumeral muscular dystrophy, limb-girdle muscular dystrophy, oculopharyngeal muscular dystrophy, or a combination of any thereof), a myotonic disorder (e.g., myotonic dystrophy, myotonia congenita, paramyotonia congenita, or a combination of any thereof), a spinal muscular atrophy, a myopathy (e.g., Bethlem myopathy, congenital fibre type disproportion, fibrodysplasia ossificans progressiva, hyper thyroid myopathy, hypo thyroid myopathy, minicore myopathy, multicore myopathy, myotubular myopathy, nemaline myopathy, periodic paralysis, hypokalemic myopathy, hyperkalemic myopathy, or a combination of any thereof), or a combination of any thereof.

The muscle disease can comprise acid maltase deficiency, carnitine deficiency, carnitine palmityl transferase deficiency, debrancher enzyme deficiency, lactate dehydrogenase deficiency, mitochondrial myopathy, myoadenylate deaminase deficiency, phosphorylase deficiency, phosphofructokinase deficiency, phosphoglycerate kinase deficiency, or a combination of any thereof.

The muscle disease can be selected from the group consisting of sarcopenia, dynapenia, cachexia, and combinations of any thereof.

The muscle disease can comprise sarcopenia.

The medical condition can comprise type 2 diabetes.

The medical condition can comprise obesity.

The medical condition can comprise any combination of medical conditions described herein.

In the various methods described herein, the at least one additional compound can comprise nicotinic acid, an ester of any thereof, or a pharmaceutically acceptable salt of any thereof.

The ester or pharmaceutically acceptable salt of nicotinic acid can be a compound of structure (I)

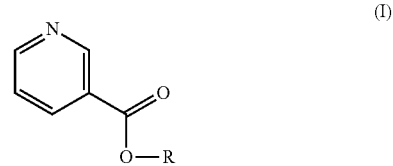

wherein R is selected from the group consisting of methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl (e.g., R can be selected from the group consisting of 2-dimethylaminoethyl, p-chlorophenyl, and p-nitrophenyl).

In the various methods described herein, from about 50 mg to about 500 mg of the at least one additional compound is administered per day to the subject. Also, from about 10 to about 500 mg of NMN can be administered per day to the subject.

Further, the subject can be administered a pharmaceutical composition comprising NMN and the at least one additional compound.

A method of enhancing cellular uptake of NMN in a subject in need thereof is also provided. These method comprises administering to the subject a therapeutically effective amount of a compound selected from the group consisting of nicotinic acid, niceritrol, tocopherol nicotinate, β-pyridylcarbinol, inositol hexanicotinate, esters of any thereof, pharmaceutically acceptable salts of any thereof, and combinations of any thereof.

The compound can comprise nicotinic acid, an ester thereof, or a pharmaceutically acceptable salt thereof. The ester or pharmaceutically acceptable salt of nicotinic acid can be a compound of structure (I)

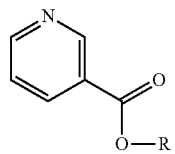

(I)

wherein R is selected from the group consisting of methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl (e.g., R is selected from the group consisting of 2-dimethylaminoethyl, p-chlorophenyl, and p-nitrophenyl).

From about 50 mg to about 500 mg of the compound can be administered per day to the subject.

A method for stimulating NAD+ production and/or increasing NMN uptake into cells in a subject in need thereof is provided. The method comprises administering a therapeutically effective amount of a nucleic acid encoding Slc12a8 to the subject.

The nucleic acid encoding Slc12a8 can comprise a cDNA encoding Slc12a8.

In any of the methods for stimulating NAD+ production and/or increasing NMN uptake into cells in a subject, administering the nucleic acid encoding Slc12a8 can comprise administering a gene therapy vector encoding Slc12a8.

The gene therapy vector can comprise a retrovirus, an adenovirus, an adeno-associated virus, an alphavirus, a herpesvirus, a vaccinia virus, or a combination of any thereof.

For example, the gene therapy vector can comprise a retrovirus.

Where the gene therapy vector comprises a retrovirus, the retrovirus suitably comprises a lentivirus.

In any of methods for stimulating NAD+ production and/or increasing NMN uptake into cells in a subject that comprise administering a cDNA encoding Slc12a8, the cDNA encoding Slc12a8 can comprise a sequence having at least 70% sequence identity with GenBank Reference Sequence: NM_134251 (SEQ ID NO: 1).

The cDNA encoding Slc12a8 can comprise a sequence having at least 75% sequence identity with SEQ ID NO: 1.

The cDNA encoding Slc12a8 can comprise a sequence having at least 80% sequence identity with SEQ ID NO: 1.

The cDNA encoding Slc12a8 can comprise a sequence having at least 85% sequence identity with SEQ ID NO: 1.

The cDNA encoding Slc12a8 can comprise a sequence having at least 90% sequence identity with SEQ ID NO: 1.

The cDNA encoding Slc12a8 can comprise a sequence having at least 95% sequence identity with SEQ ID NO: 1.

The cDNA encoding Slc12a8 can comprise a sequence having at least 99% sequence identity with SEQ ID NO: 1.

The cDNA encoding Slc12a8 can comprise a sequence having 100% sequence identity with SEQ ID NO: 1.

Alternatively or in addition, the cDNA encoding Slc12a8 can comprise any of the Slc12a8 disclosed herein.

In any of methods for stimulating NAD+ production and/or increasing NMN uptake into cells in a subject that comprise administering a therapeutically effective amount of a nucleic acid encoding Slc12a8 to a subject, the method can comprise administering the nucleic acid encoding Slc12a8 to the gastrointestinal tract of the subject. For example, the method can comprise administering the nucleic acid encoding Slc12a8 to the small intestine of the subject.

In any of methods for stimulating NAD+ production and/or increasing NMN uptake into cells in a subject that comprise administering a therapeutically effective amount of a nucleic acid encoding Slc12a8 to a subject, the subject can be a subject in need of treatment for a muscle disease, type 2 diabetes, obesity, an age-associated condition, or a combination of any thereof.

The age-associated condition can be selected from the group consisting of loss of insulin sensitivity, loss of insulin secretion, loss of insulin action and secretion, impairment of memory function, decline in eye function, retinal degeneration, functional decline, obesity, and combinations of any thereof.

The age-associated condition can comprise loss of insulin sensitivity.

The age-associated condition can comprise loss of insulin secretion.

The age-associated condition can comprise loss of insulin action and secretion.

The age-associated condition can comprise impairment of memory function.

The age-associated condition can comprise decline in eye function.

The age-associated condition can comprise retinal degeneration.

The age-associated condition can comprise functional decline (e.g., loss of appetite, low glucose levels, muscle weakness, malnutrition, anorexia of aging, or a combination of any thereof).

The age-associated condition can comprise age-related obesity.

Where the subject is a subject in need of treatment for a muscle disease, the muscle disease can comprise muscle frailty, muscle atrophy, muscle wasting, a decrease in muscle strength, or a combination of any thereof.

The muscle disease can comprise sarcopenia, dynapenia, cachexia, muscular dystrophy (e.g., Duchenne muscular dystrophy, Becker muscular dystrophy, congenital muscular dystrophy, distal muscular dystrophy, Emery-Dreifuss muscular dystrophy, facioscapulohumeral muscular dystrophy, limb-girdle muscular dystrophy, oculopharyngeal muscular dystrophy, or a combination of any thereof), a myotonic disorder (e.g., myotonic dystrophy, myotonia congenita, paramyotonia congenita, or a combination of any thereof), a spinal muscular atrophy, a myopathy (e.g., Bethlem myopathy, congenital fibre type disproportion, fibrodysplasia ossificans progressiva, hyper thyroid myopathy, hypo thyroid myopathy, minicore myopathy, multicore myopathy, myotubular myopathy, nemaline myopathy, periodic paralysis, hypokalemic myopathy, hyperkalemic myopathy, or a combination of any thereof), or a combination of any thereof.

The muscle disease can comprise acid maltase deficiency, carnitine deficiency, carnitine palmityl transferase deficiency, debrancher enzyme deficiency, lactate dehydrogenase deficiency, mitochondrial myopathy, myoadenylate deaminase deficiency, phosphorylase deficiency, phosphofructokinase deficiency, phosphoglycerate kinase deficiency, or a combination of any thereof.

The muscle disease can be selected from the group consisting of sarcopenia, dynapenia, cachexia, and combinations of any thereof.

The muscle disease can comprise sarcopenia.

In any of methods for stimulating NAD+ production and/or increasing NMN uptake into cells in a subject that comprise administering a therapeutically effective amount of a nucleic acid encoding Slc12a8 to a subject, the subject can be a subject in need of treatment for type 2 diabetes.

In any of methods for stimulating NAD+ production and/or increasing NMN uptake into cells in a subject that comprise administering a therapeutically effective amount of a nucleic acid encoding Slc12a8 to a subject, the subject can be a subject in need of treatment for obesity.

In any of the methods described herein, the subject can be a mammal.

For example, the subject can be a mouse or a rat.

The subject can be a human. Where the subject is a human, the human can have an age of at least 30 years, at least 40 years, at least 50 years, at least 60 years, or at least 70 years.

Gene Therapy Vectors

A gene therapy vector is provided. The vector comprises a nucleic acid encoding Slc12a8.

The nucleic acid encoding Slc12a8 can comprise a cDNA encoding Slc12a8.

The vector can comprise a retrovirus, an adenovirus, an adeno-associated virus, an alphavirus, a herpesvirus, a vaccinia virus, or a combination of any thereof.

For example, the gene therapy vector can comprise a retrovirus.

The retrovirus can comprise a lentivirus.

The cDNA encoding Slc12a8 can comprises a sequence having at least 70% sequence identity with GenBank Reference Sequence: NM_134251 (SEQ ID NO: 1).

The cDNA encoding Slc12a8 can comprises a sequence having at least 75% sequence identity with SEQ ID NO: 1.

The cDNA encoding Slc12a8 can comprises a sequence having at least 80% sequence identity with SEQ ID NO: 1.

The cDNA encoding Slc12a8 can comprises a sequence having at least 70% sequence identity with SEQ ID NO: 1.

The cDNA encoding Slc12a8 can comprises a sequence having at least 85% sequence identity with SEQ ID NO: 1.

The cDNA encoding Slc12a8 can comprises a sequence having at least 90% sequence identity with SEQ ID NO: 1.

The cDNA encoding Slc12a8 can comprises a sequence having at least 95% sequence identity with SEQ ID NO: 1.

The cDNA encoding Slc12a8 can comprises a sequence having at least 99% sequence identity with SEQ ID NO: 1.

The cDNA encoding Slc12a8 can comprises a sequence having 100% sequence identity with SEQ ID NO: 1.

Alternatively or in addition, the cDNA encoding Slc12a8 can comprise any of the Slc12a8 disclosed herein.

Non-Human Animals Comprising Mutations in Slc12a8

A non-human animal is provided. The non-human animal comprises an inactivating mutation in a Slc12a8 gene.

The non-human animal suitably comprises a mouse or a rat.

The inactivating mutation in the Slc12a8 gene can comprise a deletion in the Slc12a8 gene, an insertion in the Slc12a8 gene, or a combination thereof.

For example, the inactivating mutation in the Slc12a8 gene can comprise a deletion in a Slc12a8 gene. The deletion can comprise a partial deletion of the Slc12a8 gene or a complete deletion of the Slc12a8 gene.

The deletion can comprise a deletion of exon 4 of the Slc12a8 gene.

The deletion can comprise a deletion of a portion of exon 4 of the Slc12a8 gene.

Mammalian Cells and Mammalian Cell Lines

Mammalian cells and mammalian cell lines are also provided.

A mammalian cell or mammalian cell line is provided. The mammalian cell or mammalian cell line comprises a cDNA encoding a Slc12a8 protein. The cDNA comprises a cDNA encoding SEQ ID NO: 12 (mouse Slc12a8 protein), SEQ ID NO: 13 (mouse Slc12a8 variant A protein), SEQ ID NO: 14 (mouse Slc12a8 variant B protein), or SEQ ID NO: 15 (human Slc12a8 protein).

A further mammalian cell or mammalian cell line is provided. The mammalian cell or mammalian cell line comprises a cDNA encoding a Slc12a8 protein. The cDNA comprises a cDNA encoding a protein having at least 70% with SEQ ID NO: 12, SEQ ID NO: 13, SEQ ID NO: 14, or SEQ ID NO: 15.

The cDNA can comprise a cDNA encoding a protein having at least 75% with SEQ ID NO: 12, SEQ ID NO: 13, SEQ ID NO: 14, or SEQ ID NO: 15.

The cDNA can comprise a cDNA encoding a protein having at least 80% with SEQ ID NO: 12, SEQ ID NO: 13, SEQ ID NO: 14, or SEQ ID NO: 15.

The cDNA can comprise a cDNA encoding a protein having at least 85% with SEQ ID NO: 12, SEQ ID NO: 13, SEQ ID NO: 14, or SEQ ID NO: 15.

The cDNA can comprise a cDNA encoding a protein having at least 90% with SEQ ID NO: 12, SEQ ID NO: 13, SEQ ID NO: 14, or SEQ ID NO: 15.

The cDNA can comprise a cDNA encoding a protein having at least 95% with SEQ ID NO: 12, SEQ ID NO: 13, SEQ ID NO: 14, or SEQ ID NO: 15.

The cDNA can comprise a cDNA encoding a protein having at least 99% with SEQ ID NO: 12, SEQ ID NO: 13, SEQ ID NO: 14, or SEQ ID NO: 15.

Yet another mammalian cell or mammalian cell line is provided. The mammalian cell or mammalian cell line comprises a cDNA encoding a Slc12a8 protein. The cDNA comprises a cDNA sequence having at least 70% sequence identity with GenBank Reference Sequence: NM_134251 (SEQ ID NO: 1) or Slc12a8 human full-length CDNA (SEQ ID NO: 11).

The cDNA can comprise a cDNA sequence having at least 75% sequence identity with SEQ ID NO: 1 or SEQ ID NO: 11.

The cDNA can comprise a cDNA sequence having at least 80% sequence identity with SEQ ID NO: 1 or SEQ ID NO: 11.

The cDNA can comprise a cDNA sequence having at least 85% sequence identity with SEQ ID NO: 1 or SEQ ID NO: 11.

The cDNA can comprise a cDNA sequence having at least 90% sequence identity with SEQ ID NO: 1 or SEQ ID NO: 11.

The cDNA can comprise a cDNA sequence having at least 95% sequence identity with SEQ ID NO: 1 or SEQ ID NO: 11.

The cDNA can comprise a cDNA sequence having at least 99% sequence identity with SEQ ID NO: 1 or SEQ ID NO: 11.

The cDNA can comprise a cDNA sequence having 100% sequence identity with SEQ ID NO: 1 or SEQ ID NO: 11.

For any of the mammalian cell or mammalian cell lines, the mammalian cell or mammalian cell line preferably does not comprise placental-derived cells.

A further mammalian cell or a mammalian cell line is provided. The cell or cell line comprises a cDNA encoding a Slc12a8 protein. The cell or cell line does not comprise placental-derived cells.

The cDNA can encode a mouse Slc12a8 protein or a variant thereof.

The cDNA can encode a human Slc12a8 protein or a variant thereof.

In any of the mammalian cell or mammalian cell lines, the cDNA can comprise a cDNA that encodes SEQ ID NO. 12, SEQ ID NO. 13, SEQ ID NO. 14 or SEQ ID NO. 15.

In any of the mammalian cell or mammalian cell lines, the cell or cell line can further comprise a promoter operably linked to the cDNA.

In any of the mammalian cell or mammalian cell lines, the expression of the Slc12a8 protein is preferably increased as compared to the expression of the Slc12a8 protein in an identical mammalian cell or mammalian cell line that does not comprise the CDNA.

In any of the mammalian cell or mammalian cell lines, the mammalian cell or mammalian cell line can lack detectable CD73 activity, can lack detectable CD38 activity, or can lack both detectable CD73 activity and detectable CD38 activity.

In any of the mammalian cell or mammalian cell lines, the mammalian cell or mammalian cell line preferably exhibit increased NMN uptake.

The mammalian cell can comprise a fibroblast, an intestinal cell, a pancreatic cell, a hepatocyte, an adipocyte, a neuron, or a glial cell.

The mammalian cell line can comprise fibroblasts, intestinal cells, pancreatic cells, hepatocytes, adipocytes, neurons, or glial cells.

The mammalian cell can be an NIH 3T3 cell.

The mammalian cell line can be an NIH 3T3 cell line.

In any of the mammalian cell or mammalian cell lines, the mammalian cell or mammalian cell line can be stably transformed with the cDNA sequence.

In any of the mammalian cell or mammalian cell lines, the mammalian cell or mammalian cell line can be transiently transfected with the cDNA sequence.

In any of the mammalian cell or mammalian cell lines, the cDNA sequence can have at least 70% sequence identity with GenBank Reference Sequence: NM_134251 (SEQ ID NO: 1).

The cDNA sequence can have at least 75% sequence identity with SEQ ID NO: 1.

The cDNA sequence can have at least 80% sequence identity with SEQ ID NO: 1.

The cDNA sequence can have at least 85% sequence identity with SEQ ID NO: 1.

The cDNA sequence can have at least 90% sequence identity with SEQ ID NO: 1.

The cDNA sequence can have at least 95% sequence identity with SEQ ID NO: 1.

The cDNA sequence can have at least 99% sequence identity with SEQ ID NO: 1.

The cDNA sequence can have 100% sequence identity with SEQ ID NO: 1.

Any of the mammalian cells can be a mouse or rat cell.

Any of the mammalian cell lines can be a mouse cell line or a rat cell line.

Any of the mammalian cells can be a human cell.

Any of the mammalian cell lines can be a human cell line.

Drug Screening Methods

Methods for screening candidate compounds in order to identify compounds that modulate (e.g., promote) NMN transport are provided. Such methods can be used, for example, to identify new therapeutic compounds that can be used for the prevention or treatment of diseases or conditions that are ameliorated by promoting uptake of NMN into cells.

A method for screening a candidate compound to identify compounds that modulate NMN transport is provided. The method comprises (a) contacting the candidate compound with a cell that expresses an NMN transporter protein or a proteoliposome comprising an NMN transporter protein; and (b) detecting a change in the expression or activity of the NMN transporter protein in the cell or a change in the activity of the NMN transporter protein in the proteoliposome. A change in the expression or activity of the NMN transporter protein in the cell or a change in the activity of the NMN transporter protein in the proteoliposome following contact with the candidate compound indicates that the candidate compound modulates the transport of NMN.

The NMN transporter protein can comprises a Slc12a8 protein.

The Slc12a8 protein can comprises an amino acid sequence having at least 70% sequence identity with SEQ ID NO: 12 (mouse Slc12a8 protein), SEQ ID NO: 13 (mouse Slc12a8 variant A protein), SEQ ID NO: 14 (mouse Slc12a8 variant B protein), or SEQ ID NO: 15 (human Slc12a8 protein).

The Slc12a8 protein can comprises an amino acid sequence having at least 75% sequence identity with SEQ ID NO: 12, SEQ ID NO: 13, SEQ ID NO: 14, or SEQ ID NO: 15.

The Slc12a8 protein can comprises an amino acid sequence having at least 80% sequence identity with SEQ ID NO: 12, SEQ ID NO: 13, SEQ ID NO: 14, or SEQ ID NO: 15.

The Slc12a8 protein can comprises an amino acid sequence having at least 85% sequence identity with SEQ ID NO: 12, SEQ ID NO: 13, SEQ ID NO: 14, or SEQ ID NO: 15.

The Slc12a8 protein can comprises an amino acid sequence having at least 90% sequence identity with SEQ ID NO: 12, SEQ ID NO: 13, SEQ ID NO: 14, or SEQ ID NO: 15.

The Slc12a8 protein can comprises an amino acid sequence having at least 95% sequence identity with SEQ ID NO: 12, SEQ ID NO: 13, SEQ ID NO: 14, or SEQ ID NO: 15.

The Slc12a8 protein can comprises an amino acid sequence having at least 99% sequence identity with SEQ ID NO: 12, SEQ ID NO: 13, SEQ ID NO: 14, or SEQ ID NO: 15.

The Slc12a8 protein can comprise an amino acid sequence having 100% sequence identity with SEQ ID NO: 12, SEQ ID NO: 13, SEQ ID NO: 14, or SEQ ID NO: 15.

The method can further comprise comparing (i) the expression or activity of the NMN transporter protein in the cell that expresses the NMN transporter protein, following contact with the candidate compound; with (ii) the expression or activity of the NMN transporter protein in a cell that does not express the NMN transporter protein or a cell wherein expression or activity of the NMN protein has been inhibited, following contact with the candidate compound.

The cell that does not express the NMN transporter protein can comprise a cell from a Slc12a8 knockout animal.

The method can further comprise comparing (i) the activity of the NMN transporter protein in the proteoliposome comprising the NMN transporter protein, following contact with the candidate compound; with (ii) the activity of the NMN transporter protein in a proteoliposome that does not comprise the NMN transporter protein or a proteoliposome wherein the activity of the NMN transporter has been inhibited, following contact with the candidate compound.

The proteoliposome that does not comprise the NMN transporter protein can comprise a proteoliposome derived from cells of a Slc12a8 knockout animal.

In any of the methods, the cell can comprise a mammalian fibroblast, intestinal cell, pancreatic cell, liver cell, adipose cell, neuron, or glial cell.

In any of the methods, the proteoliposome can comprise a proteoliposome derived from a mammalian fibroblast, intestinal cell, pancreatic cell, liver cell, adipose cell, neuron, or glial cell.

In any of the methods, the cell can comprise any of the mammalian cells described herein.

In any of the methods, the proteoliposome can comprise a proteoliposome derived from any of the mammalian cells or mammalian cell lines described herein.

In any of the methods, the proteoliposome comprises a proteoliposome derived from a mammalian cell or mammalian cell line comprising a Slc12a8 cDNA.

Pharmaceutical Compositions

A pharmaceutical composition is provided. The pharmaceutical composition comprises NMN and an agonist of an NMN transporter.

The agonist of an NMN transporter can comprise a compound selected from the group consisting of nicotinic acid, niceritrol, tocopherol nicotinate, β-pyridylcarbinol, inositol hexanicotinate, esters thereof, pharmaceutically acceptable salts thereof, and combinations thereof. The NMN transporter can comprise nicotinic acid, an ester of any thereof, or a pharmaceutically acceptable salt of any thereof.

The ester or pharmaceutically acceptable salt of nicotinic acid can be a compound of structure (I)

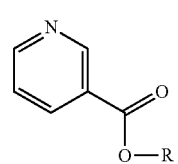

(I)

wherein R is selected from the group consisting of methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl (e.g., R can be selected from the group consisting of 2-dimethylaminoethyl, p-chlorophenyl, and p-nitrophenyl).

Further, the NMN transporter can comprise Slc12a8 polypeptide or a homolog thereof.

A further pharmaceutical composition is provided. The pharmaceutical composition comprises NMN and an inducer of gene expression of Slc12a8 or a homolog thereof.

Having described the invention in detail, it will be apparent that modifications and variations are possible without departing from the scope of the invention defined in the appended claims.

EXAMPLES

Methods

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, NY, 2001; Spector, D. L. et al., Cells: A Laboratory Manual, Cold Spring Harbor Laboratory Press, Cold Spring Harbor, NY, 1998; Nagy, A., Manipulating the Mouse Embryo: A Laboratory Manual (Third Edition), Cold Spring Harbor, NY, 2003 and Harlow, E., Using Antibodies: A Laboratory Manual, Cold Spring Harbor Laboratory Press, Cold Spring Harbor, NY, 1999. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and the appended claims, the singular forms "a", "an" and "the" are intended to include the plural forms as well, unless the context indicates otherwise.

Microarray Analysis. Total RNA was isolated from primary hepatocytes, pancreatic islets, and hippocampal neurospheres, treated with 0.1% DMSO (control) or FK866 (200 nM for primary hepatocytes, and 10 nM for pancreatic islets and hippocampal neurospheres). To determine transcriptional changes induced by FK866 treatment, microarray analyses were conducted using the Illumina Mouse Ref 8 whole genome microarrays (version 2). The background-subtracted raw microarray data were subjected to Z score transformation, and Z ratios were calculated as described previously (Yoshino, J., et al., Cell Metab., 14, 528-536, 2011). All data were analyzed by the R statistical software package.

Cell culture and ex vivo small intestine explant culture. NIH3T3 cells were cultured at 37° C. and 5% CO2 in Dulbecco's modified Eagle's medium (DMEM) supplemented with 10% fetal bovine serum, 100 units/ml penicillin, and 100 µg/ml streptomycin. For Slc12a8 mRNA expression analysis, 2.5×105 cells per well were incubated in 6-well plates with DMEM with 1% FBS containing 0.1% DMSO or 100 nM FK866 or 100 nM FK866 plus 100 µM NMN for 24 h. Small intestines from 3-month old B6 male mice were cut into three segments with duodenum/jejunum/ileum length ratios of 1:3:2 (Wang, H. H., et al., Hepatology 45, 998-1006, 2007). One centimeter of each segment was opened longitudinally, washed once with cold PBS, and incubated for 4 h at 37° C. with 0.1% DMSO or 100 nM FK866 or 100 nM FK866 plus 500 µM NMN in the 1:1 mixture of DMEM and Ham's F-12 medium (Sigma) with 5% FBS and the following additives: 5 µg/ml insulin (Sigma), 20 ng/ml epidermal growth factor (Sigma), 1×B27 supplement (GIBCO), 1 mM Sodium pyruvate (Corning), 100 units/ml penicillin, 100 µg/ml streptomycin, and 2 mM GlutaMAX™ (GIBCO). Cellular and tissue RNA samples were analyzed by quantitative RT-PCR, as described previously (Stein, L. R. & Imai, S., EMBO J., 33, 1321-1340, 2014).

NAD+ and NMN measurements by HPLC. NAD+ and NMN were extracted from cells and tissues and quantified by HPLC, as previously described (Yoshino, J., et al., Cell Metab., 14, 528-536, 2011; Yoshino, J. & Imai, S., Methods Mol. Biol., 1077, 203-215, 2013).

Flow cytometry analysis. 2×106 NIH3T3 cells were incubated in a 10-cm culture dish with DMEM with 1% FBS containing 0.1% DMSO or 100 nM FK866 or 100 nM FK866 plus 100 µM NMN for 48 h at 37° C. and 5% CO2. Cells were then washed once with cold PBS, treated with 0.02% EDTA in PBS, and stained for flow cytometry using a commercially available polyclonal rabbit anti-mouse Slc12a8 antibody (ARP44039, Aviva, CA) at 1:200, a secondary goat anti-rabbit IgG (H+L) conjugated with ALEXA FLUOR® 488 (ThermoFisher Scientific, Waltham, MA, USA) at 1:2000 (Invitrogen), and the survival marker ZOMBIE AQUA™ Dye at 1:400 (Biolegend, San Diego, CA) for 25 min at 4° C. Cells were then washed and analyzed by the GALLIOS™ Flow Cytometer (BeckmanCoulter, Indianapolis, IN). For the intracellular staining, cells were first fixed in 2% PFA for 10 min at room temperature and then permeabilized in saponin-containing buffer for another 10 min at RT. Slc12a8 staining was performed in permeabilization buffer for 25 min at 4° C. Samples were analyzed by the GALLIOS™ Flow Cytometer (BeckmanCoulter, Indianapolis, IN), and data were analyzed using KALUZA™ 1.3 (BeckmanCoulter, Indianapolis, IN). Dead cells were excluded using a ZOMBIE AQUA™ Fixable Viability Kit (Biolegend, San Diego, CA).

Hepatocytes isolation, 5'-nucleotidase activity assay, NMN uptake measurement, and silencing of Slc12a8 and Nrk1 expression. Primary hepatocytes were isolated from 3 month old C57BL/6J (B6) male mice, as previously described (Grimm, A. A., et al., Aging Cell, 10, 305-317, 2011). Cells were cultured overnight in 6-well plates coated with poly-L-lysine at 37° C. and 5% CO2 in Dulbecco's modified Eagle's medium (DMEM) supplemented with 10% fetal bovine serum (FBS), 100 units/ml penicillin, and 100 g/ml streptomycin (pen/strep) before conducting any experiments. Slc12a8 mRNA expression and NAD+ content were evaluated by incubating hepatocytes with 500 nM FK866 or 500 nM FK866 plus 500 µM NMN in DMEM with 1% FBS for 24h. To test whether adenosine-5'-[α,β-methylene]diphosphate (AOPCP) inhibits 5'-nucleotidase activity, 1.5× 105 cells per well were grown in 12-well plates with 500 nM FK866 in DMEM with 1% FBS for 24 h and then incubated in 1.4 ml of Hanks' buffered saline solution with Ca2+ and Mg2+ at pH 7.5 (HBSS, GIBCO) in the presence of 100 µM adenosine monophosphate (AMP) or 100 µM AMP plus 500 µM AOPCP. At different time points (0, 1, 5, 15, and 30 min), 200 µl of each culture supernatant was collected and extracted by adding 28 µl of 70% perchloric acid. The amounts of adenosine produced were determined by HPLC. Elution times for AMP and adenosine were 4.7 and 17.4 min, respectively. To examine cell viability, CELLTITER 96® AQueous One Solution Cell Proliferation Solution (Promega, Madison, WI) was used, and the absorbance was measured at $\lambda$=490 after 4 h incubation. For NMN uptake measurement, 1.5×105 cells per well were grown in 12-well plates with 500 nM FK866 in DMEM with 1% FBS for 24 h and then incubated in 1 ml of HBSS in the presence of 500 µM AOPCP, 20 µM dipyridamole, and 500 nM FK866 or these inhibitors plus 100 µM NMN. At different time points (0, 0.25, 1, 5, 15, and 30 min), cells were washed once with cold HBSS and lysed in cold 10% perchloric acid. Intracellular NMN levels were measured by HPLC as described previously (Yoshino, J., et al., Cell Metab., 14, 528-536, 2011). For gene silencing experiments, 10 µg of ON-TARGETPLUS™ (Dharmacon, Inc, Lafeyette, CO) mouse siRNA (Thermo scientific) specific to Slc12a8 (J-042450-12-0020) or Nrk1 (J 051839-11-0010) or a negative control siRNA (NON-targeting siRNA #1, D-001810-01-20) were electroporated into one million cells per condition, mixed with 100 µl AMAXA® Mouse Hepatocyte NUCLEOFECTOR® Solution (Lonza, Basel, Switzerland), using the NUCLEOFECTOR® program H-26 (Lonza, Basel, Switzerland) following the manufacturer's instructions. The electroporated cells were incubated in the cuvette for 15 min before addition of media. 2.5×105 cells per well were seeded in 6-well plates coated with poly-L-lysine at 37° C. and 5% CO2 in DMEM containing 10% FBS and penicillin-streptomycin for 48 h after electroporation. Those cells were incubated with 500 nM FK866 in DMEM with 1% FBS for 24h. NMN uptake was measured by HPLC after incubating cells in HBSS with 500 µM AOPCP, 20 µM dipyridamole, and 500 nM FK866 or these inhibitors plus 100 µM NMN for 1 min at room temperature. Silencing efficiencies were evaluated by quantitative RT-PCR.

Generation of NIH3T3 Cells Stably Overexpressing the Full-Length Mouse Slc12a8 cDNA.

GenBank Reference Sequence: NM_134251 was used for the sequence. The sequence of GenBank Reference Sequence: NM_134251 is presented as SEQ ID NO: 1 herein.

The coding region of full-length mouse Slc12a8 cDNA (GenBank Reference Sequence: NM_134251) was amplified from mouse liver by PCR using PFUULTRA™ II Fusion HS DNA polymerase (Agilent, Santa Clara, CA) with the following forward and reverse primers containing XhoI sites (Table 1).

TABLE 1

| Primer (SEQ ID NO.) | Sequence |
| --- | --- |
| Slc12a8 forward (SEQ ID NO: 2) | 5'-ATACTCGAGGAGAAT GGCCCAGAGGTCTC-3' |
| Slc12a8 reverse (SEQ ID NO: 3). | 5'-TCAACTACGGAGGGA TGATCGAGCTCATT-3' |

The resulting 2118-bp fragment of full-length Slc12a8 cDNA was digested with XhoI and cloned into pBluescript SK-vector. Slc12a8 cDNA fragment was then subcloned into the mammalian expression vector pCXN2 (Revollo, J. R., et al., J. Biol. Chem., 279, 50754-50763, 2004). The Slc12a8 cDNA sequence in the final vector was confirmed by sequencing. NIH3T3 cells were transfected with 5 µg of pCXN2 carrying the full-length Slc12a8 cDNA (Slc12a8-OE) or empty pCXN2 vector (control) using the SUPERFECT® transfection reagent (QIAGEN, Fredrick, MD) and cultured in DMEM supplemented with 10% FBS, antibiotics, and 300 µg/ml G418 (Invitrogen) for 2 weeks. Resistant cells were pooled, and aliquots were frozen for further experiments. To confirm Slc12a8 protein expression levels in Slc12a8-OE cells, plasma membrane (PM) fractions were prepared from control and Slc12a8-OE NIH3T3 cells, as described previously (Bruzzone, S. et al., FASEB J. 26, 1251-1260, 2012). Briefly, 7.5×107 cells cultured in five 10-cm dishes were used. After 2 washes with ice-cold HES buffer (20 mM HEPES, 1 mM EDTA, and 255 mM sucrose, pH 7.4), cells were collected by scraping in HES buffer (3 ml/dish) containing a protease inhibitor cocktail (Roche) and homogenized by passing 5 times through a 22-gauge needle. All subsequent steps were performed at 4° C. The homogenate was centrifuged (Avanti J-E) at 16,000 g in a JA 25.5 rotor (Beckman-Coulter) for 30 min. The pellet was resuspended in 10 ml HES buffer and centrifuged again at 16,000 g for 30 min. The resulting pellet was resuspended in 10 ml HES buffer and layered on the top of a 10-ml sucrose cushion (38.5% sucrose, 20 mM HEPES, and 1 mM EDTA, pH 7) and centrifuged at 53,000 g for 120 min. The interface containing the PM fraction was removed, resuspended in 10 ml HES buffer, and centrifuged at 40,000×g for 30 min, yielding the PM fraction in the pellet. PM fractions from control or Slc12a8OE cells were lysed with RIPA buffer (150 mM sodium chloride, 1.0% NP-40, 0.25% sodium deoxycholate, 0.1% SDS, 50 mM Tris, pH 7.5, 2 mM EDTA, 1 mM PMSF, 0.5 mM DTT and protease inhibitor cocktail) and boiled for 5 minutes in 1× Laemmli buffer. Western blotting was conducted with polyclonal rabbit anti-mouse Slc12a8 (1:500, ARP44039, Aviva, CA) and anti-Caveolin-1 (1:2000, #3238, Cell Signaling, MA). Band intensity was quantitated on the AMERSHAM HYPERFILM™ ECL (GE Healthcare, Marlborough, MA) using ADOBE® PHOTO-SHOP® (Adobe Systems Inc., San Jose, CA).

NMN uptake analyses with radiolabeled NMN. Control and Slc12a8-OE NIH3T3 cells were harvested by centrifugation (400×g, 5 min), washed once in HBSS, and incubated at 37° C. in HBSS [pH 7.5] (5×106 cells/ml) containing 100 nM 3H-β-Nicotinamide mononucleotide (9 Ci/mmol; Moravek Biochemicals, CA) and unlabeled NMN to make the final concentration 25 μM. At the designated time points (1, 3, 5 and 10 minutes), aliquots of the cells (100 μl) were collected and placed in 1.5-ml microcentrifuge tubes containing silicone-mineral oil (density, 1.015; Sigma-Aldrich) on the top of 2 M potassium hydroxide solution, followed by centrifugation at 16,000×g for 30s. Cells were separated from the buffer and pelleted through the silicone-mineral oil layer. The radioactivity in these cell pellets was determined by a liquid scintillation counter. For calculating Km and Vmax, the same conditions were used as described above, but with various total concentrations of NMN, ranging from 1 μM to 100 μM. At the 4-min time point, 100 μl of cell suspension was collected and pelleted in the same way described above. The radioactivity in cell pellets was determined by a liquid scintillation counter. The radioactivity measured in control NIH3T3 cells was subtracted to calculate Slc12a8-specific NMN uptake in Slc12a8-OE NIH3T3 cells.

Proteoliposome experiments. Proteoliposome preparation was carried out as previously described (Bruzzone, S., et al., FASEB J., 15, 10-12, 2001). Briefly, 2×107 control or Slc12a8-OE NIH3T3 cells were resuspended in 1 ml of lysis buffer (10 mM Tris-HCl, pH 8.3, 150 mM NaCl, 0.3 M sucrose, protease inhibitor cocktail) and disrupted using a homogenizer. The lysate was centrifuged for 10 min at 3,000×g, and the supernatant was collected and centrifuged for 15 min at 100,000×g. The membrane proteins were solubilized with buffer A (10 mM Tris-HCl, pH 8.3, containing 150 mM NaCl and 0.5% n-octyl β-glucopyranoside). Separately, total lipids were extracted from hemoglobin-free erythrocyte membranes (ghosts) as described previously (Franco, L., et al., FASEB J., 12, 1507-1520, 1998). Total lipids from human erythrocyte membranes (3 mg) were dried and resuspended with 600 μl of solubilized membrane proteins (at approximately 0.7 mg/ml protein concentration). The resulting emulsions were sonicated in ice for 1 min and dialyzed against 5 liters of buffer A without n-octyl-β-glucopyranoside (dialysis buffer) for 24 h at 4° C. Proteoliposomes were recovered, centrifuged for 15 min at 100,000×g, resuspended in 900 μl dialysis buffer and passed 5 times through a 30-gauge needle.

To examine the Na+-dependency of Slc12a8, NaCl was replaced with 150 mM LiCl. All steps were carried out at 4° C. Proteoliposomes (30 μl in triplicate for each condition) were incubated for 2, 5 or 10 min at 25° C. in the presence of 105 cpm/ml 3H-β-NMN (specific activity, 9.1 Ci/mmole) with or without label-free nucleotides (NMN, NR, NAD, AMP; NAM or NaMN). At the end of incubations, samples were filtered on a glass fiber paper. Filters were washed with 3 ml of dialysis buffer, dried, and counted for radioactivity.

In vivo Slc12a8 knockdown experiment. To generate shRNA-expressing lentiviral constructs, 56-bp double-stranded oligonucleotides, each of which contains a sense target sequence, a microRNA-based loop sequence (CTTCCTGTCA; SEQ ID NO: 4), an antisense sequence, a termination sequence of four thymidines, and appropriate restriction enzyme sites at both ends, were generated for mouse Slc12a8 and firefly luciferase (fLuc) and cloned into the U6-PGK-GFP vector provided by the Viral Vectors Core at Washington University School of Medicine. The sense Slc12a8 sequence is '5-GCCTAGAGT-GAACAGAGAAGA-3' (SEQ ID NO: 5). Lentiviruses were produced as previously described (Satoh, A. et al., Cell Metab., 18, 416-430, 2013). Knockdown efficiency was tested using primary intestinal cultures (Sato, T. & Clevers, H., Methods Mol. Biol. 945, 319-328, 2013). Large-scale lentivirus production was carried on by the Viral Vectors Core at the Hope Center for Neurological Disorders at Washington University. Three-month old C57BL/6J male mice (Jackson Laboratories) orally received (by gavage) fLuc or Slc12a8 shRNA lentivirus with a titer of 5×106 transduction units after an overnight fast for two consecutive days. After 6 days, mice that had received fLuc or Slc12a8 shRNA lentivirus were fasted overnight, given a gavage of NMN (500 mg/kg) or PBS. Blood was collected from the tail vein at 0, 5 and 60 min following gavage administration, and then plasma was separated by centrifugation. Tissue samples were then collected at 60 minutes following gavage administration. Plasma NMN and tissue NAD+ levels were measured, as described previously (Yoshino, J., et al., Cell Metab., 14, 528-536, 2011; Grimm, A. A., et al., Aging Cell, 10, 305-317, 2011).

Generation of antibodies against mouse Slc12a8. Two different polyclonal rabbit antisera were produced against a synthetized N-terminal peptide (AQR-SPQELFHEAAQQGC; SEQ ID NO: 6) of mouse Slc12a8 (Covance, Denver, PA). The Slc12a8-specific antibody was affinity-purified from one of these antisera. The antiserum or the affinity-purified antibody against the Slc12a8 N-terminal peptide were used for Western blotting at 1:500 dilution.

Generation of the whole-body Slc12a8 knockout mice. Whole-body Slc12a8 knockout (Slc12a8KO) mice were generated with the CRISPR-CAS9 technology by the Transgenic Vectors Core of Washington University. CRISPR gRNAs were designed to flank exon 4 of the Slc12a8 gene. gRNA sequences were as follows: 5' gRNA; 5'-AGTG-CATGTATAGACGTATG-3' (SEQ ID NO: 7) and 3' gRNA; 5'-CCTCACAAATATTTACAGGC-3' (SEQ ID NO: 8). gRNAs were obtained as gBlocks (IDT). Cleavage activity was assessed by transfecting N2A cells with gBlock and Cas9 plasmid (addgene #42230) using XTREMEGENE™ HP (Roche, Basel, Switzerland). Cleavage activity was determined by T7E1 assay using standard methods. gRNA was in vitro transcribed using the T7 MEGASHORT-SCRIPT™ Kit (Ambion, Waltham, MA, USA). Cas9 RNA was in vitro transcribed using the MMESSAGE MMA-CHINE® T7 Ultra Kit (Ambion, Waltham, MA). All RNA were purified using MEGACLEAR® Columns (Ambion, Waltham, MA). RNA was microinjected into C57BL/6J× CBA hybrid zygotes at a concentration of 50 ng/μl Cas9, 25 ng/μl gRNA, and 100 ng/μl ssODN in the Washington University Mouse Genetic Core Facility. Whole-body knockout alleles were detected by PCR across the cleavage site and confirmed by sequencing. One heterozygous founder was established, and the mice were backcrossed to wild-type C57BL/6J mice (Jackson Laboratories) for 5 generations before analysis. Slc12a8-deficient heterozygous mice were crossed to generate homozygous Slc12a8KO mice. Wild-type littermates were used as controls.

Production of 18O-D-NMN. 18O nicotinamide was prepared from the hydrolysis of cyanopyridine in 18O water (Kolodziejska-Huben, M., et al., J. Label. Compd. Radiopharm. 45, 1005-1010, 2002). 1,2-2H,3,5-tetraacetate was synthesized from D-[2-2H]-ribose (purchased from Omicron Biochemicals; Chatterjee, A., et al., Angew. Chem. Int. Ed. Engl. 49, 8653-8656, 2010). 18O-2H labelled nicotinamide riboside was synthesized from 18O-nicotinamide and D-ribofuranose 1,2-2H,3,5-tetraacetate (Fouquerel, E., et al., Cell Rep., 8, 1819-1831, 2014). 18O-2H nicotinamide mononucleotide (18O-D-NMN) was synthesized from 18O-2H nicotinamide riboside, as described previously (Mills, K. F. et al., Cell Metab., 24, 795-806, 2016).

Isotopic tracing experiment. Seven-to-eight month-old Slc12a8KO mice and their wild-type littermates were orally administered 500 mg/kg 18O-D-NMN or PBS after an overnight fast. The jejunum and ileum were collected at 10 min after oral gavage. A 1:1 mixture of reagent-grade methanol and water (4° C.) were added to the frozen tissue (60 µL/mg tissue). After sonication, extracts were centrifuged at 12,000×g for 15 min at 4° C. Chloroform was added to the extracts at a ratio of 1:1 (v/v), thoroughly shaken for 30s, and centrifuged at 12,000×g for 10 min at 4° C. The upper phase (methanol and water) was separated from the lower (organic) phase and lyophilized by speed vacuum at room temperature, reconstituted with 5 mM ammonium formate and centrifuged at 12,000×g for 10 min. Serial dilutions of NMN and 18O-D-NMN at concentrations ranging 128-1000 nmol/L in 5 mM ammonium formate were used for calibration. Liquid chromatography was performed by HPLC (1290; Agilent) with ATLANTIS® T3 (LC 2.1× 150 mm, 3 mm; Waters, Millford, MA) at a flow rate of 0.15 ml/min with 5 mM ammonium formate for mobile phase A and 100% methanol for mobile phase B. Metabolites were eluted with gradients of 0-10 min, 0-70% B; 10-15 min, 70% B; 16-20 min, 0% B. The metabolites were analyzed with a Triple Quadrupole mass spectrometer (6470; Agilent) under positive ESI multiple reaction monitoring (MRM) using parameters for NMN (335>123) and 18O-D-NMN (338>125). Fragmentation, collision, and post acceleration voltages were 135, 8, 7 for NMN. NMN and 18O-D-NMN peaks were identified using the MassHunter quantitative analysis tool (Agilent).

Animal experimentation. All mice were group-housed in a barrier facility with 12-hr light/12-hr dark cycles. Mice were maintained ad libitum on a standard chow diet (LabDiet 5053; LabDiet, St. Louis, MO). Measurements of food intake and fed and fasted glucose, triglyceride, free fatty acids, and insulin levels were conducted, as previously described (Yoshino, J., et al., Cell Metab., 14, 528-536, 2011; Mills, K. F. et al., Cell Metab., 24, 795-806, 2016; Yoon, M. J., et al., Cell Metab., 21, 706-717, 2015). Feces were collected between 9 and 10 am from Slc12a8KO mice and their wild-type littermates and allowed to dry at 55° C. overnight before weighing. The total fecal fat was extracted with a chloroform/methanol mixture (2:1, vol/vol) (Sigma, St. Louis, MO), as described previously (Folch, J., et al., J. Biol. Chem., 226, 497-509, 1957). One milliliter of the organic phase was transferred into a preweighed tube, vacuum dried, and reweighed to determine lipid mass. The percentage of lipid content was normalized to the starting mass (g) of extracted feces. Tissues from Slc12a8KO mice and their wild-type littermates at 8-10 months of age were collected at 9 am or at 9 µm, and NAD+ levels were determined by HPLC. Body composition was determined using a whole-body NMR instrument (EchoMRI®, Echo Medical Systems LLC, Waco, TX). Indirect calorimetry and locomotor activity were conducted by the PhenoMaster system (TSE Systems, MO). All animal studies were approved by the Washington University Animal Studies Committee and were in accordance with NIH guidelines.

Plasma GLP-2 measurement. Blood was collected after 24 h fasting (from 9 am to 9 am) and after 6 h refeeding (from 10 am to 4 pm) from tail veins of 7-9 month-old Slc12a8KO mice and their control wild-type littermates using EDTA-coated microvette tubes. Blood was immediately chilled on ice, centrifuged at 5,000×g and 4° C., and plasma samples were stored at −80° C. Plasma GLP-2 levels were measured by Mouse GLP-2 ELISA Kit (Alpco, Salem, NH) following the manufacturer's instruction.

GLP-1 measurement in plasma and in supernatants of ex vivo small intestine explant cultures. Blood was collected after 6 h refeeding (from 10 am to 4 pm) following 24 h fasting (from 9 am to 9 am) from tail veins of 2- or 24-month-old female Slc12a8 knockdown mice and their controls using EDTA-coated tubes. Blood was immediately chilled on ice, centrifuged at 5,000×g at 4° C., and plasma samples were stored at −80° C. Small intestines from gut-specific Slc12a8 knockdown female mice or 12-month-old Slc12a8KO female mice were cut into three segments of the duodenum, jejunum, and ileum with length ratios of 1:3:2 (Wang, H. H., et al., Hepatology, 2007, 45, 998-1006). One centimeter of ileum or colon was opened longitudinally, washed once with cold PBS, and incubated for 2 h at 37° C. in 500 µl of DMEM (GIBCO, secretion media) without nicotinamide and glucose and with 0.25% fatty acid free albumin bovine serum (Sigma, St. Louis, MO). For experiments with Sirt1 and Sirt6 inhibitors, the ilea from 24-month-old female B6 mice were pre-incubated for 2 h at 37° C. in 500 µl of secretion media contending 0.2% DMSO (vehicle), 20 µM EX527 (Cayman chemical, MI) or 20 µM STK665401 (ChemDiv, cat #8018-9378; Sociali, G. et al., Eur. J. Med. Chem., 2015, 102, 530-539). After pre-incubation, media were replaced, and ex vivo ileal explants were incubated with the same chemicals for 2 h at 37° C. At the end of the incubation in a humidified incubator (95% 02, 5% v/v CO2), media were collected, centrifuged at 800 g for 5 minutes at 4° C. to remove any floating debris, and frozen at −80° C. for subsequent GLP-1 measurements. GLP-1 levels in plasma and media were measured by GLP-1 Total ELISA Kit (EMD Millipore, MO) following the manufacturer's instruction. GLP-1 values were normalized by total protein content analyzed by Bradford assay.

Laser-microdissection. Each hypothalamic nucleus was microdissected, and total RNA was extracted and analyzed by quantitative RT-PCR, as previously described (Satoh, A. et al., Cell Metab., 18, 416-430, 2013).

Statistical Analyses. Differences between two groups were assessed using the Student's t test unless otherwise indicated. Comparisons among several groups were performed using one-way ANOVA with various post hoc tests indicated in the examples. Wilcoxon matched-pairs signed ranks test was used to compare differences in oxygen consumption, energy expenditure, respiratory exchange ratio, and total locomotor activity. For comparisons, p values <0.05 were considered statistically significant. GraphPad Prism (Version 7) was used to conduct statistical analyses. All values are presented as mean±SEM. *p<0.05, p<0.01, *p<0.001, ****p<0.0001 unless otherwise specified.

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates identification of a NMN transporter gene.

When NAMPT-mediated NAD+ biosynthesis was inhibited by FK866, a potent NAMPT inhibitor, in various types of primary cells, co-administration of NMN always produced higher NAD+ increases, compared to those induced by NMN in the absence of FK866 (Revollo, J. R. et al., Cell Metab., 6, 363-375, 2007; Stein, L. R. & Imai, S., EMBO J., 33, 1321-1340 2014; Yoshino, J., et al., Cell Metab., 14, 528-536, 2011). The present investigators conducted gene expression profiling in FK866-treated primary mouse hepatocytes, pancreatic islets, and hippocampal neurospheres, searching for genes commonly upregulated in these three primary cultures. Searches were focused on genes that encode transporters or transmembrane proteins and found only one gene that fit these criteria and had an unknown function. This gene, Slc12a8, exhibited a Z ratio of 2.06, 1.69, and 4.91 in primary hepatocytes, islets, and neurospheres, respectively (FIG. 1). Slc12a8 was identified in the section of the Venn diagram in FIG. 1 indicated by an arrow. The Z ratios and p values for Slc12a8 in each cell type are shown in FIG. 1. The Slc12a8 gene belongs to the SLC12 gene family of the electroneutral cation-chloride-coupled co-transporters, and the function of the protein encoded by this gene remains unknown (Hebert, S. C., et al., Pflugers Arch. 447, 580-593, 2004).

Example 2

This example illustrates differential expression of Slc12a8 in B6 mice.

Figure 2:
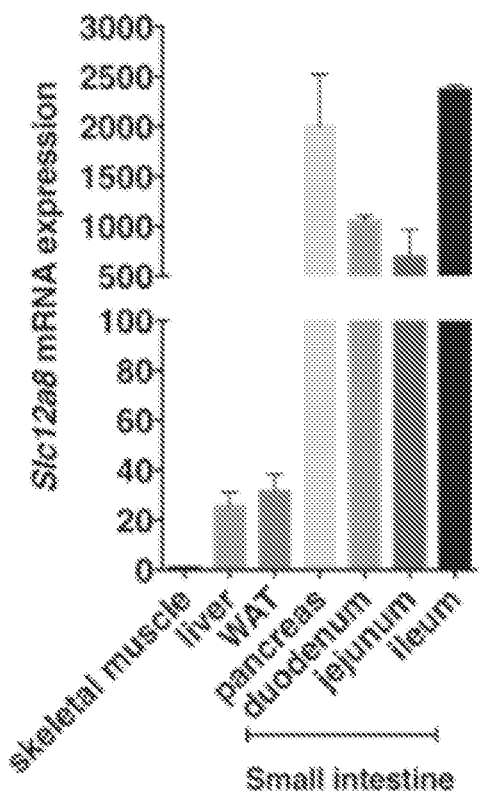
FIG. 2 illustrates Slc12a8 mRNA expression in different tissues from B6 male mice at 3 months of age.
Figure 3:
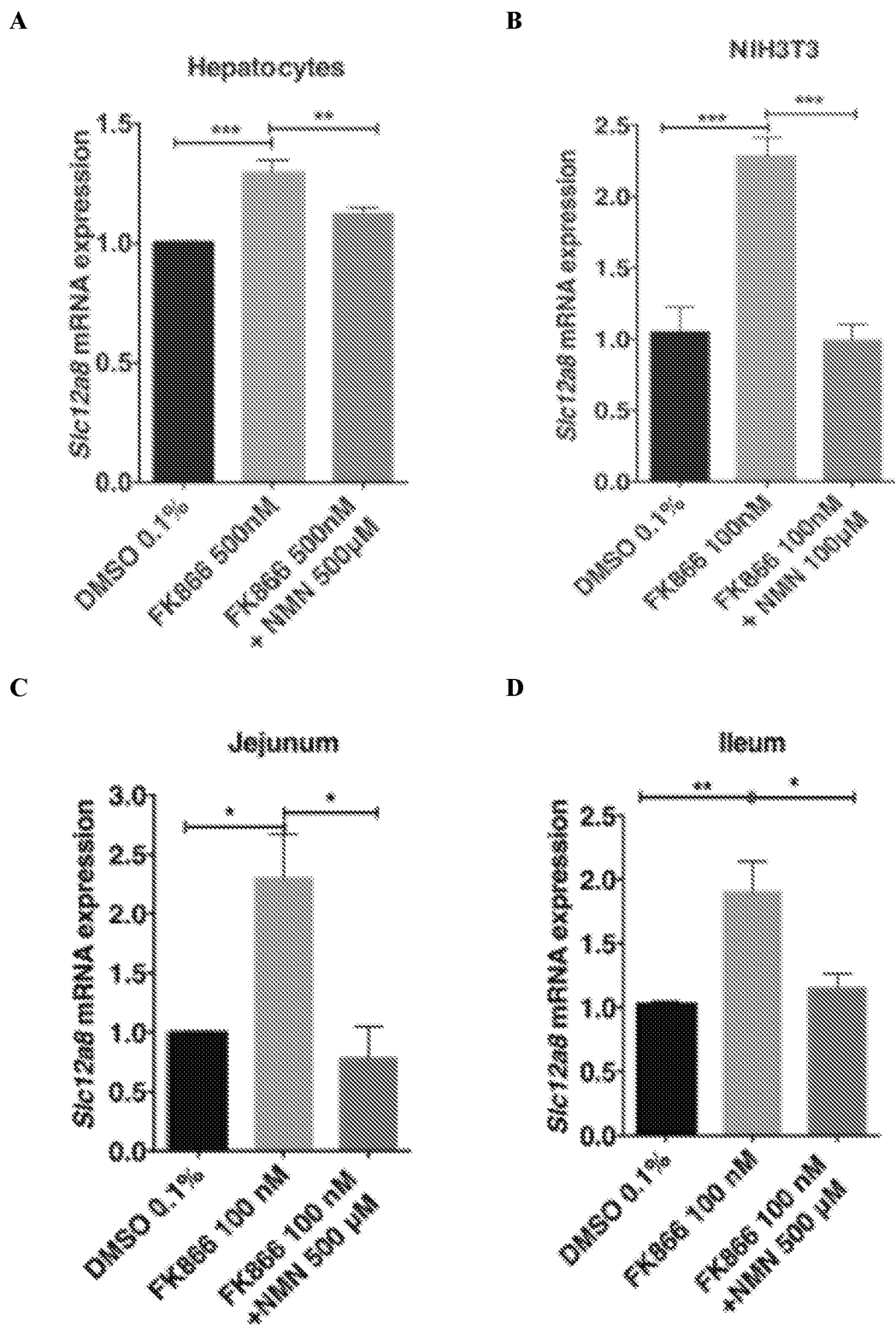
FIG. 3 illustrates Slc12a8 mRNA expression changes in primary mouse hepatocytes, NIH3T3 fibroblasts, and ex vivo explants of jejunum and ileum treated with 0.1% DMSO, FK866 alone or FK866 plus NMN.
Figure 4:
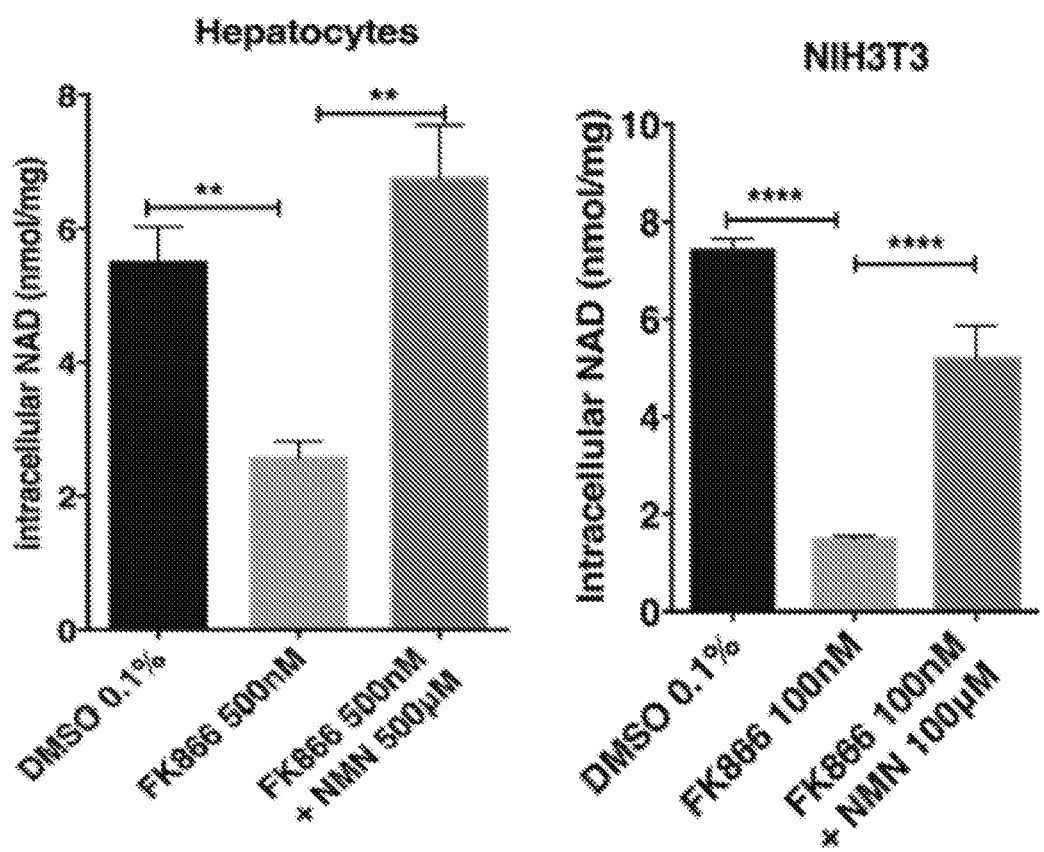
FIG. 4 illustrates intracellular NAD+ content in primary mouse hepatocytes and NIH3T3 fibroblasts treated with DMSO, FK866 alone, and FK866 plus NMN.
Figure 5:
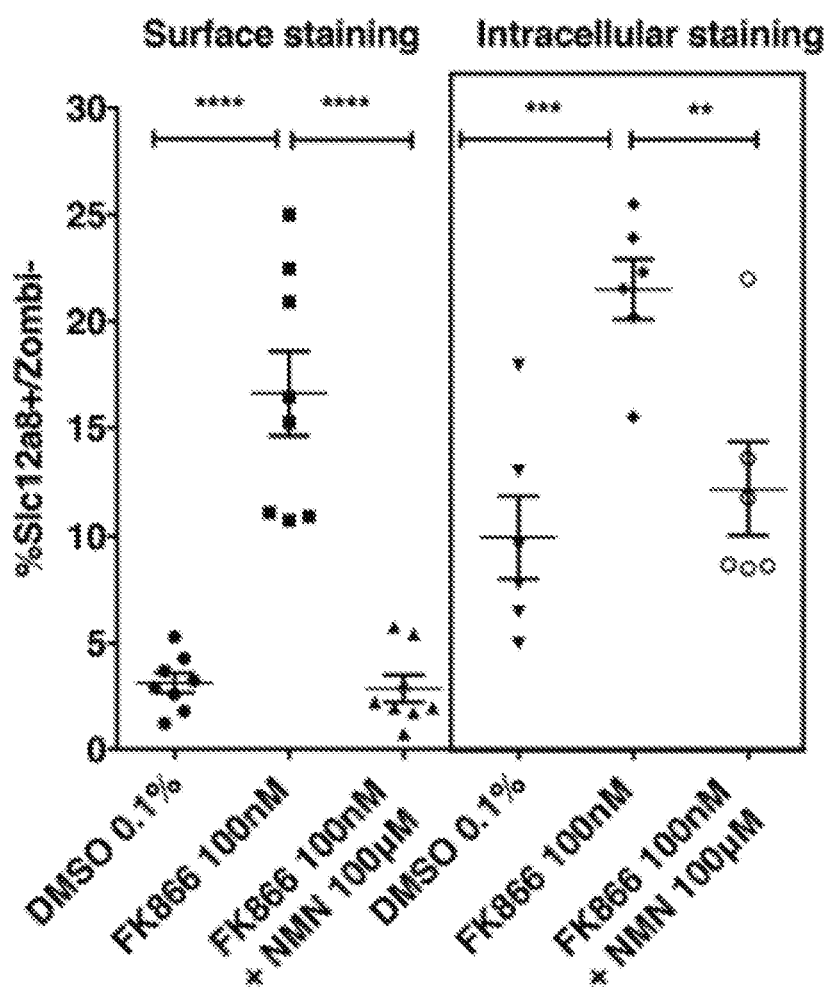
FIG. 5 illustrates flow cytometry data of surface and intracellular Slc12a8 protein expression levels were measured in NIH3T3 cells treated with FK866 and FK866 plus NMN for 48 h.

FIG. 2 illustrates that Slc12a8 is highly expressed in the small intestine and pancreas and moderately in the liver and white adipose tissue of B6 male mice at 3 months of age (n=3 mice). Further Slc12a8 mRNA expression changes in were observed in primary mouse hepatocytes and are illustrated in FIG. 3; (n=4 mice), NIH3T3 fibroblasts (n=4), and ex vivo explants of jejunum and ileum (n=4 mice for DMSO and FK866 alone; n=3 mice for FK866 plus NMN) treated with 0.1% DMSO, FK866 alone or FK866 plus NMN (24 h for cells, and 4 h for explants; analyzed using ANOVA with Tukey's test). Slc12a8 expression was induced significantly in mouse primary hepatocytes, mouse NIH3T3 fibroblasts, and ex vivo explants of jejunum and ileum when treated with FK866, whereas this induction was suppressed by addition of NMN (FIG. 3-5). FIG. 4 illustrates intracellular NAD+ content in primary mouse hepatocytes and NIH3T3 fibroblasts treated with DMSO, FK866 alone, and FK866 plus NMN. Cells were treated with these compounds for 24 h (n=4 mice for hepatocytes treated with DMSO and FK866, and n=3 mice for hepatocytes treated with FK866 and NMN; n=6 for NIH3T3 cells; analyzed using ANOVA with Tukey's test). FIG. 5 illustrates surface and intracellular Slc12a8 protein expression levels were measured by flow cytometry analysis in NIH3T3 cells treated with FK866 or FK866 plus NMN for 48h. Percentage of positive NIH3T3 cells for Slc12a8 staining (Slc12a8+) was calculated among cells negatively selected for a marker of apoptosis (Zombi−) (n=8 for surface staining, and n=5 for intracellular staining; analyzed by unpaired t-test).

Example 3

This example illustrates the effects of Slc12a8 on the kinetics of NMN uptake.

The kinetics of NMN uptake in mouse primary hepatocytes were determined. The extracellular degradation of NMN to NR by CD73 was inhibited with AOPCP (adenosine-5'-[α,β-methylene]diphosphate). The uptake of NR into cells through nucleoside transporters was inhibited with dipyridamole, and the intracellular NMN synthesis by NAMPT was inhibited with FK866. Intact primary hepatocytes were incubated with AMP or AMP plus AOPCP. The generation of extracellular adenosine was measured at different time points (0, 1, 5, 15, and 30 min) by HPLC. AOPCP inhibits 5'-nucleotidase activity by 97%. A cocktail of AOPCP, dipyridamole, and FK866 did not affect cell viability up to 30 min (data not shown).

Figure 6:
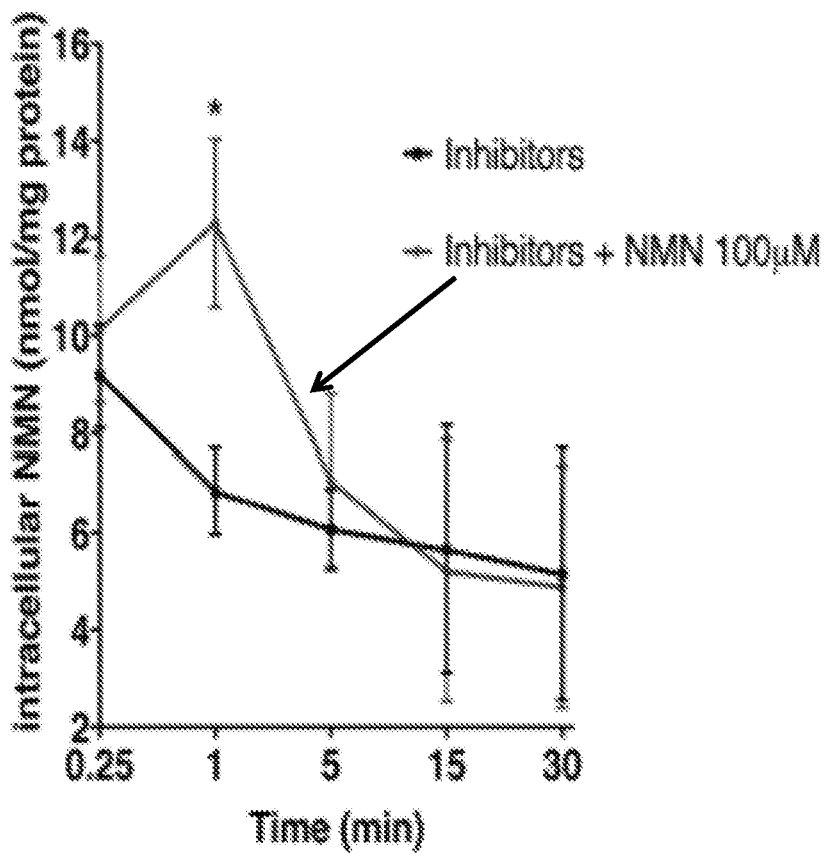
FIG. 6 illustrates a time course of exogenous NMN uptake in primary mouse hepatocytes treated with NMN pathway inhibitors detailed infra.

Primary mouse hepatocytes were pretreated with 500 nM FK866 for 24 h and then incubated with a cocktail of 20 µM dipyridamole, 500 µM AOPCP, and 500 nM FK866, with or without 100 µM NMN. NMN was measured by HPLC (n=4 mice, except for 3 data sets for 15 and 30 minute time points for inhibitors only; analyzed using ANOVA with Sidak's test). This treatment caused intracellular NMN levels to significantly increase at the 1 min time point compared to the control in mouse primary hepatocytes (FIG. 6).

Example 4

This example illustrates the effect of reduced Slc12a8 and Nrk1 mRNA on NMN uptake.

Figure 7:
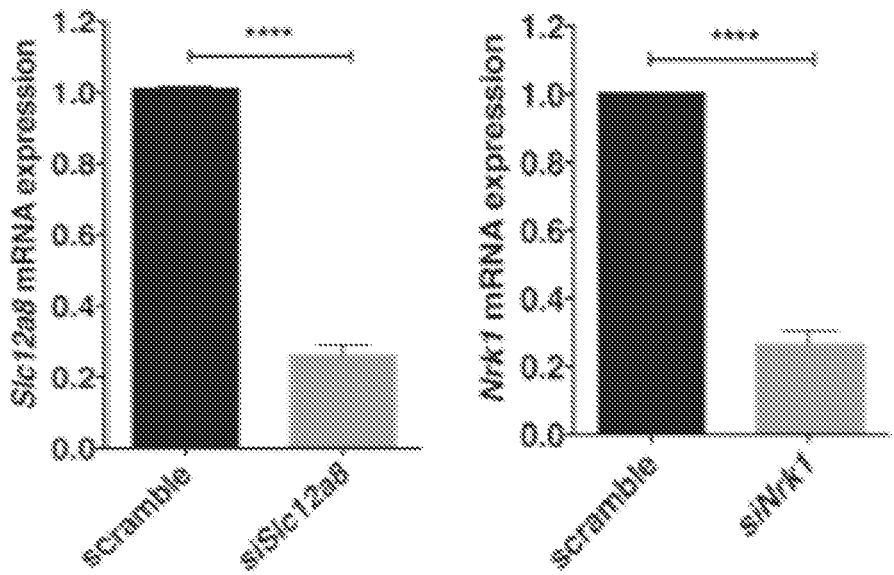
FIG. 7 illustrates the knockdown efficiencies of Slc12a8 and Nrk1 mRNA silencing in primary mouse hepatocytes.
Figure 8:
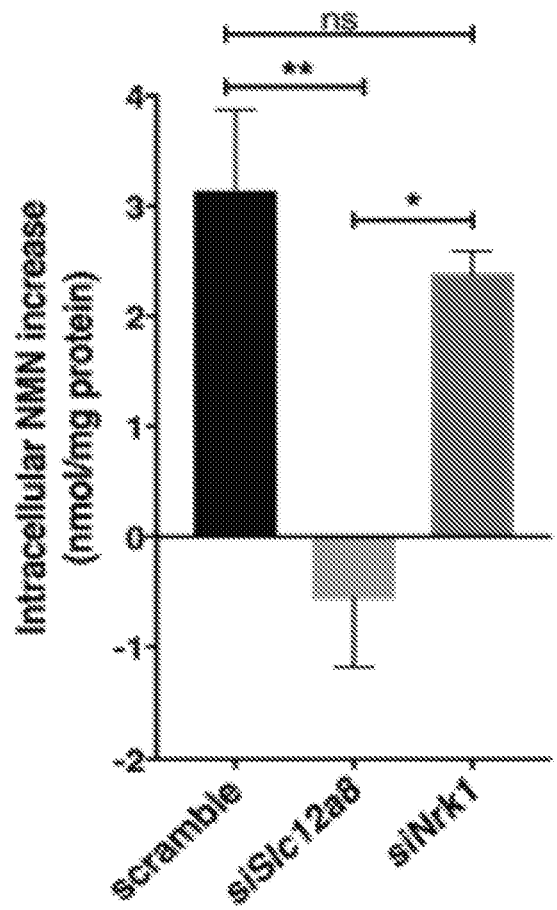
FIG. 8 illustrates intracellular NMN content of cells subjected to Slc12a8 and Nrk1 mRNA silencing as measured by HPLC.

To measure the knockdown efficiencies of Slc12a8 and Nrk1 mRNA in primary mouse hepatocytes, cells were treated with scramble and Slc12a8 or Nrk1 siRNA for 72 h (n=5 mice for Slc12a8 silencing and n=3 for Nrk1 silencing; analyzed by unpaired 700 t-test). Without being limited by theory, these conditions knocked down expression of Slc12a8 and Nrk1, a major NR kinase that converts NR to NMN intracellularly (Belenky, P., et al., Cell, 129, 473-484, 2007). Primary hepatocytes treated with scramble, Slc12a8, and Nrk1 siRNA were assayed at 1 min after addition of 100 µM NMN via HPLC. Culture conditions were the same as described in Example 3 (n=5 mice for Slc12a8 silencing and n=3 for Nrk1 silencing; analyzed by ANOVA with Tukey's test). The knockdown efficiencies for both genes are approximately 80% (FIG. 7). The fast uptake of NMN was completely abrogated in Slc12a8-knockdown hepatocytes, whereas no significant reduction in NMN uptake was observed in Nrk1-knockdown hepatocytes (FIG. 8); these data indicate that Slc12a8 is necessary for the fast uptake of NMN in primary hepatocytes, and the observed increase in intracellular NMN is not due to the conversion of NR or nicotinamide into NMN.

Example 5

This example illustrates overexpression of the full-length mouse Slc12a8 cDNA in mouse NIH3T3 cells.

Figure 9:
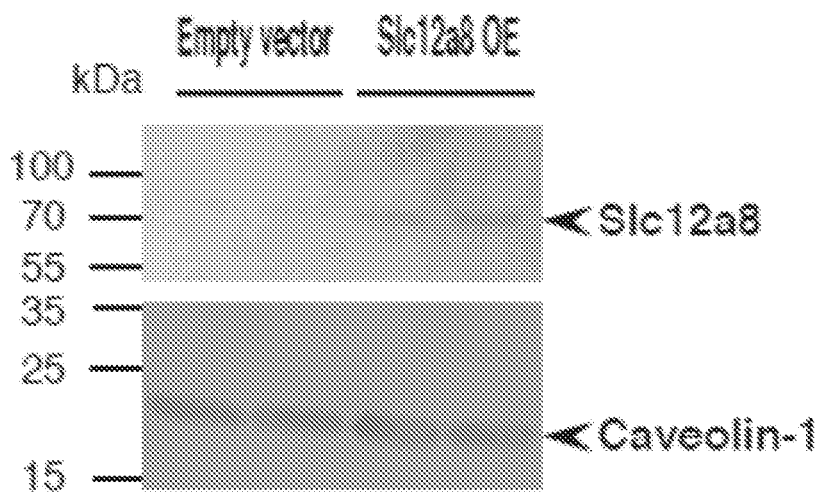
FIG. 9 illustrates Slc12a8 protein expression revealed by SDS-PAGE of plasma membrane fractions from control and Slc12a8-OE NIH3T3 cells.
Figure 10:
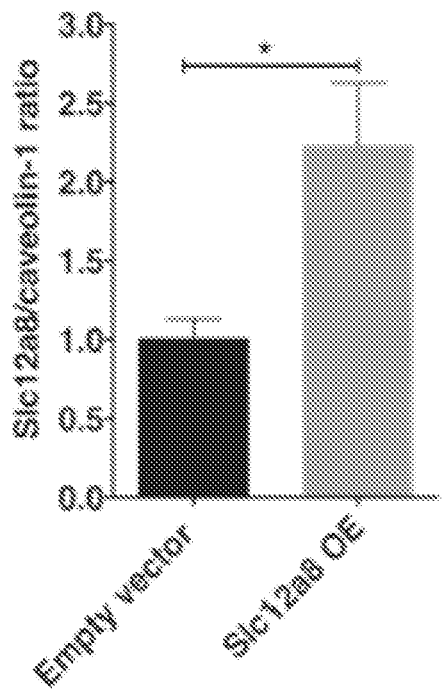
FIG. 10 illustrates Slc12a8 protein levels normalized to caveolin-1 protein levels from control and Slc12a8-OE NIH3T3 cells.

The NIH3T3 cell line was selected because it does not have any detectable extracellular activities of CD73 (converting NMN to NR) and CD38 (degrading NMN to nicotinamide and phosphoribose) and also has very weak NMN uptake activity. Full-length mouse Slc12a8 cDNA was transfected into cells as described in methods, and expression of Slc12a8 protein was assayed. FIG. 9 illustrates Slc12a8 protein expression in plasma membrane fractions from control and Slc12a8-OE NIH3T3 cells. FIG. 10 illustrates Slc12a8 protein levels normalized to caveolin-1 protein levels for each cell line (right panel; n=3, analyzed by unpaired t-test). Slc12a8 protein levels were significantly increased ~2.2-fold in Slc12a8-overexpressing NIH3T3 (Slc12a8-OE) cells.

Example 6

This example illustrates the kinetics of NMN uptake using 3H-labeled NMN in Slc12a8-OE and control cells.

Figure 11:
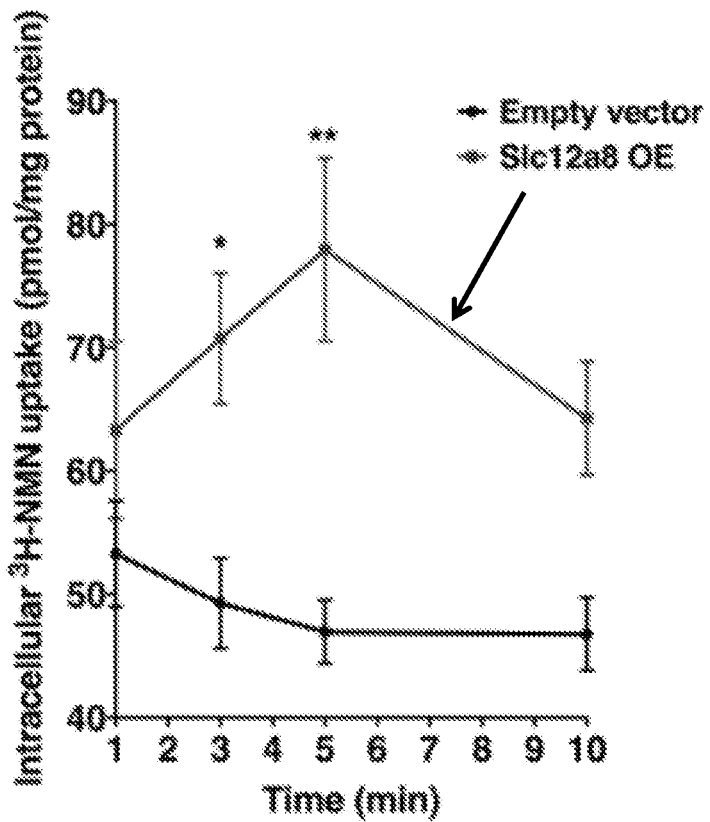
FIG. 11 illustrates intracellular uptake of $^3$H-NMN in Slc12a8 overexpressing and control NIH3T3 cells.
Figure 12:
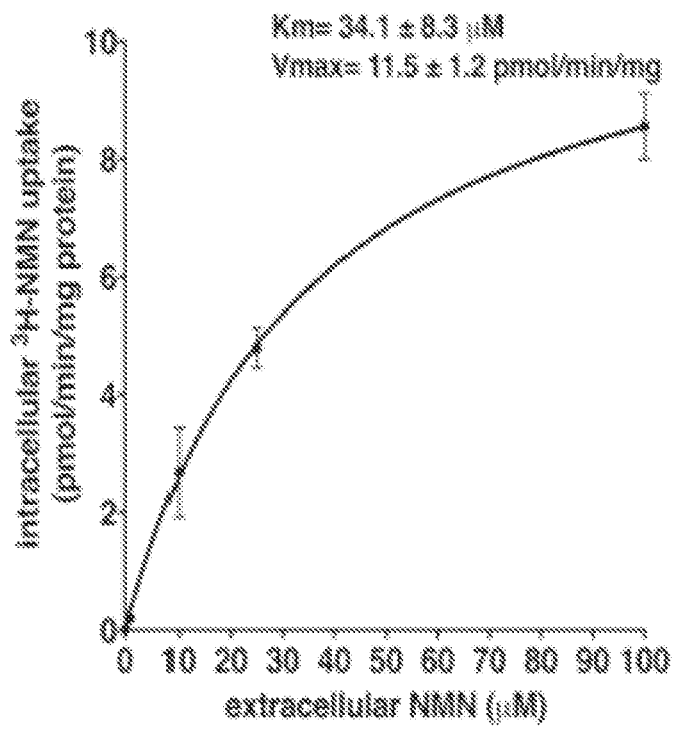
FIG. 12 illustrates the calculation of Michaelis-Menten kinetics by plotting extracellular NMN against intracellular $^3$H-NMN uptake.

Uptake of NMN was measured as described in methods under "NMN uptake analyses with radiolabeled NMN" using 25 µM $^3$H-NMN at 37° C. in control and Slc12a8-OE NIH3T3 cells over 10 min in Hanks' buffer [ph7.5] with Mg2+ and Ca2+ (n=12; analyzed by ANOVA with Sidak's test). The uptake of $^3$H-NMN was significantly enhanced at 3 and 5 min time points in Slc12a8-OE cells, compared to control cells (FIG. 11). In order to calculate the Michaelis-Menten parameters for the Slc12a8 protein, control and Slc12a8-OE NIH3T3 cells were incubated with 100 nM of $^3$H-NMN and increasing concentrations of cold NMN for 4 min in Hanks' buffer [pH7.5] with Mg2+ and Ca2+ at 37° C. Km and Vmax values were determined by non-linear regression analysis by subtracting the backgrounds of control cells (n=5 for 1 and 10 µM, and n=4 for 25 and 100 µM). For NMN, the Km was 34.1±8.3 µM and the Vmax was 11.5±1.2 pmol/min/mg (FIG. 12). This Km is qualitatively consistent with a detected range of NMN concentrations in mouse plasma and erythrocytes (Revollo, J. R. et al., Cell Metab., 6, 363-375, 2007; Ramsey, K. M., et al., Science, 324, 651-654, 2009; Yamada, K., et al., Anal. Biochem., 352, 282-285, 2006).

Example 7

This example illustrates the specificity of the Slc12a8 protein.

Figure 13:
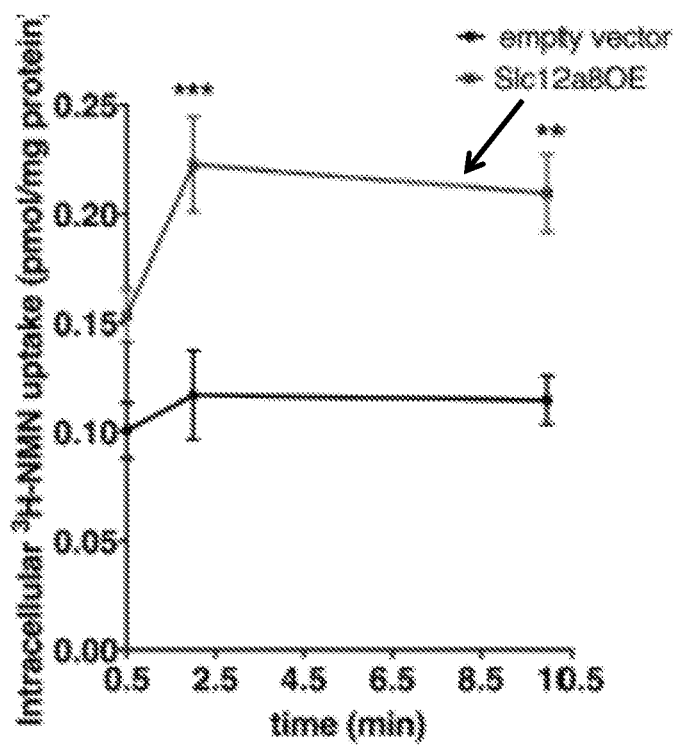
FIG. 13 illustrates $^3$H-NMN uptake of proteoliposomes derived from either Slc12a8-OE cells or control cells.

Proteoliposomes were produced by combining the membrane fractions of Slc12a8-OE or control NIH3T3 cells with the phospholipid bilayers derived from deproteinized erythrocyte plasma membrane as described supra using 22 nM, $^3$H-NMN at 25° C. in proteoliposomes produced from plasma membrane fractions of Slc12a8-OE and control NIH3T3 cells in transport buffer (n=3; analyzed by one-way ANOVA with Sidak's multiple comparisons test). Slc12a8-OE-derived proteoliposomes incorporated significantly higher levels of $^3$H-NMN than those from control-derived proteoliposomes within 2 min (FIG. 13).

Figure 42:
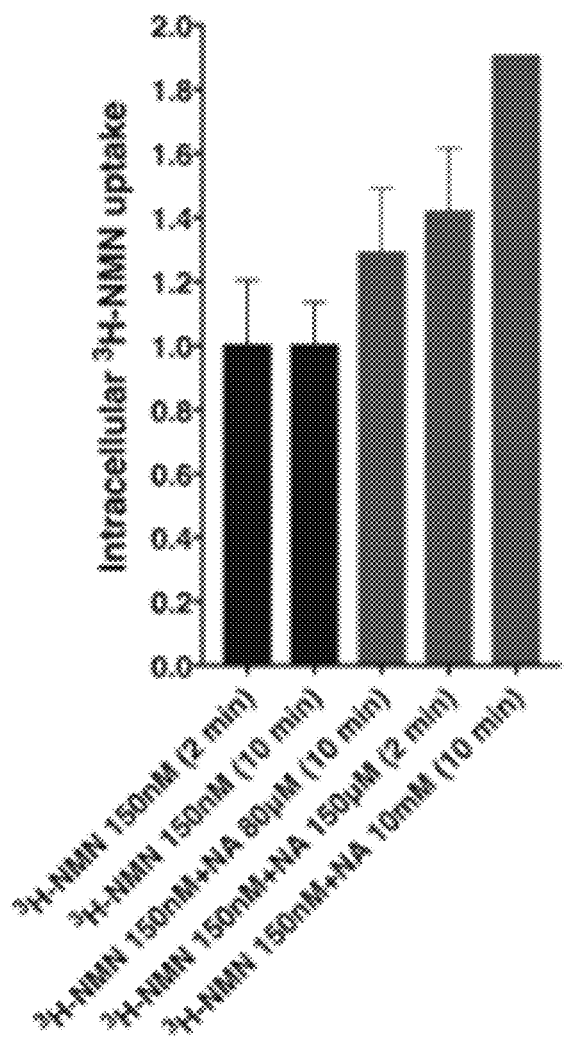
FIG. 42 illustrates enhancement of 3H-labeled NMN ($^3$H-NMN) uptake into Slc12a8-containing proteoliposomes by nicotinic acid (NA).

In some experiments, it was found that nicotinic acid (NA) is able to enhance the uptake of radiolabeled $^3$H-NMN into Slc12a8-everexpressing proteoliposomes (FIG. 42). The enhancement of $^3$H-NMN uptake by NA was reproduced under several different conditions (FIG. 42).

Figure 14:
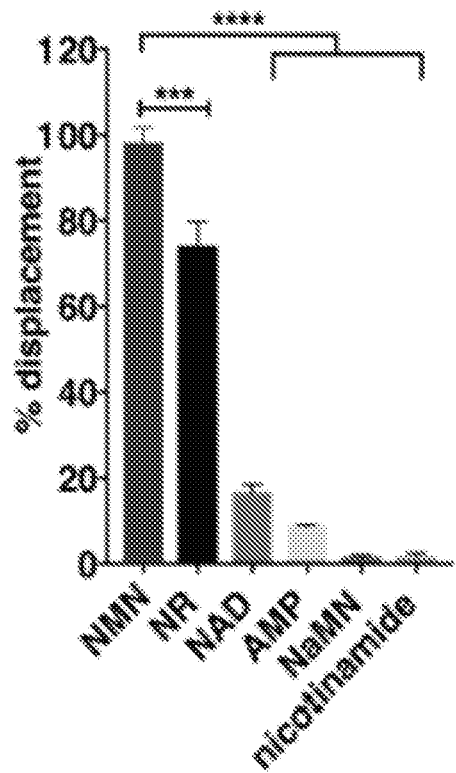
FIG. 14 illustrates displacement of $^3$H-NMN against cold NAD$^+$ related compounds to determine substrate specificity of Slc12a8.
Figure 15:
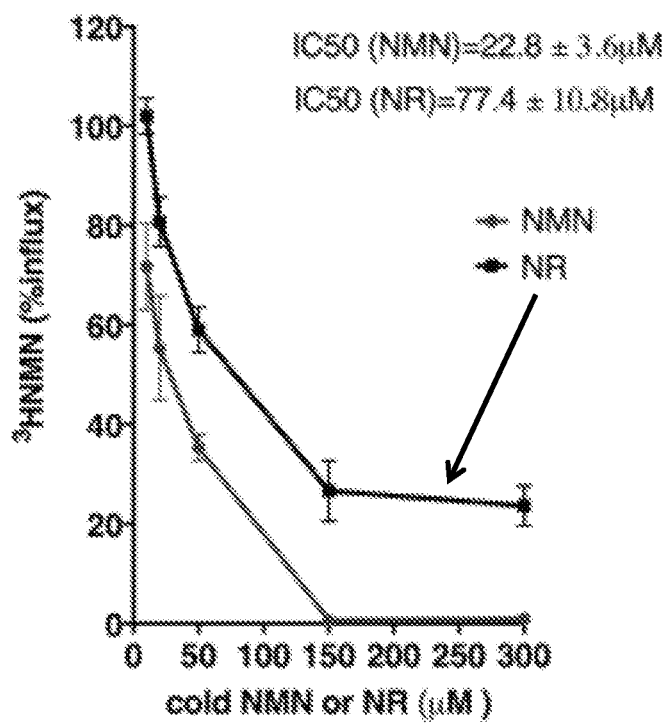
FIG. 15 illustrates the determination of the IC$_{50}$ for NMN and NR using the proteoliposome system.

In order to determine substrate specificity of Slc12a8, these Slc12a8-OE proteoliposomes were used for displacement experiments with $^3$H-NMN and various cold NAD+-related compounds. Uptake of $^3$H-NMN (150 nM, 25° C.) was measured at 2 min in Slc12a8-OE proteoliposomes in the presence of 150 µM competing cold compounds (NMN, NR, NAD, AMP, NaMN, and nicotinamide) in transport buffer (n=3, analyzed by ANOVA with Dunnett's test). 150 µM of cold NMN showed complete displacement of $^3$H-NMN, whereas NAD+, AMP, nicotinic acid mononucleotide (NaMN), and nicotinamide showed very low or negligible displacement at the same concentration (FIG. 14). 150 µM NR exhibited ~70% displacement, and therefore $IC_{50}$ concentrations were determined for NMN and NR, using the proteoliposome system. The $IC_{50}$ for NMN was 22.8±3.6 µM, whereas the $IC_{50}$ for NR was 77.4±10.8 µM (FIG. 15). Data are shown as percentages of $^3$H-NMN uptake (n=3; $IC_{50}$ was calculated by non-linear regression analysis). Because it has not been shown that NR levels can reach such a high concentration in pathophysiological conditions, such as in blood (Frederick, D. W., et al., Cell Metab., 24, 269-282, 2016) and ascitic exudates (Sociali, G., et al., Oncotarget, 7, 2968-2984, 2016), and without being limited by theory, this result suggests that the Slc12a8 protein is specific primarily to NMN under physiological conditions.

These findings indicate that NA and some NA derivative compounds can be used to facilitate the function of the Slc12a8 NMN transporter.

Example 8

This example illustrates sodium ion dependency of Slc12a8 for NMN transport.

Figure 16:
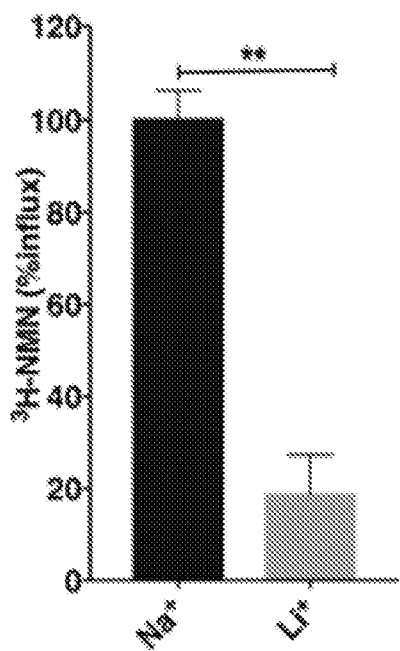
FIG. 16 illustrates the effect of replacing Na$^+$ with Li$^+$ on $^3$H-NMN uptake by proteoliposomes.

In these experiments, the sodium ion dependency of Slc12a8 for NMN transport was evaluated using the proteoliposome system. When sodium (Na+) was replaced with an equimolar concentration of lithium (Li+) during the proteoliposome preparation and NMN-influx measurements, the $^3$H-NMN incorporation was dramatically reduced by ~80% (FIG. 16; n=3, analyzed by unpaired t-test), indicating that NMN transport by Slc12a8 is sodium ion-dependent.

These results indicate that sodium salts can enhance Slc12a8-mediated NMN transport, and that other cations such as lithium can inhibit Slc12a8-mediated NMN transport.

Example 9

This example illustrates the determination of the effect of Slc12a8 overexpression on NAD+ biosynthesis in NIH3T3 cells.

Figure 41:
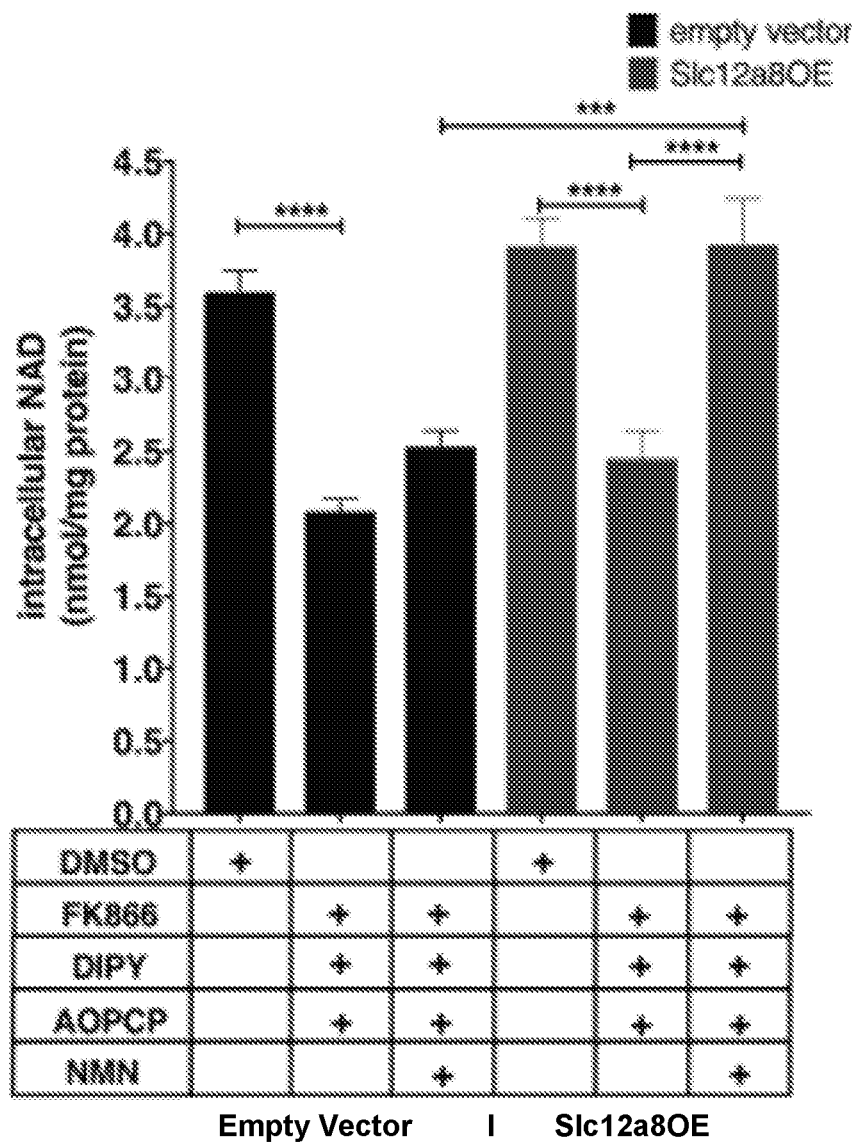
FIG. 41 illustrates the effects of inhibitors of $NAD^+$ biosynthesis in NIH3T3 cells with or without Slc12a8 overexpression constructs.

When control NIH3T3 and Slc12a8-OE cells were pre-treated for 1 hr with a cocktail of 100 nM FK866, 2 µM dipyridamole, and 500 µM AOPCP, intracellular NAD+ levels were significantly reduced in both control and Slc12a8-OE cells (FIG. 41). However, additional 1-hr incubation with 100 µM NMN was able to restore NAD+ levels to the original levels only in Slc12a8-OE cells, not in control NIH3T3 cells (FIG. 41; n=9; analyzed by ANOVA with Tukey's test).

Example 10

This example illustrates in vivo validation of the NMN transporter.

Figure 17:
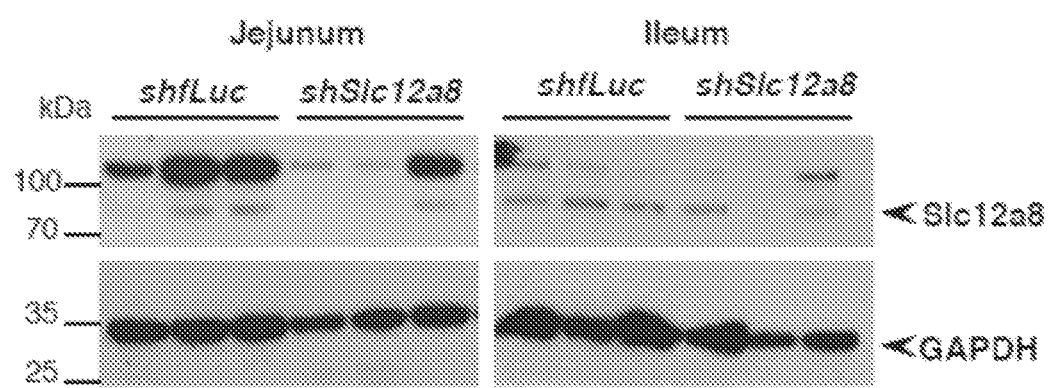
FIG. 17 illustrates a representative Western blot of firefly luciferase (fLuc) shRNA and Slc12a8 shRNA infected mouse jejunum and ileum tissue samples.
Figure 18:
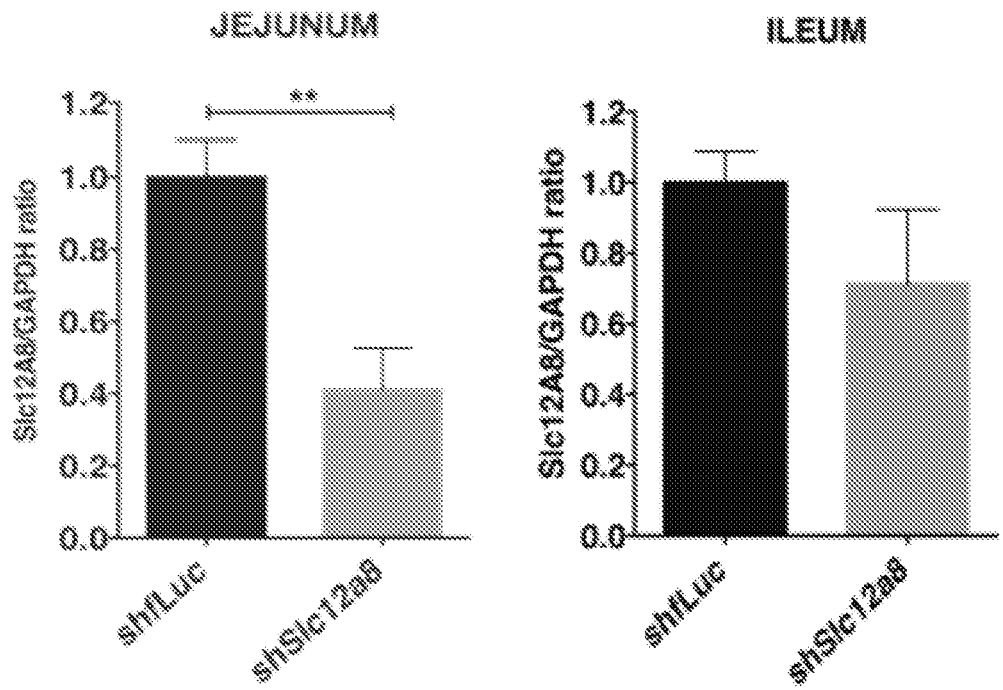
FIG. 18 illustrates bar graphs of firefly luciferase (fLuc) shRNA and Slc12a8 shRNA infected mouse jejunum and ileum tissue samples where the expression levels have been normalized to GAPDH.
Figure 19:
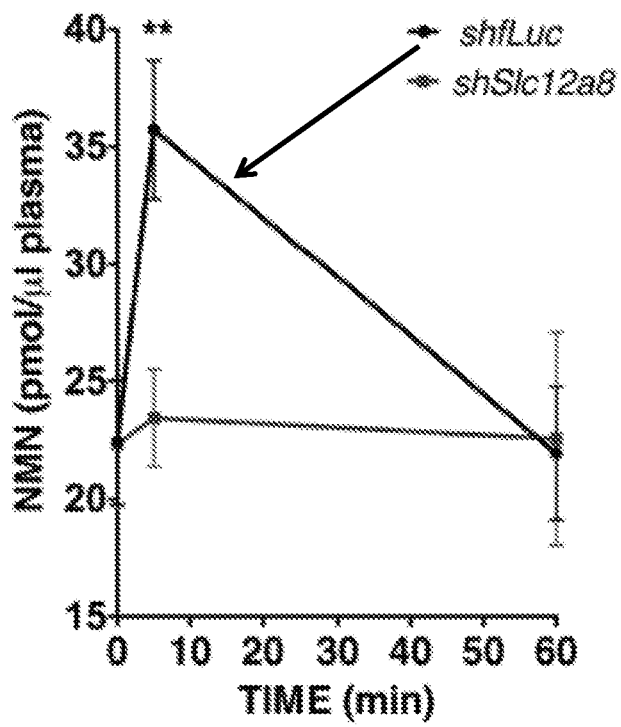
FIG. 19 illustrates mouse in vivo plasma NMN levels measured by HPLC over 60 min after oral gavage of NMN in control and Slc12a8 knockdown mice.
Figure 20:
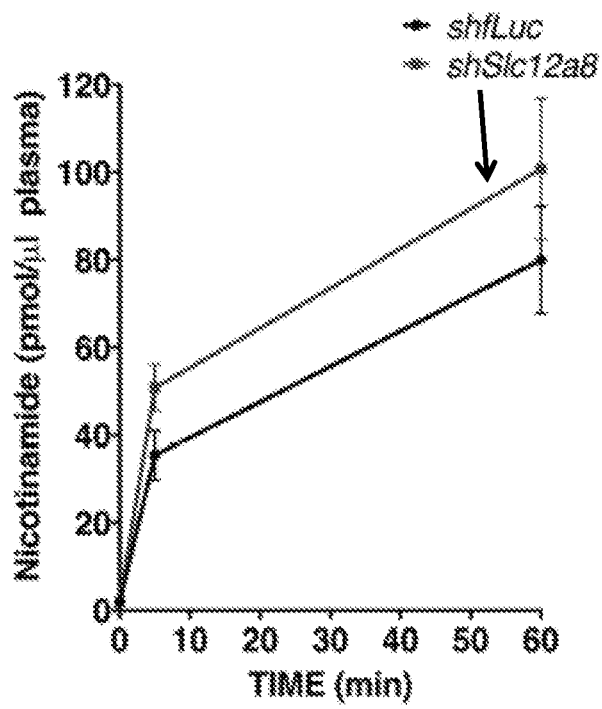
FIG. 20 illustrates mouse in vivo plasma nicotinamide levels measured by HPLC over 60 min after oral gavage of NMN in control and Slc12a8 knockdown mice.
Figure 21:
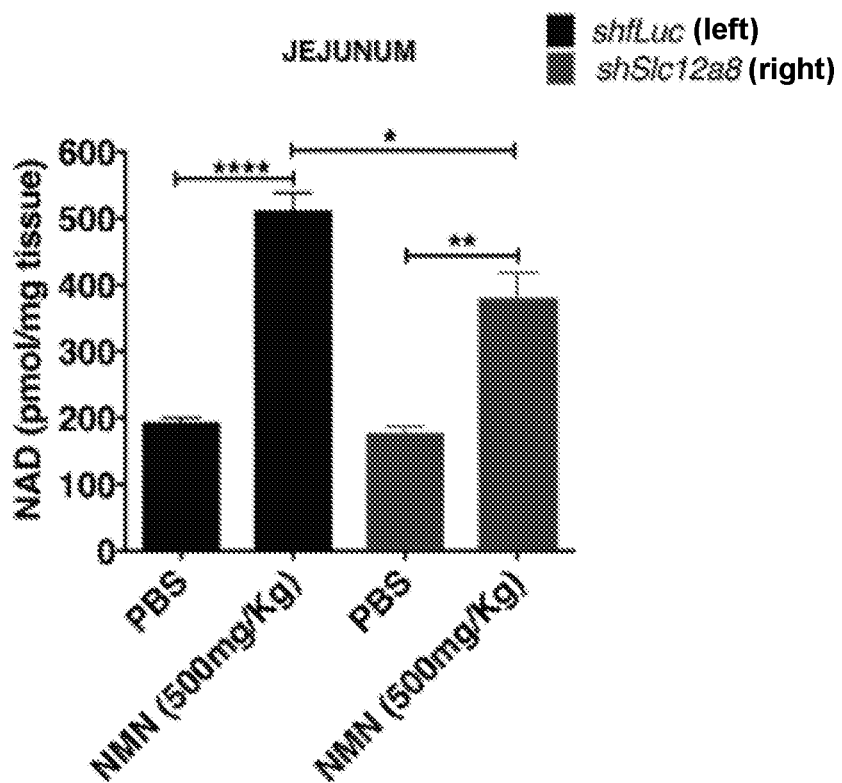
FIG. 21 illustrates NAD concentration in jejunum tissue samples collected 60 minutes following administration of NMN via oral gavage in control vs Slc12a8 knockdown mice.

Lentiviruses carrying control firefly luciferase (fLuc) shRNA and Slc12a8 shRNA were generated as described supra. The inventors conducted a gavage of each virus directly to the mouse gut. Slc12a8 protein expression levels in control shfLuc lentivirus- and shSlc12a8 lentivirus-infected jejunum and ileum samples were measured through Western blots (FIG. 17). FIG. 18 shows a bar graph of Slc12a8 protein levels normalized to GAPDH protein levels in the jejunum and ileum (n=6; B6 males at 3-4 months of age, analyzed by unpaired t-test). Slc12a8 protein levels were reduced by ~60% in the jejunum and ~30% in the ileum in the mice receiving the Slc12a8 shRNA-expressing lentivirus in the gut, compared to the mice receiving the fLuc shRNA-expressing lentivirus (FIG. 17-18). When NMN (500 mg/kg body weight) was administered by oral gavage to those mice, plasma NMN levels significantly increased at 5 min in the control mice, whereas they did not increase at all in the Slc12a8-knockdown mice (FIG. 19; NMN measured by HPLC; n=6; B6 males at 3-4 months of age, analyzed by ANOVA with Sidak's test). Instead, plasma nicotinamide levels tended to be higher in Slc12a8-knockdown mice compared to control mice (FIG. 20), probably because higher levels of NMN were subjected to degradation to nicotinamide in Slc12a8-knockdown mice. In addition to plasma samples, tissue samples from the jejunum were collected at the 60 min time point after oral gavage of phosphate buffer saline (PBS) or NMN (500 mg/kg body weight) in control shfLuc lentivirus- and shSlc12a8 lentivirus-infected mice (n=5 mice for PBS, and n=8 for NMN; B6 males at 3-4 months of age). Then NAD+ levels were measured by HPLC in these samples (analyzed by ANOVA with Tukey's test). NAD+ levels were significantly decreased in the jejunum of Slc12a8-knockdown mice compared to control mice (FIG. 21). These results strongly suggest that Slc12a8 in the small intestine is important to absorb NMN from the gut to blood circulation, affecting NAD+ levels in the small intestine and the systemic NMN supply in vivo.

Example 11

This example illustrates characterization of Slc12a8 knockout mice.

Figure 22:
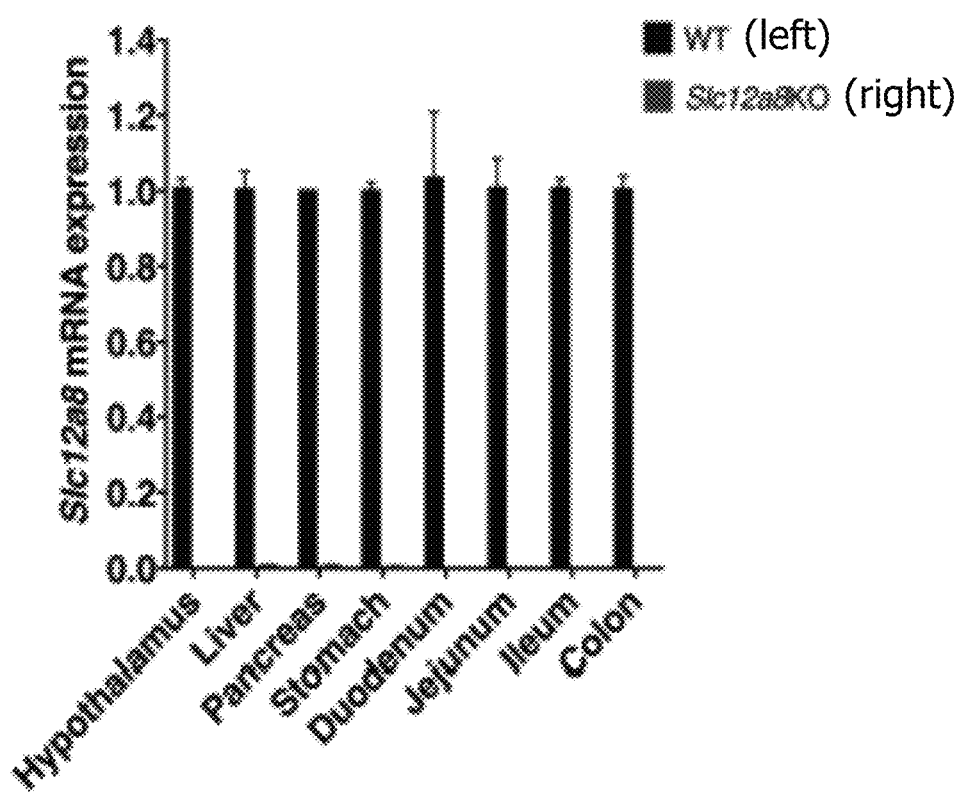
FIG. 22 illustrates Slc12a8 mRNA expression in various tissues in control vs Slc12a8 knockout mice.
Figure 23:
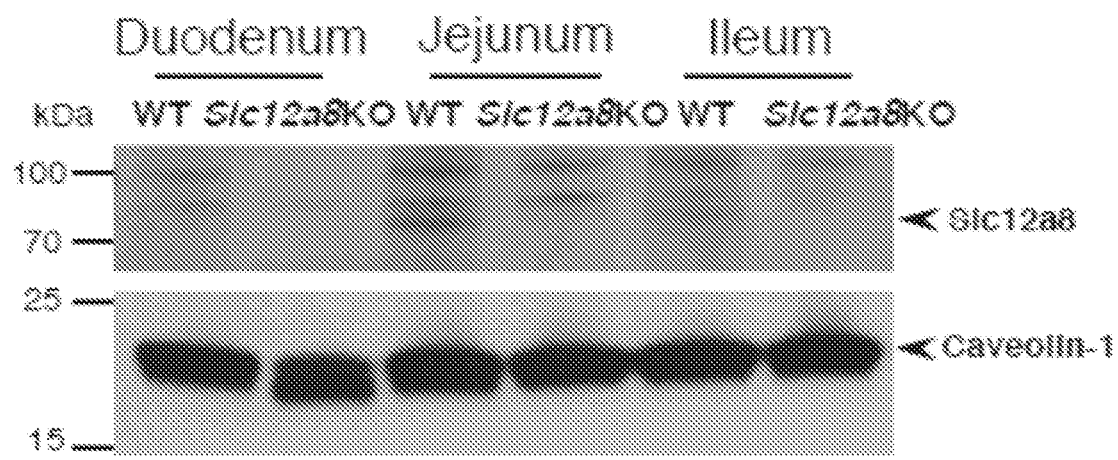
FIG. 23 illustrates the absence of Slc12a8 protein in the duodenum, jejunum, ileum, and pancreas of Slc12a8 knock out mice via Western blot.
Figure 23:
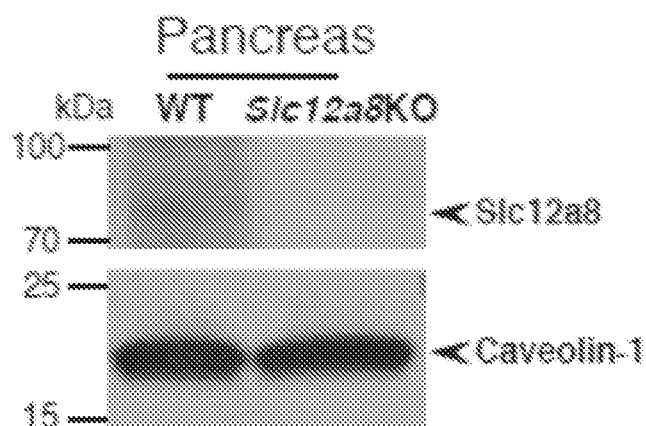
Figure 24:
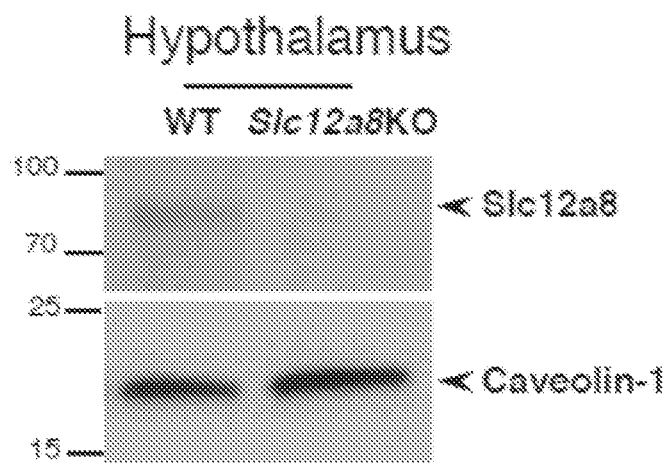
FIG. 24 illustrates the absence of Slc12a8 protein in the hypothalamus of Slc12a8 knock out mice via Western blot.
Figure 25A:
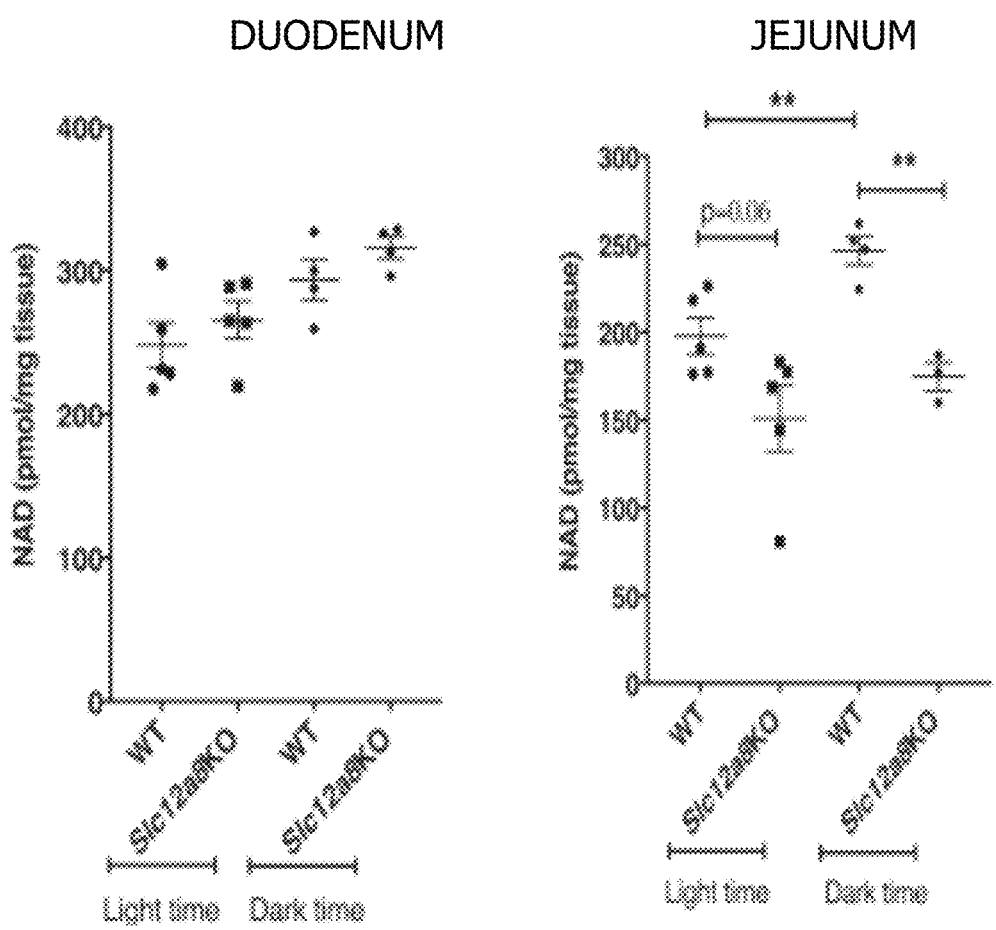
FIG. 25A-B illustrates NAD+ levels in various tissue samples collected from Slc12a8 knock-out mice during both light and dark times of day.
Figure 25B:
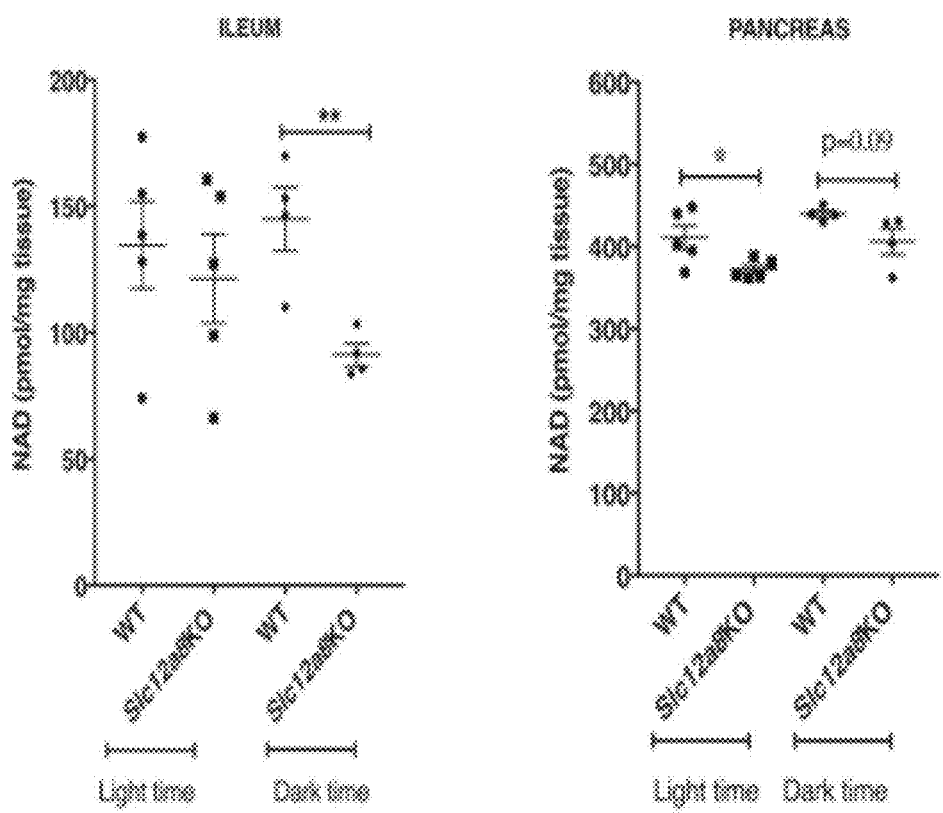
Figure 26:
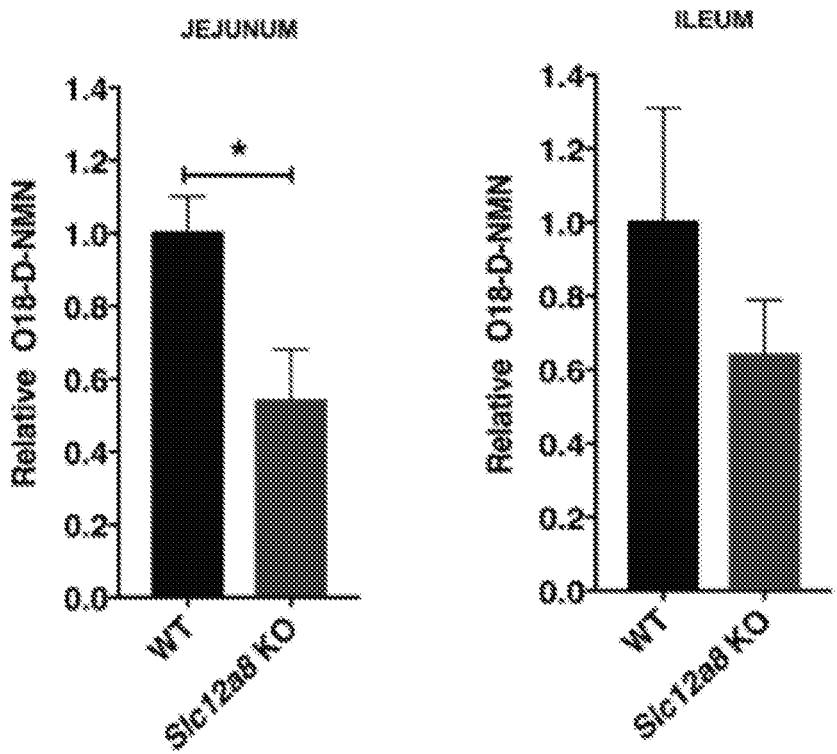
FIG. 26 illustrates the uptake of $^{18}$O-D-NMN following administration by gavage in SLc12a8 knock-out mice and their wildtype litter mates.

Exon 4 of the Slc12a8 gene was excised from mice using the CRISPR-CAS9 system as described supra, which produced whole body Slc12a8 knockout (Slc12a8KO) mice. The birth ratio of these knockout mice was lower than the expected Mendelian ratio, implying that there was some premature death during the embryonic stage. However, the pups that were born grew to adulthood, and did not show any gross abnormalities. Tissue samples of duodenum, jejunum, ileum, and pancreas from Slc12a8KO mice and control wild-type littermates (WT), were collected during light time (9-10 am) or during dark time (9-10 pm). NAD+ levels were measured by HPLC in these samples (n=5 mice for the light time, and n=4 mice for the dark time, except for the 3 data points for the jejunum of Slc12a8KO mice; females at 8-10 months of age; analyzed by unpaired t-test). In adult Slc12a8KO mice, the expression of the full-length Slc12a8 mRNA was completely abolished in tissues (n=3, males at 2-3 months of age; FIG. 22). Slc12a8 protein expression was also shown to be abolished in the whole tissue lysates of the jejunum and ileum (FIG. 23), the pancreas (FIG. 23) and the hypothalamus (FIG. 24) of the Slc12a8KO mice by Western blotting. Antiserum against the first 17 amino acids of the N-terminal domain of Slc12a8 was used. The duodenum of the knockout mice does not express the full-length Slc12a8 protein (FIG. 23), even though it expresses high levels of Slc12a8 mRNA in wild-type mice (FIG. 2). Consistent with the protein expression profile in the small intestine, the Slc12a8KO mice showed significant decreases in NAD+ levels in the jejunum and ileum, but not in the duodenum, particularly during the dark time when NAD+ 198 levels usually rise (FIG. 25A-B). They also showed NAD+ decreases in the pancreas during both light and dark times (FIG. 25A-B). To confirm whether NMN transport is compromised in the small intestine of the Slc12a8KO mice, the inventors conducted a gavage of doubly labeled, 3-D, a heavier, isotopic NMN (18O-D-NMN) and measured the direct uptake of 18O-D-NMN into the jejunum and ileum by mass spectrometry. At 10 min after administering 500 mg/kg of 758 18O-D-NMN in Slc12a8KO mice and control wild-type (WT) littermates by oral gavage, this isotopic NMN was clearly detected in the wild-type jejunum and ileum, whereas the uptake of 18O-D-NMN decreased by 46% and 36% in the jejunum and ileum of the Slc12a8KO mice, respectively (FIG. 26; n=6 mice, 3 males and 3 females at 7-8 months of age, except for 2 males and 2 females for the wild-type ileum; analyzed by unpaired t-test). The areas under the peaks of 18O-D-NMN were calculated by subtracting the background values of PBS controls. Values are expressed relative to 18O-D-NMN levels detected in WT. In this example, all values are presented as mean±SEM. *$p<0.05$, **$p<0.01$ Example 12

This example illustrates that Slc12a8KO mice exhibit hyperphagia without an effect on fat or lean masses.

Figure 27:
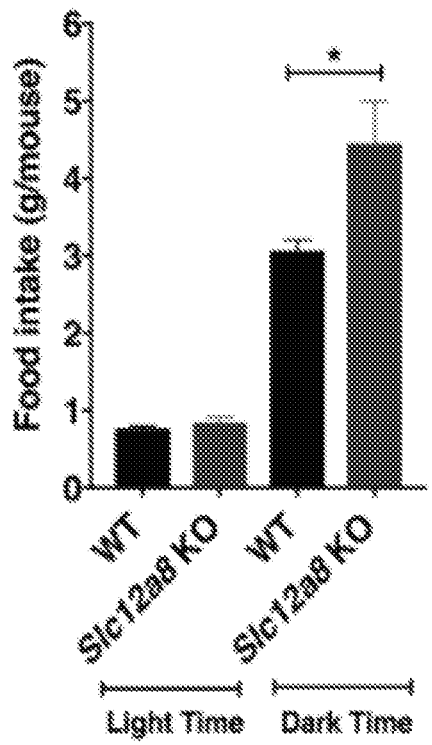
FIG. 27 illustrates food intake of Slc12a8 knock out mice compared to their wild type littermates.
Figure 28:
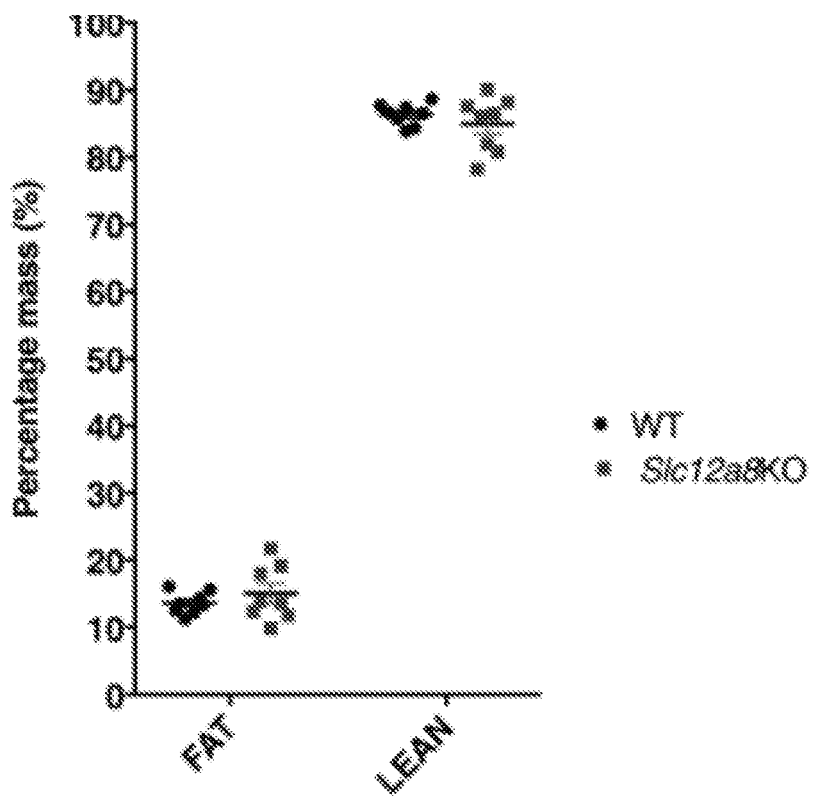
FIG. 28 illustrates fat vs lean mass percentages of Slc12a8 knock out mice compared to their wild type littermates.
Figure 29:
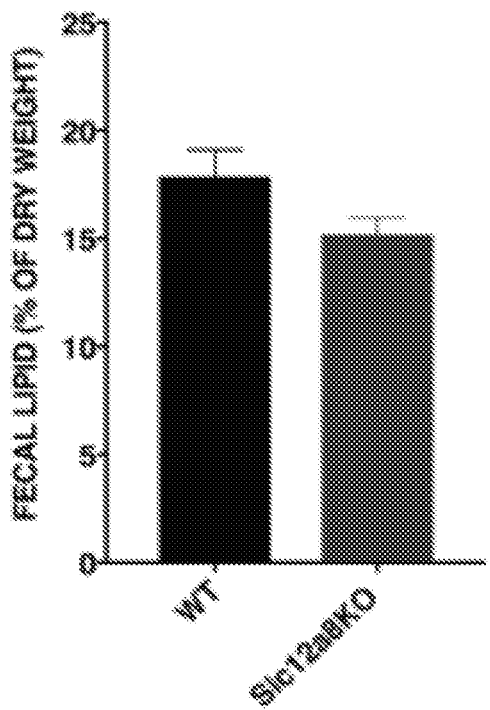
FIG. 29 illustrates fecal lipid content of Slc12a8 knock out mice compared to their wild type littermates.

At 6-7 months-old, the Slc12a8KO mice, particularly the females, started displaying significant hyperphagia during the dark time (FIG. 27). Food intake was measured for 5 days in Slc12a8KO mice and control wild-type (WT) littermates during the light time (9 am-6 pm) and the dark time (6 pm-9 am) (n=8 mice for each genotype; females at 6-7 months of age; analyzed by unpaired t-test). However, the Slc12a8KO mice did not show any differences in fat and lean masses compared to wild-type controls (FIG. 28). Fat and lean masses were measured using a whole-body NMR instrument in Slc12a8KO and control wild-type littermates (n=8 mice for each genotype; females at 8-10 months of age). The exhibited hyperphagia was not due to malabsorption in the gut because there were no differences in fecal lipid content between control and Slc12a8KO mice (FIG. 29). Total lipid content, expressed as percentage of starting fecal mass extracted, was measured in feces collected at 9-10 am from Slc12a8KO mice and control wild-type littermates (n=8 mice for each genotype, females at 6-8 months).

Example 13

This example illustrates increased respiration and activity of Slc12a8KO mice.

Figure 30:
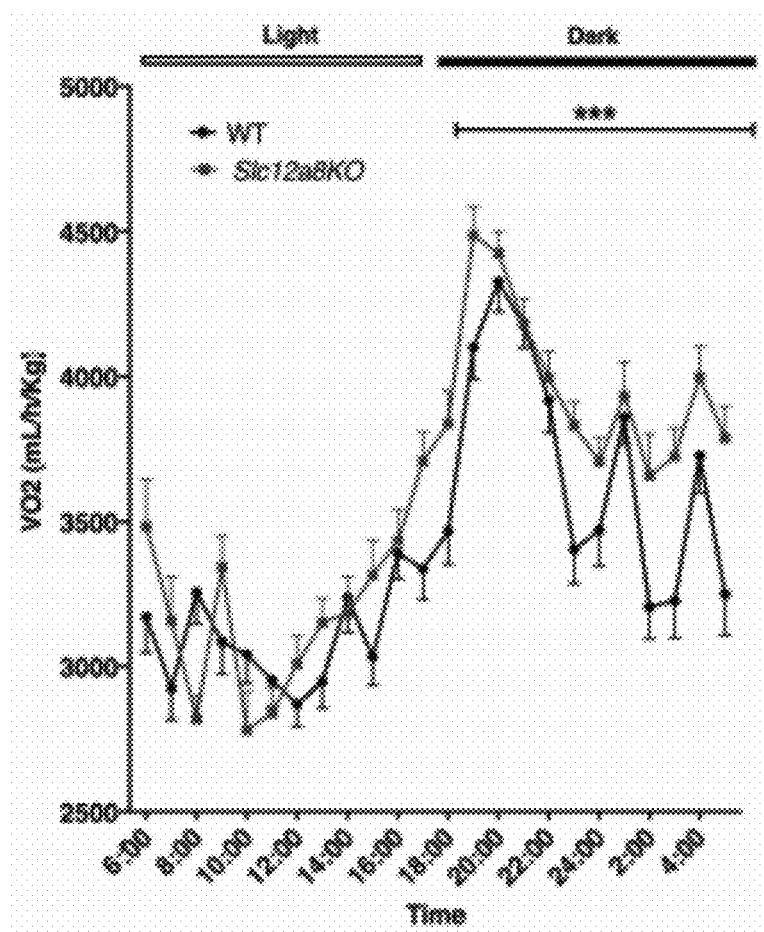
FIG. 30 illustrates oxygen consumption of Slc12a8 knock out mice compared to their wild type littermates.
Figure 31:
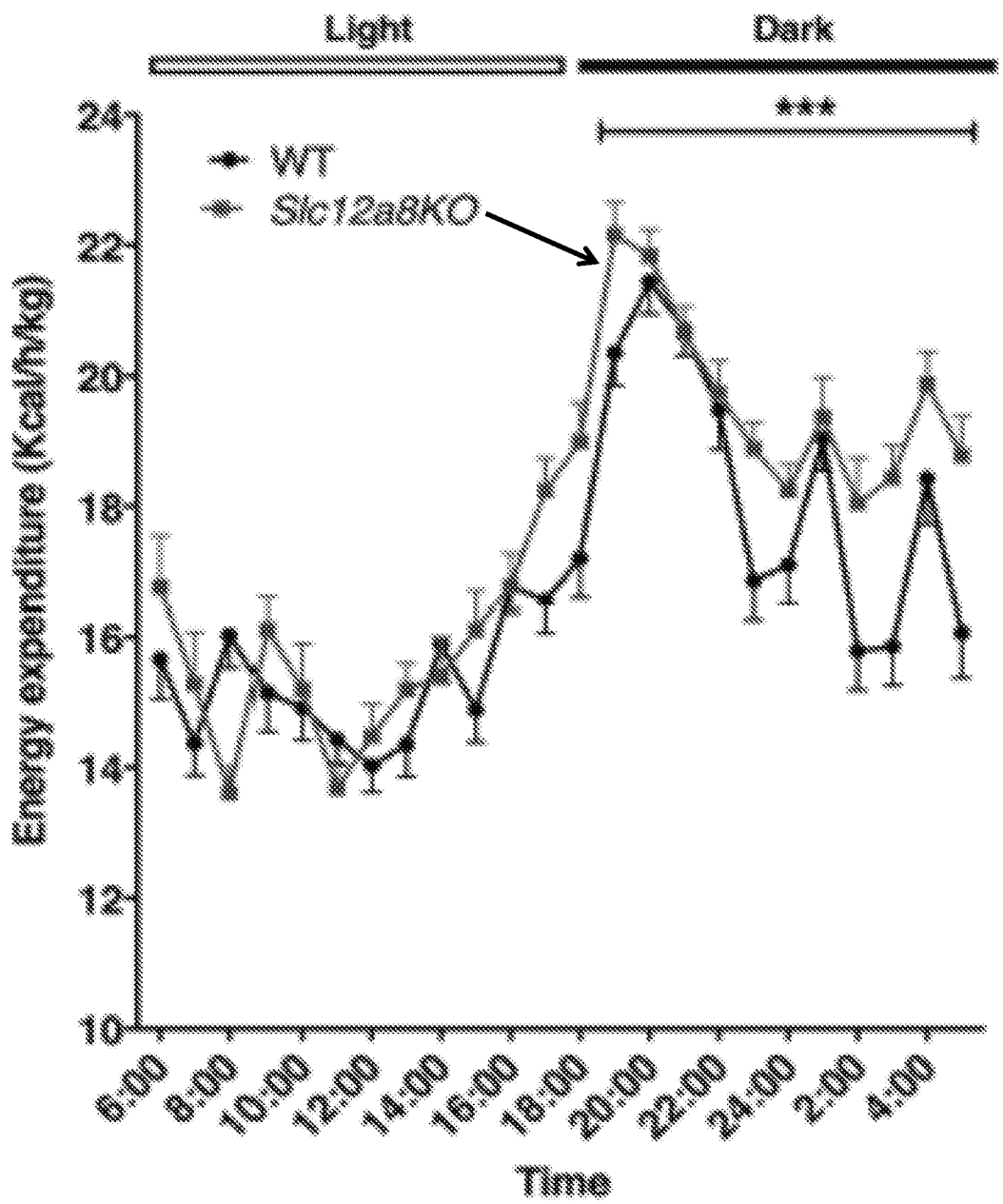
FIG. 31 illustrates energy consumption of Slc12a8 knock out mice compared to their wild type littermates.
Figure 32:
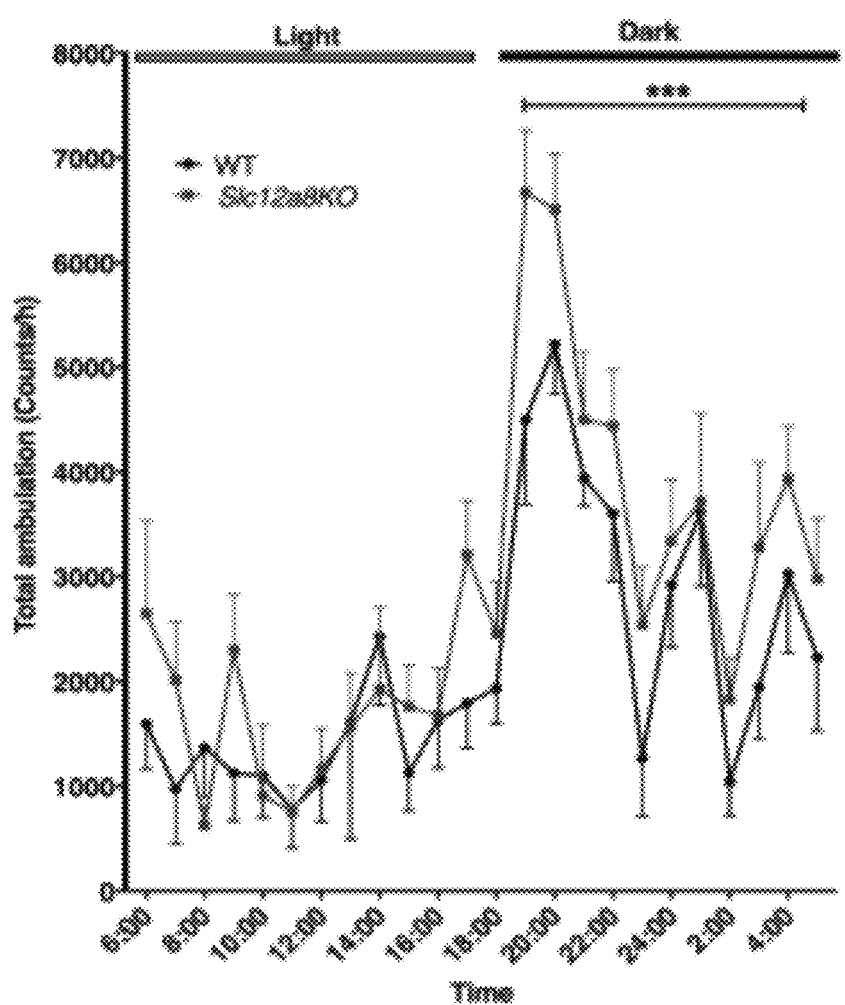
FIG. 32 illustrates ambulation counts of Slc12a8 knock out mice compared to their wild type littermates.
Figure 33:
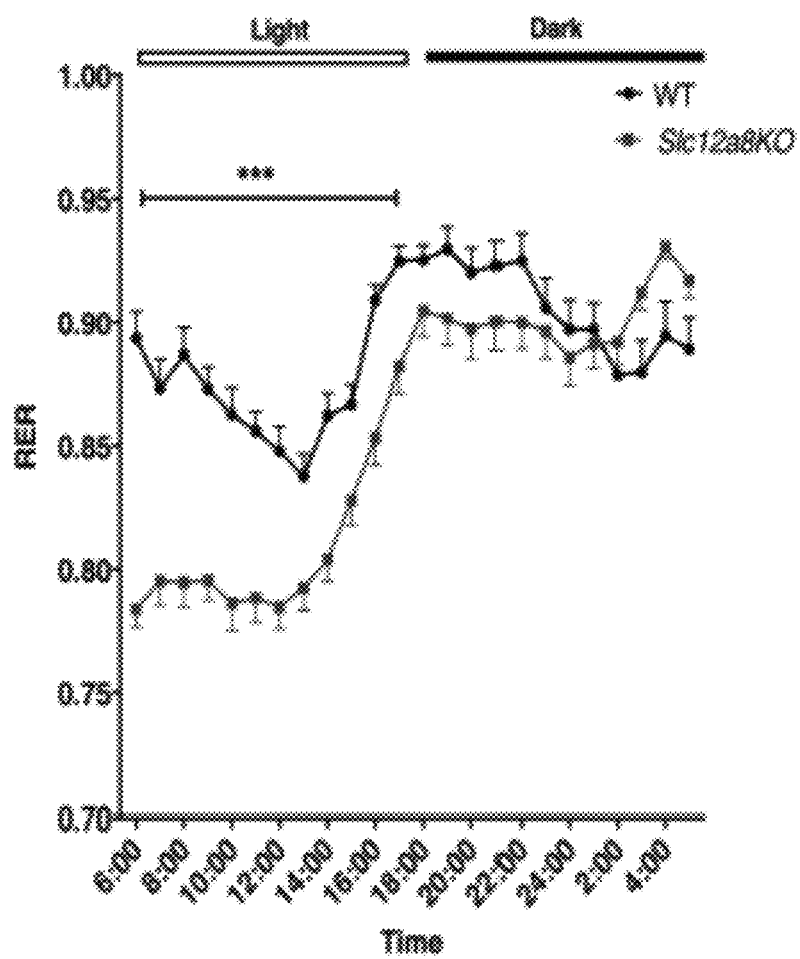
FIG. 33 illustrates lower respiratory exchange ratios of Slc12a8 knock out mice compared to their wild type littermates.

Interestingly, the Slc12a8KO mice exhibited moderate increases in oxygen consumption (VO2; FIG. 30), energy expenditure (FIG. 31), and total ambulation (FIG. 32) during the dark time, providing an explanation for their hyperphagic phenotype with no body weight gain. These mice also showed significantly lower respiratory exchange ratios (RER; FIG. 33), implicating higher fatty acid utilization, during the light time, providing an additional explanation for the maintenance of normal fat mass, even though no difference was detected in plasma fatty acid levels between control and Slc12a8KO mice (not shown).

Example 14

This example illustrates increased glucose metabolism in Slc12a8 knock out mice.

Figure 34:
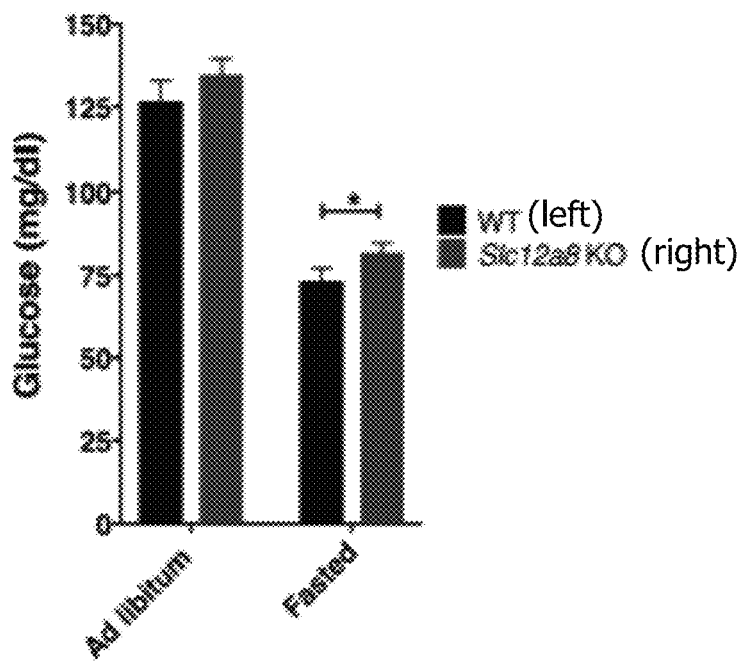
FIG. 34 illustrates glucose levels of Slc12a8 knock out mice compared to their wild type littermates.
Figure 35:
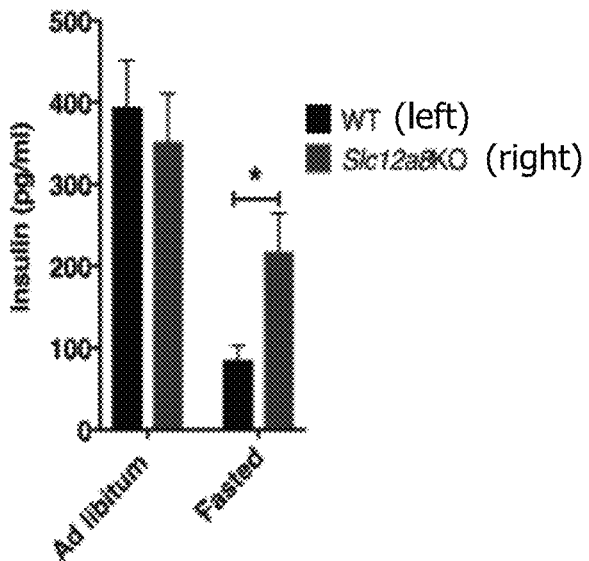
FIG. 35 illustrates insulin levels of Slc12a8 knock out mice compared to their wild type littermates.
Figure 36:
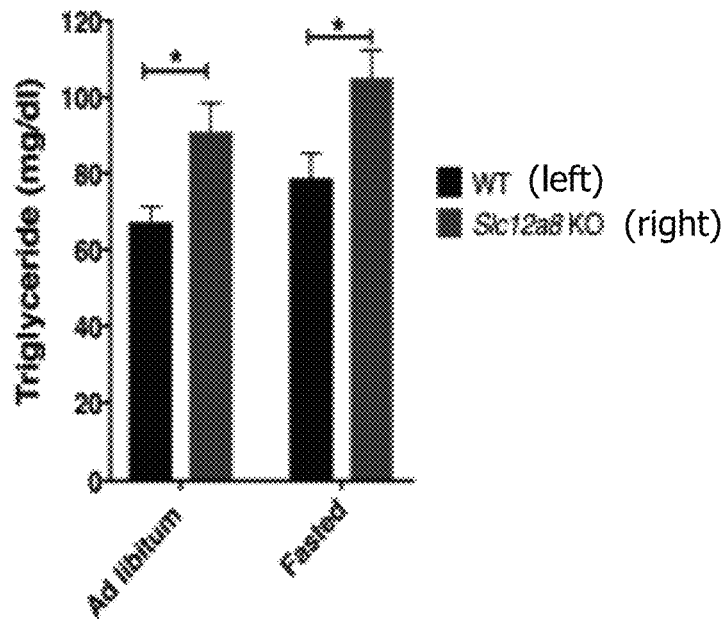
FIG. 36 illustrates triglyceride levels of Slc12a8 knock out mice compared to their wild type littermates.

When fasting for 16 hours, female Slc12a8KO mice (n=8 mice for each genotype; females at 6-8 months of age; analyzed by unpaired t-test) exhibited higher glucose (FIG. 34), insulin (FIG. 35), and triglyceride levels (FIG. 36).

Without being limited by theory, all these phenotypes collectively implicate hypothalamic dysfunction.

Example 15

This example illustrates glucagon-like peptide 2 receptor (GLP-2R) impairment in Slc12a8 knock out mice.

Figure 37:
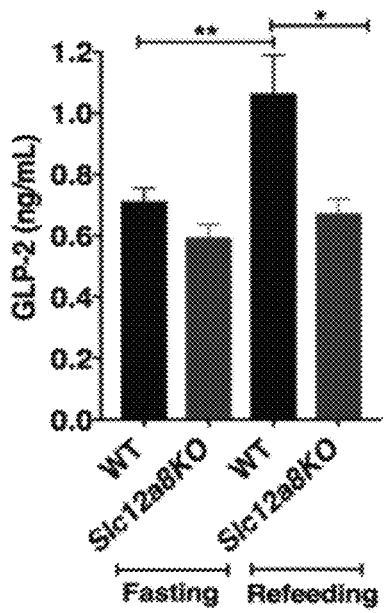
FIG. 37 illustrates plasma levels of GLP-2 under fasting and refeeding conditions for Slc12a8 knock out mice compared to their wild type littermates.

GLP-2R is a 33-amino acid proglucagon derived peptide produced by enteroendocrine L cells. Plasma GLP-2 levels were measured by ELISA in Slc12a8KO mice and control wild-type littermates after 24 h fasting (from 9 am till 9 am) and then after 6 h refeeding (from 10 am till 4 pm) (n=8 mice for each genotype; females at 7-8 months of age). The Slc12a8KO mice showed significantly lower plasma levels of GLP-2, in response to 6-hr refeeding after 24-hr fasting, whereas control mice showed a significant increase in plasma GLP-2 levels in refeeding (FIG. 37).

Example 16

This example illustrates expression disruptions in the arcuate nuclei of Slc12a8 knock out mice.

Figure 38:
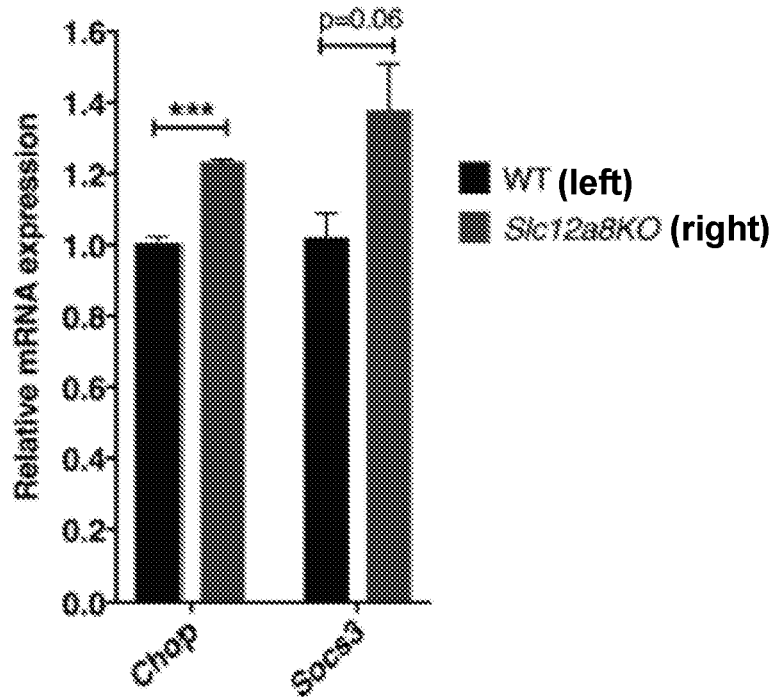
FIG. 38 illustrates relative mRNA expression of Chop and Socs3 in the arcuate nucleus of Slc12a8 knock out mice compared to their wild type littermates.
Figure 39:
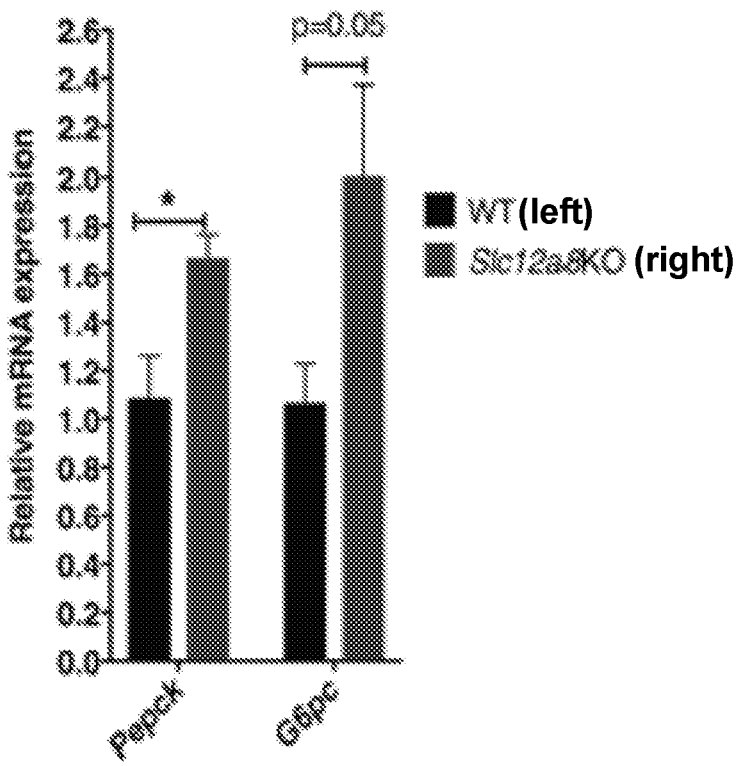
FIG. 39 illustrates Pepck and Gopc expression in the livers of ad libitum fed Slc12a8 knock out mice compared to their wild type littermates.

Chop (DNA Damage Inducible Transcript 3) and Socs3 (Suppressor Of Cytokine Signaling 3) are upregulated in response to endoplasmic reticulum (ER) stress and resultant leptin resistance. Chop and Socs3 mRNA expression levels were measured in hypothalamic arcuate nuclei of Slc12a8KO mice and control wild-type littermates during the dark time (9-10 pm) (Chop, n=3 mice for each genotype; Socs3, n=4 mice for each genotype; females at 8-10 months of age; analyzed by unpaired t-test). Consistent with this lack of proper GLP-2 stimulation, the arcuate nucleus of the Slc12a8KO mice exhibited increases in mRNA expression levels (FIG. 38). Without being limited by theory, these results suggest the dysfunction of arcuate neurons (Williams, K. W., et al., Cell Metab., 20, 471-482, 2014). Pepck (Phosphoenolpyruvate carboxykinase) and G6pc (Glucose-6-Phosphatase Catalytic Subunit) mRNA expression levels were measured in the livers from ad libitum fed Slc12a8KO mice and control wild-type littermates (n=5 mice for each genotype; females at 8-10 months of age; analyzed by unpaired t-test). These gluconeogenic genes were found to be upregulated in the Slc12a8KO mice (FIG. 39). Without being limited by theory, these data further provide evidence for the dysfunction of arcuate neurons and explaining higher glucose and insulin levels in the fasted Slc12a8KO mice.

Example 17

This example illustrates the diurnal mRNA expression profile of PMCH in Slc12a8 knock out mice.

Figure 40:
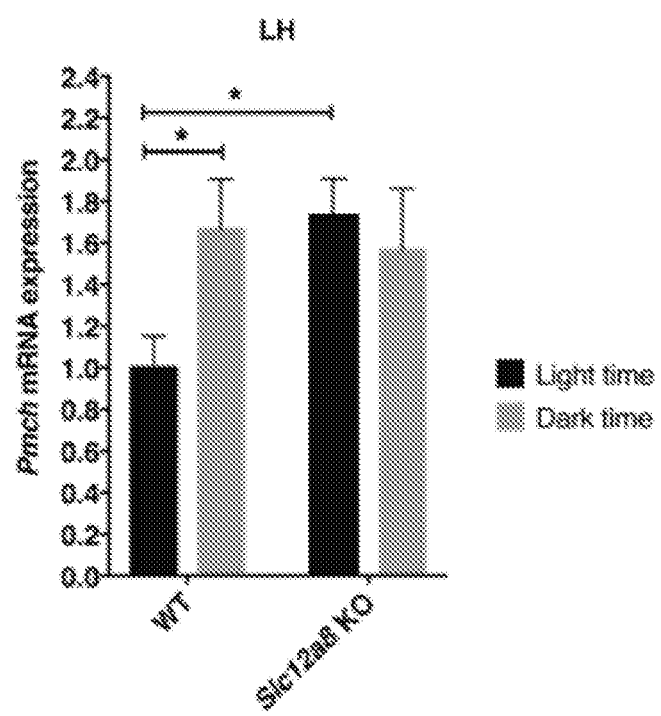
FIG. 40 illustrates PMCH mRNA expression in Slc12a8 knock out mice compared to their wild type littermates.

PMCH (Pro-Melanin Concentrating Hormone) mRNA expression levels were measured in the lateral hypothalami (LH) of Slc12a8KO mice and control wild-type littermates during the light time (at 9-10 am) and the dark time (at 9-10 pm) (n=3 mice for each genotype; females at 8-10 months of age; analyzed by unpaired t-test). The diurnal mRNA expression profile of PMCH was abnormal in the lateral hypothalamus of the Slc12a8KO mice (FIG. 40), which showed little change in expression between the light time and the dark time, while expression of PMCH in wild type littermates significantly increased during the dark time. Without being limited by theory, the NMN transporter deficiency globally affects hypothalamic functions. No abnormalities were detected in the expression of genes encoding major neuropeptides and their receptors in other hypothalamic nuclei of the Slc12a8KO mice (not shown). Without being limited by theory, these findings reveal a novel function of the Slc12a8 NMN transporter, which regulates a proper inter-tissue communication between the gut and the hypothalamus, likely through NMN itself and GLP-2.

Example 18

This example illustrates NAD+ and Slc12a8 concentrations in the small intestine

Figure 43:
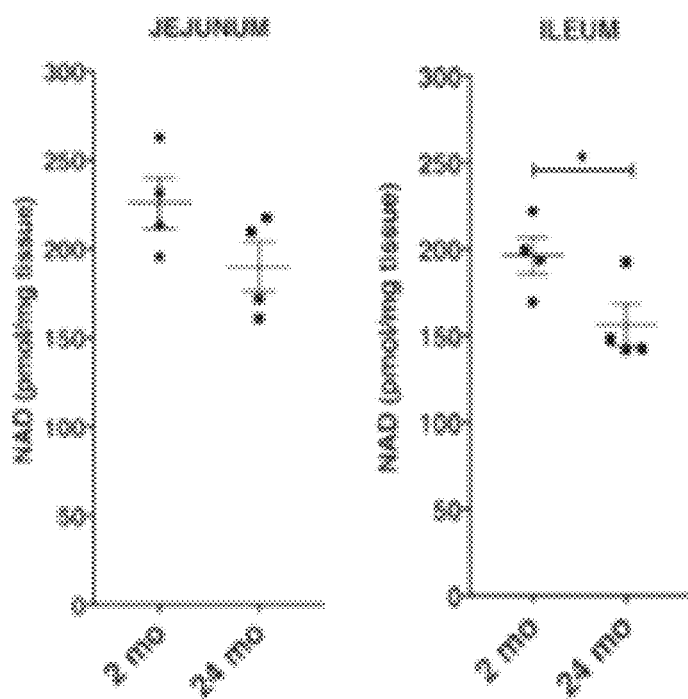
FIG. 43 illustrates decreased $NAD^+$ levels in the jejuna and ilea of 24-month old mice relative to 2-month old mice.
Figure 44:
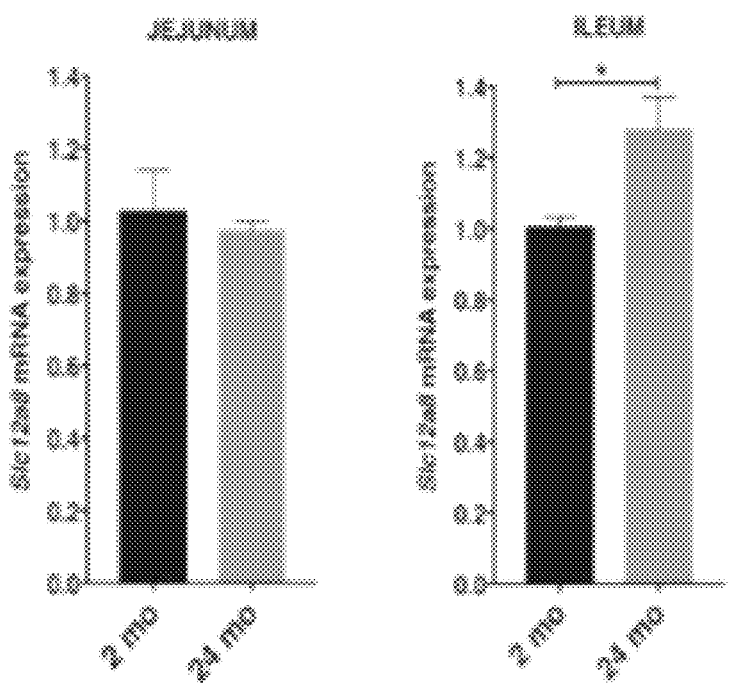
FIG. 44 illustrates Slc12a8 expression in the jujuna nad ilea of 2- and 24-month old mice.

It has been well documented that NAD+ content decreases over age in multiple tissues (Yoshino, J., et al., Cell Metab., 2018, 27:513-528, 2018). NAD+ levels were measured in the jejuna and ilea from 2-month-old (2 mo) and 24-month-old (24 mo) female B6 mice, collected during dark time (9-10 pm). NAD+ content decreases over age in the jejunum and ileum, although the difference did not reach statistical significance in the jejunum (FIG. 43; (n=4 mice for each age, analyzed by unpaired t-test)). Slc12a8 mRNA expression was measured in the jejuna and ilea from 2-month-old (2 mo) and 24-month-old (24 mo) female B6 mice, and collected during dark time (9-10 pm) (n=4 mice for each age, analyzed by unpaired t-test). Consistent with the observed NAD+ decrease, Slc12a8 expression was significantly upregulated in the aged ileum (FIG. 44). These results illustrate that Slc12a8 upregulation correlates with decreased NAD+ in the gut.

Example 19

This example illustrates the effect of Slc12a8 gut knockdown on glucose metabolism in mice.

Figure 45:
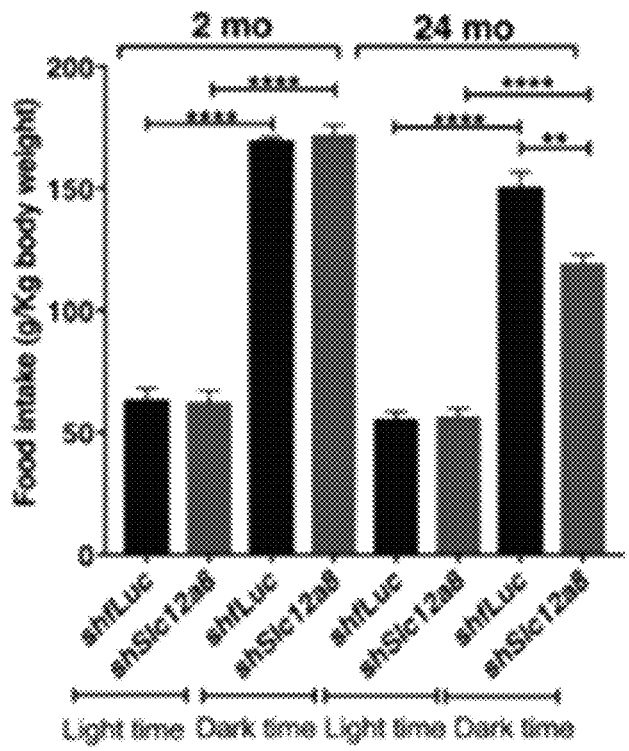
FIG. 45 illustrates 4 days of food intake in 2- and 24-month old intestinal Slc12a8 knockdown mice.
Figure 46:
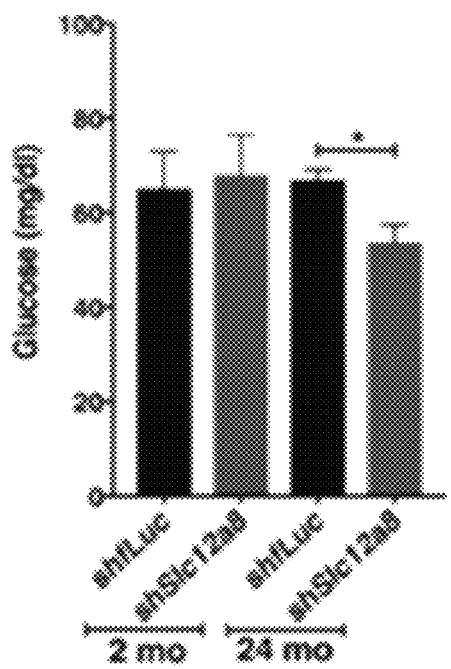
FIG. 46 illustrates fasting glucose levels in 2-month-old and 24-month-old mice with or without Slc12a8 knockdown in the gut.

The inventors conducted oral gavages of lentiviruses carrying control firefly luciferase (fLuc) shRNA and Slc12a8 shRNA to 2- and 24-month-old mice and examined their ingestive behavior. Food intake was measured for 4 days in 2- or 24-month-old intestinal Slc12a8 knockdown female B6 mice (shSlc12a8) and control mice (shfLuc) during the light time (9 am till 6 pm) and the dark time (6 pm till 9 am). Intriguingly, the gut-specific Slc12a8 knockdown caused significant decreases in food intake during the dark time in aged mice, whereas it did not affect food intake at all in young mice (FIG. 45; (n=6 mice each for 2-month-old intestinal Slc12a8 knockdown and control female B6 mice, and n=9 mice each for 24-month-old intestinal Slc12a8 knockdown and control female B6 mice; analyzed by ANOVA with Tukey's test). Fasting glucose levels were measured in 2-month-old (2 mo) or 24-month-old (24 mo) intestinal Slc12a8 knockdown female B6 mice (shSlc12a8) and control mice (shfLuc) after 24 h fasting (FIG. 46; n=6 mice each for 2-month-old intestinal Slc12a8 knockdown and control female B6 mice, and n=9 mice each for 24-month-old intestinal Slc12a8 knockdown and control female B6 mice; analyzed by unpaired t-test). Therefore, Slc12a8 knockdown also decreased fasting glucose levels in aged mice, but not in young mice (FIG. 46). Without being limited by theory, these results illustrate that Slc12a8 expression effects NAD+ production in the gut.

Example 20

This example illustrates that the gut-specific Slc12a8 knockdown significantly increased circulating levels of glucagon-like peptide-1 (GLP-1) in the blood.

Figure 47:
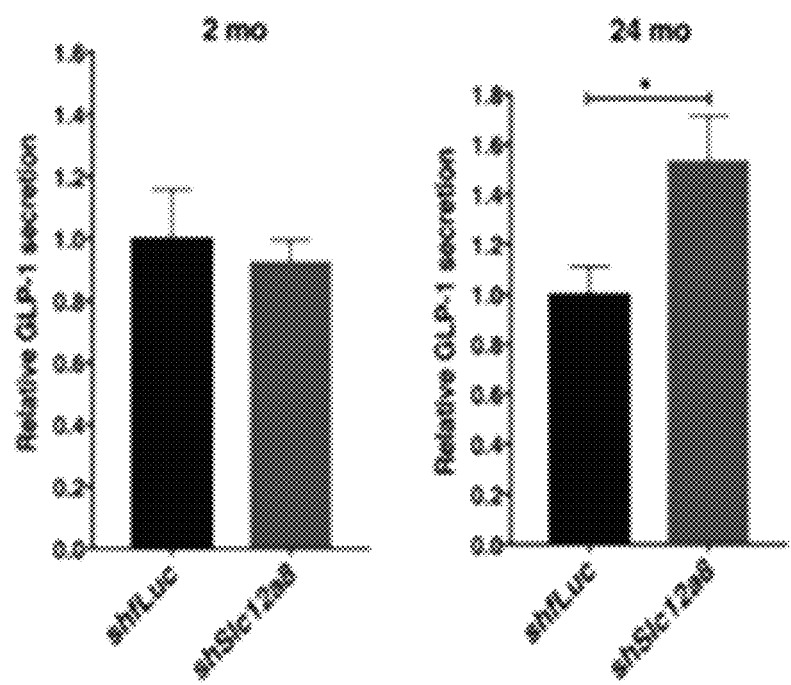
FIG. 47 illustrates the effect of refeeding after 24-hour fasts on GLP-1 levels in Slc12a8 and control mice.

GLP-1 is a proglucagon-derived anorexigenic peptide produced by enteroendocrine L cells. Plasma GLP-1 levels were measured by ELISA in 2- or 24-month-old intestinal Slc12a8 knockdown female B6 mice (shSlc12a8) and control mice (shfLuc) after 6 h refeeding following 24 h fasting (from 10 am till 4 pm). Slc12a8 knock down increased GLP-1 circulating levels in response to 6-hr refeeding after 24-hr fasting in aged mice, but not in young mice (FIG. 47; n=6 mice each for 2-month-old intestinal Slc12a8 knockdown and control female B6 mice, and n=9 mice each for 24-month-old intestinal Slc12a8 knockdown and control female B6 mice; analyzed by unpaired t-test). Without being limited by theory, these results illustrate that GLP-1 secretion is affected by Slc12a8 activity.

Example 21

This example illustrates the effect of Slc12a8 knockdown on aged ileum.

Figure 48A:
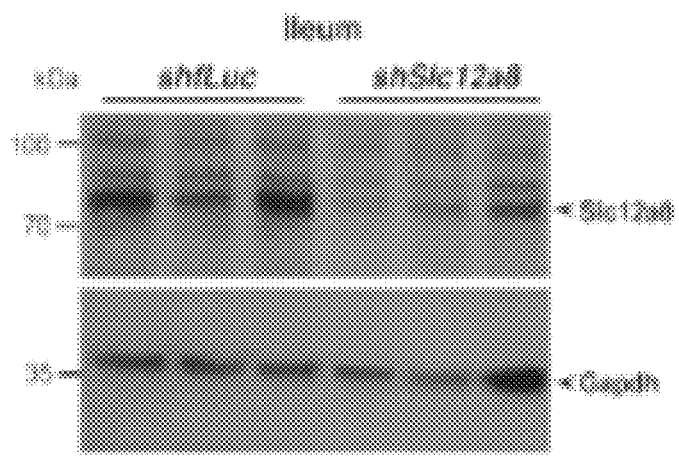
FIG. 48 illustrates Western blotting of Slc12a8 and GAPDH in ileal lysates of 2-month-old intestinal Slc12a8 knockdown mice and control mice.
Figure 48B:
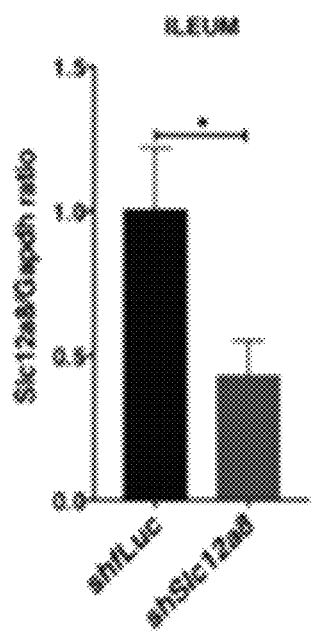
Figure 49A:
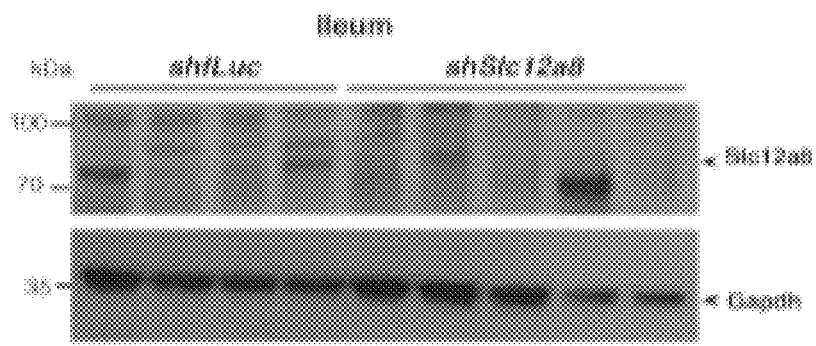
FIG. 49 illustrates Western blotting of Slc12a8 and GAPDH in ileal lysates of 24-month-old intestinal Slc12a8 knockdown mice and control mice.
Figure 49B:
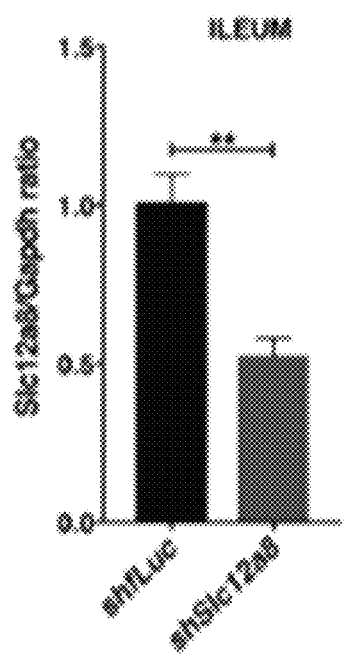
Figure 50:
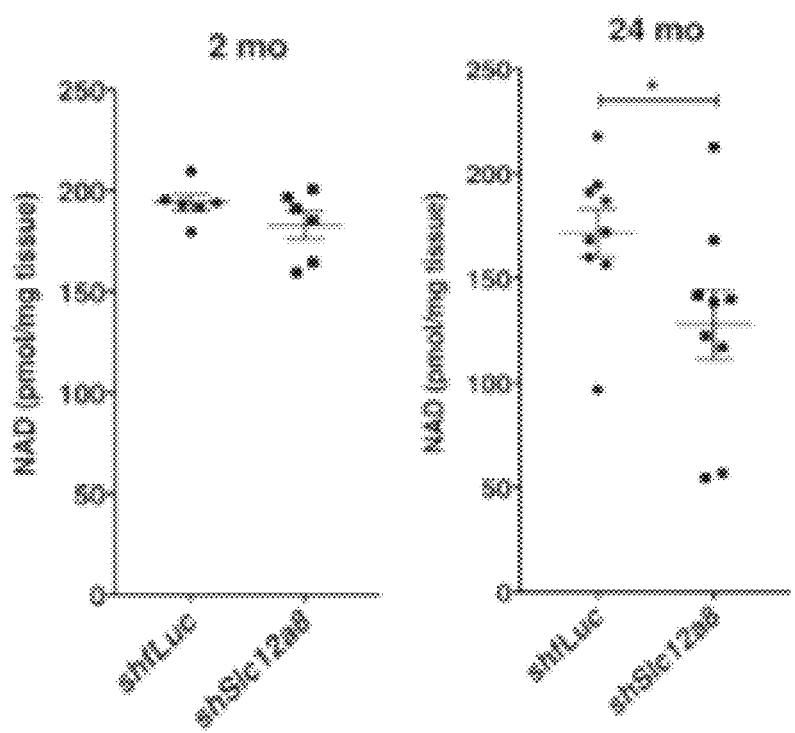
FIG. 50 illustrates NAD+ levels in the ilea of 2- or 24-month-old intestinal Slc12a8 knockdown and control mice.

It is well known that GLP-producing L cells are enriched in the ileum (Yoon, M. J., et al., Cell Metab., 2015, 21, 706-717). The expression of Slc12a8 and GAPDH in ileum was therefore examined. Western blotting of Slc12a8 and GAPDH in ileal lysates of 2-month-old (FIG. 48) or 24-month-old (FIG. 49) intestinal Slc12a8 knockdown female B6 mice (shSlc12a8) and control mice (shfLuc) was performed. FIG. 48-49 illustrate representative Western blots (left panels), and the corresponding bar graphs show Slc12a8 protein levels normalized to GAPDH protein levels in the ilea (right panels). The antiserum against the first 17 amino acids of the N-terminal domain of Slc12a8 was used (n=6 each for 2-month-old intestinal Slc12a8 knockdown and control mice, and n=4-5 each for 24-month-old intestinal Slc12a8 knockdown and control mice; analyzed by unpaired t-test). Although levels of the Slc12a8 protein significantly decreased in the ilea of young and aged Slc12a8-knockdown mice (FIG. 48-49), only the aged Slc12a8-knockdown ileum showed significant decreases in NAD+ levels (FIG. 50), confirming the physiological significance of Slc12a8 upregulation in maintaining NAD+ homeostasis in the aged ileum. FIG. 50 illustrates NAD+ levels in the ilea of 2- or 24-month-old intestinal Slc12a8 knockdown (ShSlc12a8) and control female B6 mice (ShfLuc) (n=6 mice each for 2-month-old intestinal Slc12a8 knockdown and control female B6 mice, and n=9 mice each for 24-month-old intestinal Slc12a8 knockdown and control female B6 mice; analyzed by unpaired t-test). Without being limited by theory, these results illustrates that Slc12a8 upregulation is required to maintain NAD+ homeostasis in the aged ileum.

Example 22

This example illustrates the effects of Slc12a8 knockdown on GLP-1 levels in cultured ilea.

Figure 51:
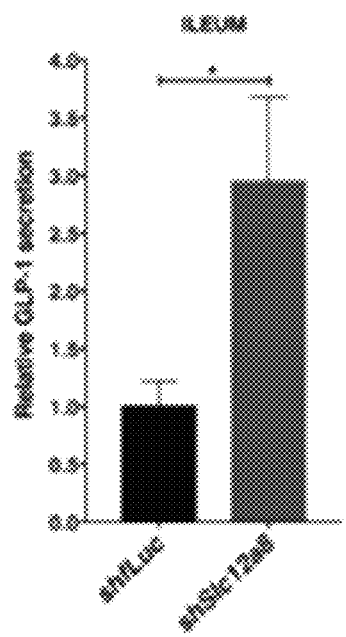
FIG. 51 illustrates ELISA of GLP-1 levels supernatants from ex vivo explants of 24-month-old intestinal Slc12a8 knockdown and control mice.
Figure 52:
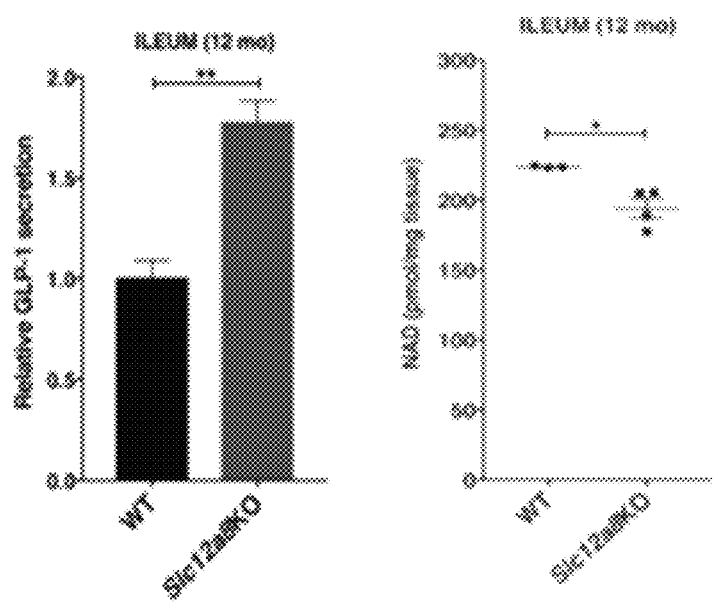
FIG. 52 illustrates GLP-1 levels in explants (left) and NAD+ levels in samples (right) of 12-month-old Slc12a8 knock out and control mice.

The inventors also cultured the ilea from aged fLuc-control and Slc12a8-knockdown mice ex vivo. GLP-1 levels were measured by ELISA in the supernatants from ex vivo ileal explants of 24-month-old intestinal Slc12a8 knockdown female B6 mice (shSlc12a8) and control mice (shfLuc) cultured for 2 h at 37° C. (n=4 mice, analyzed using unpaired t-test). FIG. 51 illustrates that the aged Slc12a8-knockdown ileum secreted 3-fold higher levels of GLP-1, compared to those from the aged fLuc-control ileum. The ex vivo-cultured colons from aged fLuc-control and Slc12a8-knockdown mice showed no differences in GLP-1 secretion. GLP-1 levels were measured by ELISA in the supernatants of ex vivo ileal explants of 12-month-old Slc12a8KO female mice (Slc12a8KO) and control wild-type littermates (WT) cultured for 2 h at 37° C. (n=4 mice; analyzed by unpaired t-test). NAD+ levels were also measured in these ileal samples from 12-month-old Slc12a8KO female mice (Slc12a8KO) and control wild-type littermates (WT) (n-3 mice for WT, and n=4 for Slc12a8KO; analyzed unpaired t-test). All values are presented as mean±SEM. $*p<0.05$, $p<0.01$. FIG. 52** illustrates increased GLP-1 secretion and decreased NAD+ in the ex vivo-cultured ilea of 12-month-old control and Slc12a8KO mice. Without being limited by theory, these examples illustrate that Slc12a8 is responsible for decreased NAD+ in the gut of aged mice.

Example 23

This example illustrates the effect of SIRT1 and SIRT6 inhibitors on ex vivo-cultured ilea.

Figure 53:
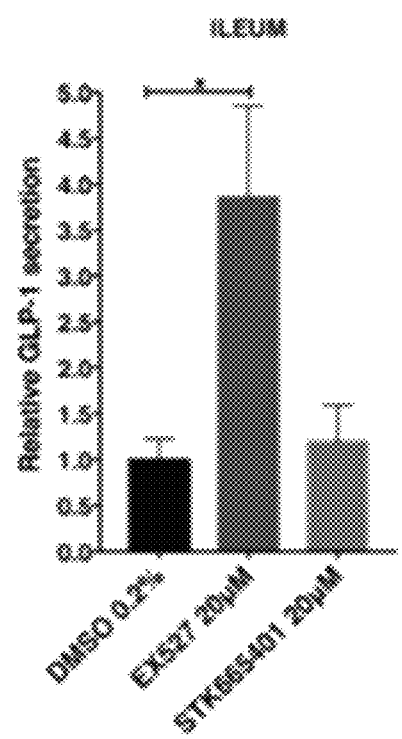
FIG. 53 illustrates GLP-1 levels in explants treated with SIRT family inhibitors or controls.

The involvement of SIRT1 (Yoon, M. J., et al., *Cell Metab.*, 2015 21, 706-717) and SIRT6 (Jiang, H. et al., Nature, 2013, 496, 110-113) in the observed increase in GLP-1 secretion was examined. Ex vivo-cultured wild-type ilea were treated with SIRT1 and SIRT6 inhibitors. GLP-1 levels were measured by ELISA in the supernatants from ex vivo ileal explants of 24-month-old female B6 mice cultured with 0.2% DMSO, 20 UM EX527 or 20 μM STK665401 for 4 h (n=3 mice, analyzed using ANOVA with Tukey's test). Only EX527, a potent SIRT1-specific inhibitor, but not STK665401, a SIRT6-specific inhibitor, was able to increase GLP-1 secretion from the ileum (FIG. 53). Without being limited by theory, these results illustrate that decreased SIRT1 activity, due to the significant $NAD^+$ decrease, is likely involved in the observed increase in GLP-1 secretion in the aged Slc12a8-knockdown ileum.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A pharmaceutical composition comprising nicotinamide mononucleotide (NMN) and an agonist of an NMN transporter a compound of structure (I)

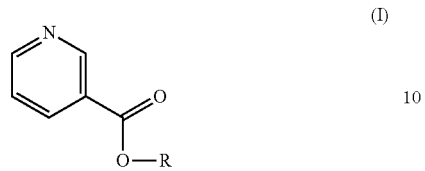

or a pharmaceutically acceptable salt thereof, wherein R is selected from the group consisting of methyl, ethyl, n-propyl, isopropyl, n-butyl, isobutyl, tert-butyl, n-hexyl, n-octyl, 2-chloroethyl, 2-hydroxyethyl, 3-hydroxypropyl, 2-methoxyethyl, 2-butoxyethyl, carbamoylmethyl, 1-carbamoylethyl, 2-dimethylaminoethyl, 3-aminopropyl, tetrahydrofurfuryl, benzyl, phenoxyethyl, p-chlorophenyl, and p-nitrophenyl.

2. The pharmaceutical composition of claim 1, wherein R is selected from the group consisting of 2-dimethylaminoethyl, p-chlorophenyl, and p-nitrophenyl.

3. The pharmaceutical composition of claim 1, wherein the NMN transporter is Slc12a8 polypeptide or a homolog thereof.

4. The pharmaceutical composition of claim 2, wherein the NMN transporter is Slc12a8 polypeptide or a homolog thereof.

* * * * *

SEQUENCE LISTING

```
Sequence total quantity: 15
SEQ ID NO: 1            moltype = DNA  length = 3166
FEATURE                 Location/Qualifiers
source                  1..3166
                        mol_type = genomic DNA
                        organism = Mus musculus
SEQUENCE: 1
```

-continued

```
atggcccaga ggtctccgca agaactcttc cacgaggcag cccagcaggg catcctggcc    60
cagcccagc cctggtggaa gatccagctg ttcatgtggg agccggtgct gtttgggacc    120
tgggatggtg tgttcacatc ctgcatgatc aacattttg gcgttgtcct tttcttgagg    180
accggctggc tggtgggaaa cacaggtgtg ctcctgggct tgctcctggt gtccttcgtc    240
gtcctcgtgg ccctcatcac cgtgctgtcg ggcattgtgc agagagca tggcgggatc    300
agcagtggcg gtgtctactc catgatctcc tcggtgcttg gtgggcagat gggaggcact    360
gtgggggctgc tctatgtatt tggacagtgt gttgcaggtg ctatgtacat caccggcttt    420
gcggagtcca tctcagatct gctgggactt ggggacatct gggcagtgcg tggaatttca    480
gttgctgtgc ttctggcttt gctgggcatc aacctggcag gtgtcaagtg gattatccgc    540
ctccagctgc tgctgctgct cctgctggct gtctcgaccc tggactttgt ggtgggctct    600
ttcacccacc tggacccaga acatggcttt attggctact ccccagaact gctacagagc    660
aacattctgc cagagtacag ccccggggag tcattcttca ctgtgtttgg ggtgttcttc    720
cctgcagcta caggagtcat ggctggcttc aacatgggag gagacctgag agaccctgct    780
gacagtgtcc ccttaggctc cctagcagct gttggcgtct cgtggttct ctacatcatc    840
tttgccttcc tgcttggtgc cgtctgtacc cgagaggccc tccgctctga cttcctgata    900
gctgaaaagg tgtctctggt tggtttcctc ttcctattgg gcctgtacat ctcatccctg    960
gcttcctgta tgggggact ctatggcgca ccccggatcc tgcagtgcat cgcccaggac    1020
aaagtcatcc ctgcactcgc cttttctggcg aatgggaaag ggcaaataa aacaccggta    1080
gcagccatct gcctgaccag cttggtgacc atggcctttg tcctggtggg tcaggtgaat    1140
gttctggcgc ccgttgtcac catcaatttc atgctgacct acatcatggt ggactactct    1200
tacttcgccc tctccatggc tcactgtggc ctcgccccat ctcctgagcc cgtccccaga    1260
caaggcccag atactctgca ctgctctgag cacctgctgg aggacaggg tcccagctac    1320
ggctctgatg tccctgccag aagcctctct gagggcaccc tgctggagtt caccaaggac    1380
atggatcagt tcctccagcc aatagaggaa ctggagagtc gtcagcttgg gtcaagagaa    1440
ggaaacaacc caaagaatca gaagcgcaag ggtaagaaag cgccaagca aaccctacaa    1500
gatagcttcc tcttggaccc tgggtctcct ttgtccttc tacgaggac ttctgagagg    1560
ttgtctgttg ccttctgtgg ggagcaagag tcctatcaga agcagcagac ttctaggagt    1620
gaatcacatg accatcttgt tcctgatcta cgcaaccagc ctagagtgaa cagagaagat    1680
ttctttctga aatgcagact tcaggaacaa gagatccaga gaagaccaag tgttttctat    1740
gcttgcatgt gtaacccctg ggtctccctg ttaggggctc ttgcatccct gctcatcatg    1800
tttgtgatcc agtggctcta taccctagct agtatgggtg ttgctgccct tgtgtatttc    1860
tacattggcc aggcaagtcc aggccttac ctcggatcag catcaaactt cagcttttc    1920
caatggatga agtccttctt ggtccctctc tgcaggagcc tgaggtccgc ccaggagcaa    1980
atcatcttgg cgccatcacc agccaaggtt gacatggcaa tgactcagct taccccaggac    2040
aatgcagact tcgccacccg agatcgttac caccactcct ccttcctgag ccggagcag    2100
ttgatgcctc cctactagga cctcgctgga ccccaccttt ctagaagccg ctgtggagat    2160
gggggaccca agcctcagaa cctttggaag ttgcttctac aataagaaa acccaagact    2220
ggtcttccca ccacagcctt ggacgctgga aatcacattc cggtctgaaa tggcatgtct    2280
agccagaatac taggtatgac tatggcttcc acgtgtgccc aacctgaaga gtccacaggc    2340
accaggatga tcaggtgaca ccaagacaac caaatgtgga gaatcaaaac gagatttctt    2400
attctaaggg gccaaaataa acactttctt taattttat tgttttattt ttattattt    2460
ttaaagaatt atatatatat acatatactg tagctatttt cagacagaaa atagcatcac    2520
cagaagaggg catcggatcc cattacagat ggttgtgagc caccatgtgg ttgctgggaa    2580
ttgaactcag gatctctgga agaacagtca gtgctcctaa ctgctgagcc atctctccag    2640
caccctcccc tgtttattt attttgtaat gtatactaac tacactcaca tggttcccaa    2700
gccacagagt atagaaaccc ccttctccct gtttctcatc tgtttggtgt ccgtccccca    2760
tcacaggcag aaccacttct catgcaaaca tcagccacct cttacagac ctttcccatc    2820
tgcaaatgca gctctgttta caatgcacta catcccgctc ttctccctta atctgccata    2880
gaagcatttc catgaagatg cttacacagt ttcctcctta tgtctctatg tctgaatgtg    2940
ccttaattta tatactcagc ctcacgagga cggcatttag cttcattctg atatttgct    3000
attacagccg cttctgcaaa gagtcactgt gtttgtgtgc acagtcgtga aggatacctg    3060
aagataaatt ctcagaagga gaattcagg gtgactgggg atgtacattt gtaagctgtt    3120
actgtttgga gaaatgcttt ttaattaaaa agtcaatcaa atacca              3166

SEQ ID NO: 2           moltype = DNA  length = 29
FEATURE                Location/Qualifiers
source                 1..29
                       mol_type = other DNA
                       organism = synthetic construct
SEQUENCE: 2
atactcgagg agaatggccc agaggtctc                                     29

SEQ ID NO: 3           moltype = DNA  length = 29
FEATURE                Location/Qualifiers
source                 1..29
                       mol_type = other DNA
                       organism = synthetic construct
SEQUENCE: 3
tcaactacgg agggatgatc gagctcatt                                     29

SEQ ID NO: 4           moltype = DNA  length = 10
FEATURE                Location/Qualifiers
source                 1..10
                       mol_type = other DNA
                       organism = synthetic construct
SEQUENCE: 4
cttcctgtca                                                          10

SEQ ID NO: 5           moltype = DNA  length = 21
```

| FEATURE | Location/Qualifiers |
|---|---|
| source | 1..21<br>mol_type = other DNA<br>organism = synthetic construct |

SEQUENCE: 5
gcctagagtg aacagagaag a                                                    21

| SEQ ID NO: 6 | moltype = AA  length = 17 |
|---|---|
| FEATURE | Location/Qualifiers |
| source | 1..17<br>mol_type = protein<br>organism = synthetic construct |

SEQUENCE: 6
AQRSPQELFH EAAQQGC                                                         17

| SEQ ID NO: 7 | moltype = DNA  length = 20 |
|---|---|
| FEATURE | Location/Qualifiers |
| source | 1..20<br>mol_type = other DNA<br>organism = synthetic construct |

SEQUENCE: 7
agtgcatgta tagacgtatg                                                      20

| SEQ ID NO: 8 | moltype = DNA  length = 20 |
|---|---|
| FEATURE | Location/Qualifiers |
| source | 1..20<br>mol_type = other DNA<br>organism = synthetic construct |

SEQUENCE: 8
cctcacaaat atttacaggc                                                      20

| SEQ ID NO: 9 | moltype = DNA  length = 2004 |
|---|---|
| FEATURE | Location/Qualifiers |
| source | 1..2004<br>mol_type = genomic DNA<br>organism = Mus musculus |

SEQUENCE: 9
```
atggcccaga ggtctccgca agaactcttc cacgaggcag cccagcaggg catcctggcc   60
cagccccagc cctggtggaa gatccagctg ttcatgtggg agccggtgct gtttgggacc  120
tgggatggtg tgttcacatc ctgcatgatc aacattttg gcgttgtcct tttcttgagg   180
accggctggc tggtgggaaa cacaggtgtg ctcctgggct tgctcctggt gtccttcgtc  240
gtcctcgtgg ccctcatcac cgtgctgtcg ggcattggtg tcgcagagca tggcgggatc  300
agcagtgggcg gtgtctactc catgatctcc tcggtgcttg gtgggcagat gggaggcact  360
gtggggctgc tctatgtatt tggacagtgt gttgcaggtg ctatgtacat caccggcttt  420
gcggagtcca tctcagatct gctgggactt ggggacatct gggcagtgcg tggaatttca  480
gttgctgtgc ttctggcttt gctgggcatc aacctgcag gtgtcaagtg gattatccgc  540
ctccagctgc tgctgctgct cctgctggct gtctcgaccc tggactttgt gctgggctct  600
ttcacccacc tggacccagg agtcatggct ggcttcaaca tgggaggaga cctgagagac  660
cctgctgaca gtgtccccct aggctcccta gcagctgttg cgctcgtg tttctctac    720
atcatctttg ccttcctgct tggtgccgtc tgtacccgag aggccctccg ctctgacttc  780
ctgatagctg aaaaggtgtc tctggttggt ttcctcttcc tattgggcct gtacatctca  840
tccctggctt cctgtatggg gggactctat ggcgcacccc ggatcctgca gtgcatcgcc  900
caggacaaag tcatccctgc actcgccttt ctggcgaatg ggaaagggcc aaataaaaca  960
ccggtagcag ccatctgcct gaccagcttg gtgaccatgg cctttgtcct ggtgggtcag 1020
gtgaatgttc tggcgcccgt tgtcaccatc aatttcatgc tgacctacat catggtggac 1080
tactcttact tcgccctctc catggctcac tgtggcctcg ccccatctcc tgagcccgtc 1140
cccagacaag gcccagatac tctgcactgc tctgagcacc tgctcaggga cagggctccc 1200
agctacggct ctgatgtccc tgccagaagc ctctctgagg gcaccctgct ggagttcacc 1260
aaggacatgg atcagttcct ccagccaata ggagaactgg agagtcgtca gcttgggtca 1320
agagaaggaa acaacccaaa gaatcagaag cgcaagggta agaaggcgc caagcaaacc 1380
ctacaagata gcttcctctt ggaccctggg tctcctttgt cctttcctac gaggacttct 1440
gagaggttgt ctgttgcctt ctgtggggag caagagtcct atcagaagca gcagacttct 1500
aggagtgaat cacatgacca tcttgttcct gatctacgca accagcctag agtgaacaga 1560
gaagatttct ttctgaaatg cagacttcag gaacaagaga tccagaagaag accaagtgtt 1620
ttctatgctt gcatgtgtaa cccctgggtc tccctgttag gggctcttgc atccctgctc 1680
atcatgtttg tgatccagtg gctctatacc ctagctagta tgggtgttgc tgcccttgtg 1740
tatttctaca ttggccaggc aagtccaggc ctttacctcg gatcagcatc aaacttcagc 1800
tttttccaat ggatgaagtc cttccttggtc ccctcctgca ggagcctgag gtccgcccag 1860
gagcaaatca tcttggcgcc atcaccagcc aaggttgaca tggcaatgac tcagcttacc 1920
caggacaatg cagacttcgc cacccgagat cgttaccacc actcctcctt cctgagccgg 1980
gagcagttga tgcctcccta ctag                                      2004
```

| SEQ ID NO: 10 | moltype = DNA  length = 1779 |
|---|---|
| FEATURE | Location/Qualifiers |
| source | 1..1779<br>mol_type = genomic DNA<br>organism = Mus musculus |

SEQUENCE: 10
atggcccaga ggtctccgca agaactcttc cacgaggcag cccagcagtg tgttgcaggt   60

```
gctatgtaca tcaccggctt tgcggagtcc atctcagatc tgctgggact tggggacatc    120
tgggcagtgc gtggaatttc agttgctgtg cttctggctt tgctgggcat caacctggca    180
ggtgtcaagt ggattatccg cctccagctg ctgctgctgc tcctgctggc tgtctcgacc    240
ctggactttg tggtgggctc tttcacccac ctggacccag aacatggctt tattggctac    300
tcccagaac tgctacagag caacattctg ccagagtaca gccccgggga gtcattcttc    360
actgtgtttg gggtgttctt ccctgcagct acaggagtca tggctgggct caacatggga    420
ggagacctga gagaccctgc tgacagtgtc cccttaggct cccagcagc tgttggcgtc     480
tcgtggtttc tctacatcat ctttgccttc ctgcttggtg ccgtctgtac ccgagaggcc    540
ctccgctctg acttcctgat agctgaaaag gtgtctctgg ttggtttcct cttcctattg    600
ggcctgtaca tctcatccct ggcttcctgt atgggggac tctatggcgc acccccggatc    660
ctgcagtgca tcgcccagga caaagtcatc cctgcactcg cctttctggc gaatgggaaa    720
gggccaaata aaacaccggt agcagccatc tgcctgacca gcttggtgac catggccttt    780
gtcctggtgg gtcaggtgaa tgttctggcg cccgttgtca ccatcaattt catgctgacc    840
tacatcatgg tggactactc ttacttcgcc ctctccatgg ctcactgtgg cctcgcccca    900
tctcctgagc ccgtcccag acaaggccca gatactctgc actgtctga gcacctgctc     960
caggacaggg ctcccagcta cggctctgat gtccctgcca gaagcctctc tgagggcacc    1020
ctgctggagt tcaccaagga catggatcag ttcctccagc caatagagga actggagagt    1080
cgtcagcttg ggtcaagaga aggaaacaac ccaaagaatc agaagcgcaa gggtaagaaa    1140
ggcgccaagc aaaccctaca agatagcttc ctcttggacc ctgggtctcc tttgtccttt    1200
cctacgagga cttctgagag gttgtctgtt gccttctgtg gggagcaaga gtcctatcag    1260
aagcagcaga cttctaggag tgaatcacat gaccatcttg ttcctgatct acgcaaccag    1320
cctagagtga acagagaaga tttctttctg aaatgcaaga ttcaggaaca agagatccag    1380
agaagaccaa gtgttttcta tgcttgcatg tgtaaccct gggtctccct gttaggggct    1440
cttgcatccc tgctcatcat gtttgtgatc cagtggctct ataccctagc tagtatgggt    1500
gttgctgccc ttgtgtattt ctacattggc caggcaagtc caggccttta cctcggatca    1560
gcatcaaact tcagcttttt ccaatggatg aagtccttct tggtccctc ctgcaggagc     1620
ctgaggtccg cccaggagca aatcatcttg gcgccatcac cagccaaggt tgacatggag    1680
atgactcagc ttacccagga caatgcagac ttcgccaccc gagatcgtta ccaccactcc    1740
tccttcctga gccgggagca gttgatgcct ccctactag                          1779

SEQ ID NO: 11        moltype = DNA  length = 2145
FEATURE              Location/Qualifiers
source               1..2145
                     mol_type = genomic DNA
                     organism = Homo sapiens
SEQUENCE: 11
atgacccaga tgtcccaggt gcaggagctc ttccatgagg cagcccagca ggatgccctg     60
gcccagcccc agccctggtg gaagaccag ctgttcatgt gggagcctgt gctgtttggg    120
acctggatg gtgtgttcac atcctgcatg atcaacatct ttggggttgt gctcttcctg    180
aggactggct ggctggtggg aaacacagga gtgctcctgg gcatgttcct ggtgtccttc    240
gtcatcctgg tggccctcgt cacggtgctg tctggcattg gcgtcgggga gcgcagcagc    300
atcggcagcg gtggcgtcta ctccatgatc tcctcggtcc tgggtgggca gacgggaggc    360
accatcggc tgctctatgt gtttggacag tgtgttgcag gtgccatgta tatcaccggc    420
tttgctgaat ccatctcgga tttgctgggc ctcgggaata tctgggctgt gcgaggaatt    480
tcagttgcgg tgcttctggc cttgctgggc attaacctcg caggtgtcaa atggataatc    540
cgcctccagc tgctgttgct gttcctgctg ccgtgtcca cactggactt tgtggtgggt    600
tctttcaccc acctggaccc agaacatggt tcattgagat attcaccgga actgctacag    660
aacaacacgc tgcccgatta cagcccgggg gaatctttt tcactgtctt tggggttttc    720
ttcccagcgc tacaggagt catggccggc ttcaacatgg gggcgacct cagggagcct     780
gccgccagca ttccctgggg ctccctggca gctgttggca tctcgtggtt tctgtacatc    840
atcttcgtct tcctcctggg cgccatctgc actcgagagg cccttcgcta tgacttctg    900
atagcggaaa aggtatccct catgggcttc ctgttccttt gggcttata catctcgtcc    960
ctggcttcct gcatgggagg actttatgga gctcccgca cctgcagtg cattgcccag    1020
gagaaagtga tccctgcact tgcctgtctg ggacaaggga aggggccaaa caaaacaccc    1080
gtggctgcca tctgcctgac cagcttggtg accatgggct ttgttttttg gggtcaagtg    1140
aacgttctgg cccccatcgt caccatcaac ttcatgctga catacgttgc agtggactac    1200
tcttacttct ccctgtccat gtgttcctgc agcctgaccc cggtgcctga ccggtgctc    1260
agggagggcg cagaaggcct ccactgctct gagcacctgc tcttagagaa agctcccagt    1320
tacggcctcg agggacctgc ccaaagagtc ttggagggca cgctactgga attcaccaag    1380
gacatggatc agctcctcca gctaaccagg aagcttgaga gtagccagcc caggcaagga    1440
gagggtaaca ggaccccaga aagtcagaag aggaaaagca agaaggccac caagcagacc    1500
ctacaagata gcttcctctt ggacctcaaa tcccctcctt cttcctgt cgagatctct     1560
gacaggttgc ccgctgcctc ctgggagggg caggagtcct gctggaacaa gcagacttcc    1620
aagagcgaag ggactcagcc tgagggaaca tatggagagc aacttgttcc tgagctgtgc    1680
aaccaatcag agtccagtgg agaagattc ttcctgaagt ccaggctcca agaacaagat    1740
gtctggagaa gatccacttc tttctatacc cacatgtgca accccggggt ctccctgttg    1800
gggctgttg ggtcccttct catcatgttt gtgatacagt gggtgtatac cctggttaac    1860
atgggtgttg ctgccatcgt gtattctac attggccggg ccagtccagg gcttcacctt    1920
ggatcagcct ccaacttcag cttttccgg tggatgaagt ctcttgct ccctcctgc      1980
aggagcttgc ggtccctca ggagcagatc atcttgccgc cgtccctggc taaggttgac    2040
atggagatga ctcagctcac ccaggagaat gcagacttcg ccactcggga tcgtaccac    2100
cactcctccc tcgtgaaccg ggagcagctg atgcctcact actag                   2145

SEQ ID NO: 12        moltype = AA   length = 705
FEATURE              Location/Qualifiers
source               1..705
                     mol_type = protein
                     organism = Mus musculus
SEQUENCE: 12
```

```
MAQRSPQELF HEAAQQGILA QPQPWWKIQL FMWEPVLFGT WDGVFTSCMI NIFGVVLFLR    60
TGWLVGNTGV LLGLLLVSFV VLVALITVLS GIGVAEHGGI SSSGGVYSMIS SVLGGQMGGT  120
VGLLYVFGQC VAGAMYITGF AESISDLLGL GDIWAVRGIS VAVLLALLGI NLAGVKWIIR  180
LQLLLLLLLA VSTLDFVVGS FTHLDPEHGF IGYSPELLQS NILPEYSPGE SFFTVFGVFF  240
PAATGVMAGF NMGGDLRDPA DSVPLGSLAA VGVSWFLYII FAFLLGAVCT REALRSDFLI  300
AEKVSLVGFL FLLGLYISSL ASCMGGLYGA PRILQCIAQD KVIPALAFLA NGKGPNKTPV  360
AAICLTSLVT MAFVLVGQVN VLAPVVTINF MLTYIMVDYS YFALSMAHCG LAPSPEPVPR  420
QGPDTLHCSE HLLQDRAPSY GSDVPARSLS EGTLLEFTKD MDQFLQPIEE LESRQLGSRE  480
GNNPKNQKRK GKKGAKQTLQ DSFLLDPGSP LSFPTRTSER LSVAFCGEQE SYQKQQTSRS  540
ESHDHLVPDL RNQPRVNRED FFLKCRLQEQ EIQRRPSVFY ACMCNPWVSL LGALASLLIM  600
FVIQWLYTLA SMGVAALVYF YIGQASPGLY LGSASNFSFF QWMKSFLVPS CRSLRSAQEQ  660
IILAPSPAKV DMAMTQLTQD NADFATRDRY HHSSFLSREQ LMPPY                 705

SEQ ID NO: 13         moltype = AA  length = 667
FEATURE               Location/Qualifiers
source                1..667
                      mol_type = protein
                      organism = Mus musculus
SEQUENCE: 13
MAQRSPQELF HEAAQQGILA QPQPWWKIQL FMWEPVLFGT WDGVFTSCMI NIFGVVLFLR    60
TGWLVGNTGV LLGLLLVSFV VLVALITVLS GIGVAEHGGI SSSGGVYSMIS SVLGGQMGGT  120
VGLLYVFGQC VAGAMYITGF AESISDLLGL GDIWAVRGIS VAVLLALLGI NLAGVKWIIR  180
LQLLLLLLLA VSTLDFVVGS FTHLDPGVMA GFNMGGDLRD PADSVPLGSL AAVGVSWFLY  240
IIFAFLLGAV CTREALRSDF LIAEKVSLVG FLFLLGLYIS SLASCMGGLY GAPRILQCIA  300
QDKVIPALAF LANGKGPNKT PVAAICLTSL VTMAFVLVGQ VNVLAPVVTI NFMLTYIMVD  360
YSYFALSMAH CGLAPSPEPV PRQGPDTLHC SEHLLQDRAP SYGSDVPARS LSEGTLLEFT  420
KDMDQFLQPI EELESRQLGS REGNNPKNQK RKGKKGAKQT LQDSFLLDPG SPLSFPTRTS  480
ERLSVAFCGE QESYQKQQTS RSESHDHLVP DLRNQPRVNR EDFFLKCRLQ EQEIQRRPSV  540
FYACMCNPWV SLLGALASLL IMFVIQWLYT LASMGVAALV YFYIGQASPG LYLGSASNFS  600
FFQWMKSFLV PSCRSLRSAQ EQIILAPSPA KVDMAMTQLT QDNADFATRD RYHHSSFLSR  660
EQLMPPY                                                            667

SEQ ID NO: 14         moltype = AA  length = 592
FEATURE               Location/Qualifiers
source                1..592
                      mol_type = protein
                      organism = Mus musculus
SEQUENCE: 14
MAQRSPQELF HEAAQQCVAG AMYITGFAES ISDLLGLGDI WAVRGISVAV LLALLGINLA    60
GVKWIIRLQL LLLLLLAVST LDFVVGSFTH LDPEHGFIGY SPELLQSNIL PEYSPGESFF  120
TVFGVFFPAA TGVMAGFNMG GDLRDPADSV PLGSLAAVGV SWFLYIIFAF LLGAVCTREA  180
LRSDFLIAEK VSLVGFLFLL GLYISSLASC MGGLYGAPRI LQCIAQDKVI PALAFLANGK  240
GPNKTPVAAI CLTSLVTMAF VLVGQVNVLA PVVTINFMLT YIMVDYSYFA LSMAHCGLAP  300
SPEPVPRQGP DTLHCSEHLL QDRAPSYGSD VPARSLSEGT LLEFTKDMDQ FLQPIEELES  360
RQLGSREGNN PKNQKRKGKK GAKQTLQDSF LLDPGSPLSF PTRTSERLSV AFCGEQESYQ  420
KQQTSRSESH DHLVPDLRNQ PRVNREDFFL KCRLQEQEIQ RRPSVFYACM CNPWVSLLGA  480
LASLLIMFVI QWLYTLASMG VAALVYFYIG QASPGLYLGS ASNFSFFQWM KSFLVPSCRS  540
LRSAQEQIIL APSPAKVDMA MTQLTQDNAD FATRDRYHHS SFLSREQLMP PY           592

SEQ ID NO: 15         moltype = AA  length = 714
FEATURE               Location/Qualifiers
source                1..714
                      mol_type = protein
                      organism = Homo sapiens
SEQUENCE: 15
MTQMSQVQEL FHEAAQQDAL AQPQPWWKTQ LFMWEPVLFG TWDGVFTSCM INIFGVVLFL    60
RTGWLVGNTG VLLGMFLVSF VILVALVTVL SGIGVGERSS IGSGGVYSMI SSVLGGQTGG  120
TIGLLYVFGQ CVAGAMYITG FAESISDLLG LGNIWAVRGI SVAVLLALLG INLAGVKWII  180
RLQLLLLFLL AVSTLDFVVG SFTHLDPEHG FIGYSPELLQ NNTLPDYSPG ESFFTVFGVF  240
FPAATGVMAG FNMGGDLREP AASIPLGSLA AVGISWFLYI IFVFLLGAIC TREALRYDFL  300
IAEKVSLMGF LFLLGLYISS LASCMGGLYG APRILQCIAQ EKVIPALACL GQGKGPNKTP  360
VAAICLTSLV TMAFVFVGQV NVLAPIVTIN FMLTYVAVDY SYFSLSMCSC SLTPVPEPVL  420
REGAEGLHCS EHLLLEKAPS YGSEGPAQRV LEGTLLEFTK DMDQLLQLTR KLESSQPRQG  480
EGNRTPESQK RKSKKATKQT LQDSFLLDLK SPPSFPVEIS DRLPAASWEG QESCWNKQTS  540
KSEGTQPEGT YGEQLVPELC NQSESSGEDF FLKSRLQEQD VWRRSTSFYT HMCNPWVSLL  600
GAVGSLLIMF VIQWVYTLVN MGVAAIVYFY IGRASPGLHL GSASNFSFFR WMRSLLLPSC  660
RSLRSPQEQI ILAPSLAKVD MEMTQLTQEN ADFATRDRYH HSSLVNREQL MPHY         714
```